United States Patent
Catalano et al.

(10) Patent No.: US 7,282,512 B2
(45) Date of Patent: Oct. 16, 2007

(54) CYCLOALKYL KETOAMIDES DERIVATIVES USEFUL AS CATHEPSIN K INHIBITORS

(75) Inventors: John George Catalano, Durham, NC (US); David Norman Deaton, Durham, NC (US); Aaron Bayne Miller, Durham, NC (US); Francis Xavier Tavares, Durham, NC (US)

(73) Assignee: SmithKline Beecham Corporation, Philadelphia, PA (US)

( * ) Notice: Subject to any disclaimer, the term of this patent is extended or adjusted under 35 U.S.C. 154(b) by 335 days.

(21) Appl. No.: 10/501,636

(22) PCT Filed: Jan. 15, 2003

(86) PCT No.: PCT/US03/01271

§ 371 (c)(1),
(2), (4) Date: Jul. 15, 2004

(87) PCT Pub. No.: WO03/062192

PCT Pub. Date: Jul. 31, 2003

(65) Prior Publication Data

US 2005/0054819 A1    Mar. 10, 2005

Related U.S. Application Data

(60) Provisional application No. 60/349,812, filed on Jan. 17, 2002.

(51) Int. Cl.
*A61K 31/41*    (2006.01)
*C07D 233/00*    (2006.01)

(52) U.S. Cl. .................. 514/362; 514/365; 514/385; 514/396; 514/403; 548/316.4; 548/186; 548/152; 548/128

(58) Field of Classification Search ............ 548/316.4, 548/186, 152, 128; 514/362, 365, 385, 396, 514/403
See application file for complete search history.

(56) References Cited

U.S. PATENT DOCUMENTS

| | | | |
|---|---|---|---|
| 5,444,042 A | | 8/1995 | Bartus et al. |
| 5,501,969 A | | 3/1996 | Hastings et al. |
| 5,514,694 A | | 5/1996 | Powers et al. |
| 5,610,297 A | | 3/1997 | Powers |
| 5,650,508 A | | 7/1997 | Powers |
| 5,670,479 A | | 9/1997 | Abelman et al. |
| 5,763,576 A | | 6/1998 | Powers |
| 5,861,298 A | | 1/1999 | Adams et al. |
| 5,948,777 A | * | 9/1999 | Bender et al. ............ 514/235.8 |
| 5,948,886 A | | 9/1999 | Peet et al. |
| 6,143,931 A | | 11/2000 | Baldino et al. |
| 6,235,929 B1 | | 5/2001 | Powers |
| 6,291,505 B1 | * | 9/2001 | Huebner et al. ............ 514/406 |
| 6,436,925 B1 | | 8/2002 | Lubisch et al. |
| 6,448,254 B1 | | 9/2002 | Lubisch et al. |
| 2005/0043368 A1 | * | 2/2005 | Deaton et al. ............ 514/357 |

FOREIGN PATENT DOCUMENTS

| | | |
|---|---|---|
| EP | 520 427 | 12/1992 |
| EP | 525 420 | 2/1993 |
| EP | 535 928 | 4/1993 |
| EP | 603 873 | 6/1994 |
| EP | 611 756 | 8/1994 |
| EP | 812 916 | 12/1997 |
| EP | 1 008 592 | 6/2000 |
| JP | 200281640 A | 11/1990 |
| JP | 06192199 | 7/1994 |
| JP | 11263783 | 7/1994 |
| JP | 07115985 | 5/1995 |
| JP | 11228526 | 8/1999 |
| JP | 11246436 | 9/1999 |
| JP | 2001011037 | 1/2001 |
| WO | 92/11850 | 7/1992 |
| WO | 92/12140 | 7/1992 |
| WO | 93/24634 | 12/1993 |
| WO | 94/00095 | 1/1994 |
| WO | 94/08941 | 4/1994 |
| WO | 94/21673 | 9/1994 |
| WO | 95/00535 | 1/1995 |
| WO | 96/10014 | 4/1996 |
| WO | 96/16079 | 5/1996 |
| WO | 96/32408 | 10/1996 |
| WO | 96/40647 | 12/1996 |
| WO | 97/16177 | 5/1997 |

(Continued)

OTHER PUBLICATIONS

Tezuka et al., "Molecular Cloning of a Possible Cystein Proteinase Predominantly Expressed in Osteoclasts," *J. Biol. Chem.*, 1994, vol. 269, pp. 1106-1109.

(Continued)

*Primary Examiner*—Rebecca Anderson
*Assistant Examiner*—Rei-tsang Shiao
(74) *Attorney, Agent, or Firm*—John L. Lemanowicz; Kathryn L. Coulter

(57) ABSTRACT

Cycloalkyl ketoamide derivatives, which are useful as cathepsin K inhibitors are described herein. The described invention also includes methods of making such cycloalkyl ketoamide derivatives as well as methods of using the same in the treatment of disorders, including osteoporosis, associated with enhanced bone turnover which can ultimately lead to fracture.

33 Claims, No Drawings

FOREIGN PATENT DOCUMENTS

| | | |
|---|---|---|
| WO | 97/16433 | 5/1997 |
| WO | 97/47642 | 12/1997 |
| WO | 97/49668 | 12/1997 |
| WO | 98/05336 | 2/1998 |
| WO | 98/08802 | 3/1998 |
| WO | 98/46559 | 10/1998 |
| WO | 98/48190 | 10/1998 |
| WO | 9846582 | 10/1998 |
| WO | 98/48799 | 11/1998 |
| WO | 98/50342 | 11/1998 |
| WO | 98/50534 | 11/1998 |
| WO | 99/11637 | 3/1999 |
| WO | 99/11640 | 3/1999 |
| WO | 99/17775 | 4/1999 |
| WO | 99/17778 | 4/1999 |
| WO | 99/17790 | 4/1999 |
| WO | 99/24460 | 5/1999 |
| WO | 99/37666 | 7/1999 |
| WO | 99/53039 | 10/1999 |
| WO | 99/54305 | 10/1999 |
| WO | 99/54310 | 10/1999 |
| WO | 99/54317 | 10/1999 |
| WO | 99/54320 | 10/1999 |
| WO | 99/59526 | 11/1999 |
| WO | 99/59570 | 11/1999 |
| WO | 99/61423 | 12/1999 |
| WO | 99/64399 | 12/1999 |
| WO | 99/66925 | 12/1999 |
| WO | 00/01666 | 1/2000 |
| WO | 00/16767 | 3/2000 |
| WO | 00/18358 | 4/2000 |
| WO | 00/18725 | 4/2000 |
| WO | 00/24704 | 5/2000 |
| WO | 00/29408 | 5/2000 |
| WO | 00/51998 | 9/2000 |
| WO | 00/54769 | 9/2000 |
| WO | 00/55124 | 9/2000 |
| WO | 00/55144 | 9/2000 |
| WO | 00/58296 | 10/2000 |
| WO | 00/59881 | 10/2000 |
| WO | 00/78794 | 12/2000 |
| WO | 01/09169 | 2/2001 |

OTHER PUBLICATIONS

Inaoka et al., "Molecular Cloning of Human cDNA for Cathepsin K: Novel Cysteine Proteinase Predominately Expressed in Bone," *Biochem. Biophys. Res. Commun.*, 1995, vol. 206, p. 89.

Shi, et al., "Molecular cloning of human cathepsin I, a novel endoproteinase asn homologue of rabbit OC2," *FEBS Letters*, 1995, vol. 357, p. 129.

Lalonde, J.M. et al., "Use a Papain as a Model for the Structure-Based Design of Cathepsin K Inhibitors: Crystal Structures of Two Papain-Inhibitor Complexes Demonstrate Binding to S-Subsites," *Journal of Medicinal Chemistry*, vol. 41, 1998, pp. 4567-4576.

* cited by examiner

CYCLOALKYL KETOAMIDES DERIVATIVES USEFUL AS CATHEPSIN K INHIBITORS

This application is filed pursuant to 35 U.S.C. § 371 as a United States National Phase Application of International Application No. PCT/US03/01271 filed Jan. 15, 2003. which claims priority from US 60/349,812 filed Jan. 17, 2002.

BACKGROUND OF THE INVENTION

The present invention relates to cycloalkyl substituted ketoamide derivatives, compositions and medicaments containing the same, as well as processes for the preparation and use of such compounds, compositions and medicaments. Such ketoamide derivatives are inhibitors of serine and cysteine proteases. Particularly, such ketoamide derivatives are inhibitors of cysteine proteases of the papain superfamily. More particularly, the ketoamides of the present invention are inhibitors of cathepsin family cysteine proteases such as cathepsin K. Such ketoamide derivatives are useful in the treatment of diseases associated with serine and cysteine protease activity, more particularly, in the treatment of diseases associated with cathepsin family cysteine proteases, for instance in the treatment of diseases associated with cathepsin K activity.

Osteoclasts are multinuclear cells of hematopoietic lineage, which function in the process of bone resorption. Typically, bone resorption proceeds as follows: The osteoclasts adhere to a bone surface and form a tight sealing zone. This activity is followed by extensive membrane ruffling on the surface of the osteoclasts. Such action creates an enclosed extracellular compartment on the bone surface that is acidified by proton pumps in the ruffled membrane and into which the osteoclast secretes proteolytic enzymes. The low pH of the compartment dissolves hydroxyapatite crystals at the bone surface, while the proteolytic enzymes digest the protein matrix. In this way a resorption pit is formed. At the completion of this cycle osteoblasts remodel the bone; that is, deposit a new protein matrix, which is subsequently mineralized at this zone.

Normally, a balance exists between the processes of bone resorption and new bone formation during remodeling. This normal balance of bone resorption and bone formation may be disrupted resulting in a net loss of bone in each cycle of remodeling. Such net bone loss may lead to osteoporosis. Osteoporosis is characterized by reduced bone mass and disruptions in the microarchitecture of the bone. These characteristics may lead to fractures, which can result from a minimal amount of trauma. Typical sites of fractures include vertebral bodies, distal radius, and the proximal femur. However, because those suffering from osteoporosis have general skeletal weakness, fractures may occur at other sites.

Since osteoporosis is characterized by an increase in bone resorption with respect to bone remodeling, therapeutic agents that suppress bone resorption would be expected to provide a suitable treatment for osteoporosis. Administration of estrogens or calcitonin has been the bone resorption suppression treatment typically employed. However, these treatments do not always achieve the desired effect Consequently, there is a continuing need for therapeutic agents which can attenuate bone resorption in a subject in need of such attenuation.

Cathepsin K, which has also been called cathepsin O, cathepsin O2, and cathepsin X, is a member of the cysteine cathepsin family of enzymes, which are part of the papain superfamily of cysteine proteases. Other distinct cysteine protease cathepsins, designated cathepsin B, cathepsin C, cathepsin F, cathepsin H, cathepsin L, cathepsin O, cathepsin S, cathepsin V (also called L2), cathepsin W, & cathepsin Z (also called cathepsin X), have also been described in the literature. Cathepsin K polypeptide and the cDNA encoding such polypeptide have been disclosed in U.S. Pat. No. 5,501,969. A crystal structure for cathepsin K has also been disclosed in PCT Patent Application WO 97/16177, published May 9, 1997. It has been reported that cathepsin K is abundantly expressed in osteoclasts under normal conditions and may be the major cysteine protease present in these cells. (See Tezuka, et al., J. Biol. Chem., 1994, 269, 1106; Inaoka, et al, Biochem. Biophys. Res. Commun., 1995, 206, 89; and Shi, et al., FEBS Lett., 1995, 357,129.) This abundant selective expression of cathepsin K in osteoclasts suggests that this enzyme is essential for bone resorption. Thus, selective inhibition of cathepsin K may provide an effective treatment for diseases of excessive bone loss, such as osteoporosis.

The selective inhibition of cathepsin K may also be useful in treating other diseases. Such disorders include autoimmune diseases such as rheumatoid arthritis, osteoarthritis, neoplastic diseases, parasitic diseases, and atherosclerosis. For instance, cathepsin K is expressed in the synovium and synovial bone destruction sites of patients with rheumatoid arthritis (see Votta, B. J. et al.; *J. Bone Miner. Res*. 1997, 12, 1396; Hummel, K. M. et al., *J. Rheumatol*. 1998, 25, 1887; Nakagawa, T. Y. et al., *Immunity* 1999, 10, 207; Otsuka, T. et al., S. *J. Antibiot* 1999, 52, 542; Li, Z. et al, *Biochemistry* 2000, 39, 529; Diaz, A. et al, *Mol. Med*. 2000, 6, 648; Moran, M. T. et al., *Blood* 2000, 96, 1969). Cathepsin K levels are elevated in chondroclasts of osteoarthritic synovium (See Dodds, R. A. et al., *Arthritis Rheum*. 1999, 42, 1588; Lang, A. et al., *J. Rheumatol*. 2000, 27, 1970). Neoplastic cells also have been shown to express cathepsin K (see Littlewood-Evans, A. J. et al, J. A. *Cancer Res*. 1997, 57, 5386; Komarova, E. A., et al., *Oncogene* 1998, 17, 1089; Santamaria, I., et al., *Cancer Res*. 1998, 58, 1624; Blagosklonny, M. V. et al., *Oncogene* 1999, 18, 6460; Kirschke, H. et al., *Eur. J. Cancer* 2000, 36, 787; Zhu, D.-M. et al., *Clin. Cancer Res*. 2000, 6, 2064). Cysteine protease inhibitors have been suggested as chemotherapy for parasitic diseases (see McKerrow, J. H. *Int. J. Parasitol*. 1999, 29, 833; Selzer, P. M. et al., *Proc. Natl. Acad. Sci. U.S.A*. 1999, 96, 11015; Caffrey, C. R. et al, *Curr. Drug Targets* 2000, 1, 155; Du, X. et al., *Chem. Biol*. 2000, 7, 733; Hanspal, M. *Biochim. Biophys. Acta* 2000, 1493, 242; Werbovetz, K. A. *Curr. Med. Chem*. 2000, 7, 835). Elastolytic cathepsins S and K are shown to be expressed in human atheroma (see Sukhova, G. K. et al., *J. Clin. Invest*. 1998, 102, 576-583; Parks, W. C. *J. Clin. Invest*. 1999, 104, 1167; Shi, G.-P. et al., *J. Clin. Invest* 1999, 104, 1191; Cao, H. et al., *J. Hum. Genet*. 2000, 45, 94).

The present inventors have now discovered novel cycloalkyl substituted ketoamide derivative compounds, which are inhibitors of serine and cysteine protease activities, more particularly, cathepsin family cysteine protease activities, and most particularly, cathepsin K activity. Such ketoamide derivatives are useful in the treatment of disorders associated with serine and cysteine protease activity, including osteoporosis, Paget's disease, hypercalcemia of malignancy, metabolic bone disease, osteoarthritis, rheumatoid arthritis, periodontitis, gingivitis, atherosclerosis, and neoplastic diseases associated with cathepsin K activity.

BRIEF SUMMARY OF THE INVENTION

In a first aspect of the present invention, there is provided a compound of Formula (I):

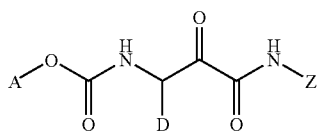

or a salt, solvate, or physiologically functional derivative thereof:

wherein

A is the group defined by $(Q^3)\text{-}(Q^2)_n\text{-}(Q^1)\text{-}(Q)_m\text{-}$, wherein Q is $CH_2$ and m is 0, 1, or 2

$Q^1$ is $C_3$-$C_7$ cycloalkylene;

$Q^2$ is $C_1$-$C_3$ alkylene and n is 0 or 1, or $Q^2$ is OR, where R is $C_1$-$C_3$ alkylene and n is 1, or $Q^2$ is SR, where R is $C_1$-$C_3$ alkylene and n is 1; or $Q^2$ is N(R')R, where R' is hydrogen or $C_1$-$C_6$ alkyl, R is $C_1$-$C_3$ alkylene and n is 1; and $Q^3$ is aryl, heteroaryl, or aryl or heteroaryl substituted with at least one independently selected $R^1$ group;

D is $C_1$-$C_6$ alkyl or $C_1$-$C_6$ alkyl substituted with —$NR^2R^3$;

Z is the group defined by —$(X)_p$—$(X^1)_q$—$(X^2)$, wherein X is C(R')(R''), wherein R' is hydrogen or $C_1$-$C_6$ alkyl, R'' is hydrogen and $C_1$-$C_6$ alkyl, and p is 0, 1, or 2, $X^1$ is $C(O)OCH_2$, wherein q is 0 or 1, and $X^2$ is aryl, heteroaryl, or heterocyclyl;

$R^1$ is halo, $C_1$-$C_6$ alkyl, aryl, heterocyclyl, or $C_1$-$C_6$ haloalkyl;

$R^2$ is hydrogen or $C_1$-$C_6$ alkyl;

$R^3$ is hydrogen, $C_1$-$C_6$ alkyl, —$C(O)R^4$, or —$S(O)_2NR^5R^6$;

$R^4$ is heterocyclyl, —$NR^5R^6$, and $R^5$ and $R^6$ are independently selected from hydrogen or $C_1$-$C_6$ alkyl.

In a second aspect of the present invention, there is provided a pharmaceutical composition comprising: a therapeutically effective amount of a compound of formula (I), or a salt, solvate, or a physiologically functional derivative thereof and one or more of pharmaceutically acceptable carriers, diluents and excipients.

In a third aspect of the present invention, there is provided a method of treating a disorder in a mammal, said disorder being characterized by bone loss, comprising: administering to said mammal a therapeutically effective amount of a compound of formula (I) or a salt, solvate or a physiologically functional derivative thereof.

In a fourth aspect of the present invention, there is provided a compound of formula (I), or a salt, solvate, or a physiologically functional derivative thereof for use in therapy.

In a fifth aspect of the present invention, there is provided the use of a compound of formula (I), or a salt, solvate, or a physiologically functional derivative thereof in the preparation of a medicament for use in the treatment of a disorder characterized by bone loss.

In a sixth aspect of the present invention, there is provided a method of treating osteoporosis comprising: administering to said mammal a therapeutically effective amount of a compound of formula (I), or a salt, solvate or physiologically functional derivative thereof.

In an seventh aspect of the present invention, there is provided a method of treating osteoporosis comprising: administering to said mammal therapeutically effective amounts of (i) a compound of formula (I), or a salt, solvate or physiologically functional derivative thereof and (ii) at least one bone building agent.

DETAILED DESCRIPTION OF THE INVENTION

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the term "lower" refers to a group having between one and six carbons.

As used herein, the term "alkyl" refers to a straight or branched chain hydrocarbon having from one to twelve carbon atoms, optionally substituted with substituents selected from the group consisting of lower alkyl, lower alkoxy, lower alkylsulfanyl, lower alkylsulfenyl, lower alkylsulfonyl, oxo, mercapto, amino optionally substituted by alkyl, carboxy, carbamoyl optionally substituted by alkyl, aminosulfonyl optionally substituted by alkyl, nitro, or lower perfluoroalkyl, multiple degrees of substitution being allowed. Examples of "alkyl" as used herein include, but are not limited to, n-butyl, n-pentyl, isobutyl, isopropyl, and the like.

As used herein, the terms "$C_1$-$C_2$ alkyl" and "$C_1$-$C_6$ alkyl" refer to an alkyl group, as defined above, which contains at least 1, and at most 2 or 6, carbon atoms. Examples of "$C_1$-$C_2$ alkyl" and "$C_1$-$C_6$ alkyl" groups useful in the present invention include, but are not limited to, methyl, ethyl, propyl, isopropyl, isobutyl, n-butyl, tert-butyl, and isopentyl.

As used herein, the term "alkylene" refers to a straight or branched chain divalent hydrocarbon radical having from one to ten carbon atoms, optionally substituted with substituents selected from the group which includes lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen and lower perfluoroalkyl, multiple degrees of substitution being allowed. Examples of "alkylene" as used herein include, but are not limited to, methylene, ethylene, n-propylene, n-butylene, and the like.

As used herein, the terms "$C_1$-$C_3$ alkylene" and "$C_1$-$C_4$ alkylene" refer to an alkylene group, as defined above, which contains at least 1, and at most 3 or 4, carbon atoms respectively. Examples of "$C_1$-$C_3$ alkylene" groups useful in the present invention include, but are not limited to, methylene, ethylene, and n-propylene.

As used herein, the term "halogen" or "halo" refers to fluoro (—F), chloro (—Cl), bromo (—Br), or iodine (—I).

As used herein, the term "haloalkyl" refers to an alkyl group, as defined herein, substituted with at least one halo, halo being as defined herein. Examples of branched or straight chained "haloalkyl" groups useful in the present invention include, but are not limited to, methyl, ethyl, propyl, isopropyl, n-butyl, and t-butyl substituted independently with one or more halogens, e.g., fluoro, chloro, bromo and iodo.

As used herein, the terms "$C_1$-$C_2$ haloalkyl" and "$C_1$-$C_3$ haloalkyl" refer to haloalkyl as defined above containing at least 1, and at most 2 or 3 carbon atoms substituted with at least one halogen, halogen being as defined herein. Examples of branched or straight chained "$C_1$-$C_2$ haloalkyl" and "$C_1$-$C_3$ haloalkyl" groups useful in the present invention include, but are not limited to methyl, ethyl, propyl, and isopropyl, substituted independently with one or more halogens, e.g., fluoro, chloro, bromo, and iodo.

As used herein, the term "$C_3$-$C_7$ cycloalkyl" refers to a non-aromatic cyclic divalent hydrocarbon radical having from three to seven carbon atoms. Exemplary "$C_3$-$C_7$ cycloalkylene" groups include, but are not limited to cyclopropylene, cyclobutylene, cyclopentylene, cyclohexylene, and cycloheptylene.

As used herein, the term "$C_3$-$C_7$ cycloalkylene" refers to a non-aromatic cyclic hydrocarbon ring having from three to seven carbon atoms. Exemplary "$C_3$-$C_7$ cycloalkyl" groups include, but are not limited to cyclopropyl, cyclobutyl, cyclopentyl, cyclohexyl, and cycloheptyl.

As used herein, the term "aryl" refers to an optionally substituted benzene ring or to an optionally substituted benzene ring system fused to one or more optionally substituted benzene rings to form, for example, anthracene, phenanthrene, or napthalene ring systems. Exemplary optional substituents include lower alkyl, $C_3$-$C_7$ cycloalkyl, lower haloalkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl, or aryl, multiple degrees of substitution being allowed. Examples of "aryl" groups include, but are not limited to, phenyl, 2-naphthyl, 1-naphthyl, and biphenyl, as well as substituted derivatives thereof.

As used herein, the term "aralkyl" refers to an aryl or heteroaryl group, as defined herein, attached through a lower alkylene linker, wherein the lower alkylene is as defined herein. Examples of "aralkyl" include, but are not limited to benzyl, phenylpropyl, 2-pyridylmethyl, 3-isoxazolylmethyl, 5-methyl-3-isoxazolylmethyl, and 2-imidazoyly ethyl.

As used herein, the term "arylamino" refers to an aryl or heteroaryl group, as defined herein, attached through an amino group —NR'—, wherein R' is as defined herein.

As used herein, the term "heteroaryl" refers to a monocyclic five to seven membered aromatic ring, or to a fused bicyclic aromatic ring system comprising two of such monocyclic five to seven membered aromatic rings. These heteroaryl rings contain one or more nitrogen, sulfur, and/or oxygen atoms, where N-oxides and sulfur oxides and dioxides are permissible heteroatom substitutions and may be optionally substituted with up to three members selected from a group consisting of lower alkyl, lower haloalkyl, $C_3$-$C_7$ cycloalkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl, or aryl, multiple degrees of substitution being allowed. Examples of "heteroaryl" groups used herein include furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, indazole, and substituted versions thereof.

As used herein, the term "heterocyclic" or the term "heterocyclyl" refers to a three to twelve-membered non-aromatic heterocyclic ring being saturated or having one or more degrees of unsaturation containing one or more heteroatomic substitutions selected from S, S(O), S(O)$_2$, O, or N, optionally substituted with substituents selected from the group consisting of lower alkyl, lower haloalkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one or more of another "heterocyclic" ring(s) or cycloalkyl ring(s). Examples of "heterocyclic" include, but are not limited to, tetrahydrofuran, pyran, 1,4-dioxane, 1,3-dioxane, piperidine, pyrrolidine, morpholine, tetrahydrothiopyran, tetrahydrothiophene, and the like.

As used herein the term "heteroarylalkyl" refers to a heteroaryl group as described above substituted with an alkyl group containing the specified number of carbon atoms. The "heteroarylalkyl" group may be optionally substituted with up to three members selected from a group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, nitro, cyano, halogen, lower perfluoroalkyl, heteroaryl, or aryl, multiple degrees of substitution being allowed. An example of a "heteroarylalkyl" as used herein includes, but is not limited to, 4-pyridinylmethyl.

As used herein, the term "alkoxy" refers to the group $R_aO$—, where $R_a$ is alkyl as defined above and the term "$C_1$-$C_2$ alkoxy" refers to the group $R_aO$—, where $R_a$ is $C_1$-$C_2$ alkyl.

As used herein, the term "haloalkoxy" refers to the group $R_aO$—, where $R_a$ is haloalkyl as defined above and the term "$C_1$-$C_2$ haloalkoxy" refers to the group $R_aO$—, where $R_a$ is $C_1$-$C_2$ haloalkyl as defined above.

As used herein the term "aralkoxy" refers to the group $R_bR_aO$—, where $R_a$ is alkylene and $R_b$ is aryl, both as defined above.

As used herein, the term "alkylsulfanyl" refers to the group $R_aS$—, where $R_a$ is alkyl as defined above.

As used herein, the term "alkylsulfenyl" refers to the group $R_aS(O)$—, where $R_a$ is alkyl as defined above.

As used herein, the term "alkylsulfonyl" refers to the group $R_aS(O)_2$—, where $R_a$ is alkyl as defined above.

As used herein, the term "oxo" refers to the group =O

As used herein, the term "mercapto" refers to the group —SH.

As used herein, the term "carboxy" refers to the group —COOH.

As used herein, the term "cyano" refers to the group —CN.

As used herein the term "cyanoalkyl" refers to the group —$R_aCN$ wherein $R_a$ is $C_1$-$C_3$ alkylene as defined above. Exemplary "cyanoalkyl" groups useful in the present invention include, but are not limited to cyanomethyl, cyanoethyl, and cyanopropyl.

As used herein, the term "aminosulfonyl" refers to the group —$S(O)_2NH_2$.

As used herein, the term "carbamoyl" refers to the group —$C(O)NH_2$.

As used herein, the term "sulfanyl" shall refer to the group —S—.

As used herein, the term "sulfenyl" shall refer to the group —S(O)—.

As used herein, the term "sulfonyl" shall refer to the group —$S(O)_2$—.

As used herein, the term "acyl" refers to the group $R_aC(O)$—, where $R_a$ is alkyl, cycloalkyl, or heterocyclyl as defined herein.

As used herein, the term "aroyl" refers to the group $R_aC(O)$—, where $R_a$ is aryl as defined herein.

As used herein, the term "heteroaroyl" refers to the group $R_aC(O)$—, where $R_a$ is heteroaryl as defined herein.

As used herein, the term "alkoxycarbonyl" refers to the group $R_aOC(O)$—, where $R_a$ is alkyl as defined herein.

As used herein, the term "acyloxy" refers to the group $R_aC(O)O$—, where $R_a$ is alkyl, cycloalkyl, or heterocyclyl as defined herein.

As used herein, the term "aroyloxy" refers to the group $R_aC(O)O$—, where $R_a$ is aryl as defined herein.

As used herein, the term "heteroaroyloxy" refers to the group $R_aC(O)O$—, where $R_a$ is heteroaryl as defined herein.

As used herein, the term "optionally" means that the subsequently described event(s) may or may not occur, and includes both event(s) that occur, and events that do not occur.

As used herein, the term "physiologically functional derivative" refers to any pharmaceutically acceptable derivative of a compound of the present invention; for example, an ester or an amide, which upon administration to a mammal is capable of providing (directly for indirectly) a compound of the present invention or an active metabolite thereof. Such derivatives are clear to those skilled in the art, without undue experimentation, and with reference to the teaching of Burger's Medicinal Chemistry And Drug Discovery, 5$^{th}$ Edition, Vol 1: Principles and Practice, which is incorporated herein by reference to the extent that it teaches physiologically functional derivatives.

As used herein, the term "solvate" refers to a complex of variable stoichiometry formed by a solute (in this invention, a compound of formula (I)), or a salt or physiologically functional derivative thereof) and a solvent Such solvents for the purpose of the invention may not interfere with the biological activity of the solute. Examples of suitable solvents include, but are not limited to water, methanol, ethanol, and acetic acid. Preferably the solvent used is a pharmaceutically acceptable solvent. Examples of suitable pharmaceutically acceptable solvents include water, ethanol, and acetic acid. Most preferably the solvent used is water.

The compounds of formula (I) have the ability to crystallize in more than one form, a characteristic known as polymorphism, and it is understood that such polymorphic forms ("polymorphs") are within the scope of formula (I). Polymorphism generally can occur as a response to changes in temperature or pressure or both and can also result from variations in the crystallization process. Polymorphs can be distinguished by various physical characteristics known in the art, such as x-ray diffraction patterns, solubility, and melting point.

As used herein, the term "substituted" refers to substitution with the named substituent or substituents, multiple degrees of substitution being allowed unless otherwise stated.

Certain of the compounds described herein may contain one or more chiral centers, or may otherwise be capable of existing as multiple stereoisomers. The compounds of this invention include mixtures of stereoisomers as well as purified enantiomers or enantiomerically or diastereomerically enriched mixtures. Also included within the scope of the invention are the individual isomers of the compounds represented by formula (I) above as well as any wholly or partially equilibrated mixtures thereof. The present invention also covers the individual isomers of the compounds represented by the formulas above as mixtures with isomers thereof in which one or more chiral centers are inverted.

It is to be understood that the following embodiments refer to compounds within the scope of formula (I) as defined above unless specifically limited by the definition of the formula or specifically limited otherwise. It is also understood that the embodiments of the present invention described herein, including uses and compositions, are applicable to formula (I).

As recited above A is the group defined by $(Q^3)$—$(Q^2)_n$—$(Q^1)$—$(Q)_m$—. In one embodiment, n is 0 and A is $(Q^3)$—$(Q^1)$—$(Q)_m$—. In another embodiment, m is 0 and A is $(Q^3)$—$(Q^2)_n$—$(Q^1)$—. In a further embodiment, m and n are both 0 and A is $(Q^3)$—$(Q^1)$—.

In one embodiment, Q is $CH_2$ and m is 0, 1, or 2, preferably m is 0 or 1, more preferably m is 1.

In one embodiment $Q^1$ is $C_3$-$C_7$ cycloalkylene. In a preferred embodiment $Q^1$ is selected from the group cyclobutylene, cyclopentylene or cyclohexylene, preferably cyclobutylene.

In one embodiment, $Q^2$ is $C_1$-$C_3$ alkylene and n is 0 or 1, preferably n is 1. In another embodiment, $Q^2$ is OR, wherein R is $C_1$-$C_3$ alkylene and n is 1. In a further embodiment, $Q^2$ is SR, wherein R is $C_1$-$C_3$ alkylene and n is 1. In an additional embodiment, $Q^2$ is N(R')R, where R' is hydrogen or $C_1$-$C_6$ alkyl, R is $C_1$-$C_3$ alkylene and n is 1.

In one embodiment $Q^3$ is aryl or aryl substituted with at least one independently selected $R^1$ group. In a preferred embodiment, $Q^3$ is phenyl or phenyl substituted with at least one independently selected $R^1$ group wherein $R^1$ is halo, preferably fluoro or chloro, or $C_1$-$C_6$ alkyl, preferably methyl.

In one embodiment $Q^3$ is heteroaryl or heteroaryl substituted with at least one independently selected $R^1$. In a preferred embodiment $Q^3$ is selected from the group

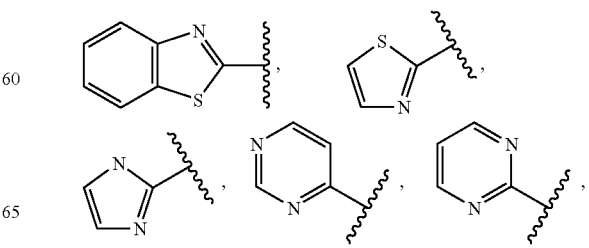

-continued

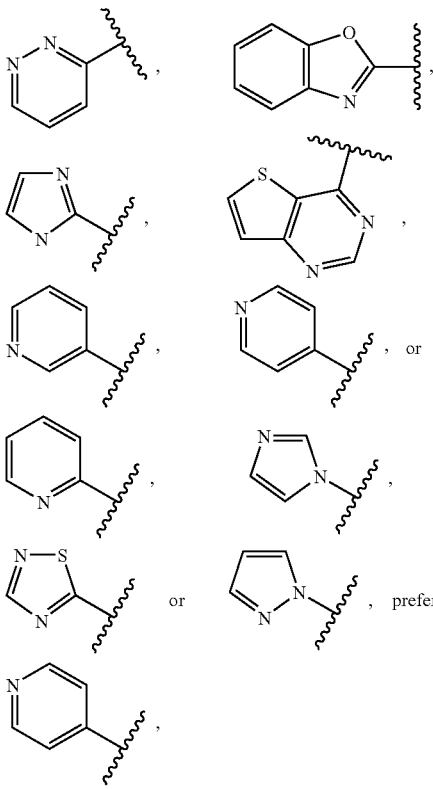

wherein such heteroaryl group is substituted with at least one independently selected $R^1$, wherein $R^1$ is halo, preferably chloro, $C_1$-$C_6$ alkyl, preferably methyl, aryl, preferably phenyl, heterocyclyl, preferably piperazinyl or morpholinyl, or $C_1$-$C_6$ haloalkyl, preferably trifluoromethyl.

It is understood that $Q^3$ as well as $X^2$ below are attached to the indicated linking group of Formula (I) through the bond of $Q^3$ and $X^2$ having an unfilled valence and being indicated by

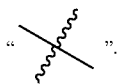

The appropriate attachments are further illustrated in the working examples recited below.

In one embodiment, D is $C_1$-$C_6$ alkyl or $C_1$-$C_6$ alkyl substituted with —$NR^2R^3$, wherein $R^2$ is hydrogen and $R^3$ is —$C(O)R^4$ or —$S(O)_2NR^5R^6$. In a preferred embodiment, D is $C_1$-$C_6$ alkyl. In a more preferred embodiment, D is n-butyl.

As recited above Z is the group defined by —$(X)_p$—$(X^1)_q$—$(X^2)$. In one embodiment, p is 0 and Z is —$(X^1)_q$—$X^2$. In another embodiment, p is 1 and Z is the group defined by —(X)—$(X^1)_q$—$X^2$. In another embodiment, q is 0 and Z is the group defined by —$(X)_p$—$X^2$.

In one embodiment, X is C(R')(R''), wherein R' is hydrogen or $C_1$-$C_6$ alkyl, R'' is hydrogen and $C_1$-$C_6$ alkyl, and p is 0, 1, or 2. In another embodiment, X is C(H)(R'') where R'' is hydrogen and p is 0, 1, or 2, preferably p is 0 or 1, more preferably p is 0. In a preferred embodiment, X is C(H)(R'') where R'' is —$CH_3$ and p is 1.

In one embodiment, $X^1$ is C(O)$OCH_2$, wherein q is 1. In a preferred embodiment, $X^1$ is C(O)$OCH_2$, wherein q is 0.

In one embodiment, $X^2$ is aryl. In a preferred embodiment $X^2$ is

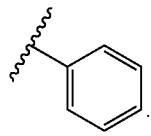

In one embodiment $X^2$ is heteroaryl or heterocyclyl. In a preferred embodiment $X^2$ is selected from the group

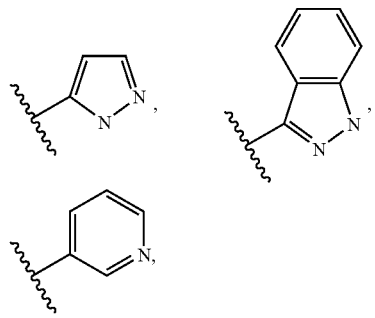

or substituted derivatives thereof.

Specific examples of compounds of the present invention include the following:

1-benzylcyclobutyl(1S)-1-(oxo{[(1R)-1-phenylethyl]amino}acetyl)pentylcarbamate;

1-benzylcyclopentyl(1S)-1-(oxo{[(1R)-1-phenylethyl]amino}acetyl)pentylcarbamate;

benzyl(2S)-2-{[(3S)-3-({[(1-benzylcyclopentyl)oxy]carbonyl}amino)-2-oxoheptanoyl]amino}propanoate;

1-benzylcyclohexyl(1S)-1-(oxo{[(1R)-1-phenylethyl]amino}acetyl)pentylcarbamate;

(1-Benzylcyclobutyl)methyl(1S)-1-(oxo{[(1R)-1-phenylethyl]amino}acetyl) pentyl carbamate;

[1-(2-Phenylethyl)cyclobutyl]methyl(1S)-1-(oxo{[(1R)-1-phenylethyl]amino}acetyl) pentylcarbamate;

[1-(3-Phenylpropyl)cyclobutyl]methyl(1S)-1-(oxo{[(1R)-1-phenylethyl]amino}acetyl) pentylcarbamate;

(1-Benzylcyclopentyl)methyl(1S)-1-(oxo{[(1R)-1-phenylethyl]amino}acetyl)pentylcarbamate;

(1-benzylcyclohexyl)methyl(1S)-5-[(4-morpholinylcarbonyl)amino]-1-(oxo{[(1R)-1-phenylethyl]amino}acetyl)pentylcarbamate;

[1-(4-Fluorobenzyl)cyclobutyl]methyl(1S)-5-[(4-morpholinylcarbonyl)amino]-1-(oxo{[(1R)-1-phenylethyl]amino}acetyl)pentylcarbamate;

[1-(4-Pyridinylmethyl)cyclobutyl]methyl(1S)-5-[(4-morpholinylcarbonyl)amino]-1-(oxo{[(1R)-1-phenylethyl]amino}acetyl)pentylcarbamate;

[1-(3-pyridinylmethyl)cyclobutyl]methyl(1S)-5-[(4-morpholinylcarbonyl)amino]-1-(oxo{[(1R)-1-phenylethyl]amino}acetyl)pentylcarbamate;

[1-(2,6-difluorobenzyl)cyclobutyl]methyl(1S)-5-{[(methylamino)carbonyl]amino}1-(oxo{[(1R)-1-phenylethyl]amino}acetyl)pentylcarbamate;

[1-(4-Fluorobenzyl)cyclobutyl]methyl(1S)-1-[oxo(1H-pyrazol-5-ylamino)acetyl]pentylcarbamate;

[1-(4-fluorobenzyl)cyclobutyl]methyl(1S)-1-[[(6-chloro-1H-indazol-3-yl)amino](oxo)acetyl]pentylcarbamate;

[1-(4-fluorobenzyl)cyclobutyl]methyl(1S)-5-{[(dimethylamino)sulfonyl]amino}-1-{oxo[(3-pyridinylmethyl)amino]acetyl}pentylcarbamate;

1-(1,3-Benzothiazol-2-yl)cyclopentyl(1S)-1-[oxo(1H-pyrazol-3-ylamino)acetyl]pentylcarbamate;

{1-[(4-phenyl-1,3-thiazol-2-yl)methyl]cyclobutyl}methyl(1S)-1-(oxo{[(1R)-1-phenylethyl]amino}acetyl)pentylcarbamate;

(1-{[(1-methyl-1H-imidazol-2-yl)sulfanyl]methyl}cyclobutyl)methyl(1S)-1-(oxo{[(1R)-1-phenylethyl]amino}acetyl)pentylcarbamate;

(1-{[(2-chloro-4-pyrimidinyl)oxy]methyl}cyclobutyl)methyl(1S)-1-(oxo{[(1R)-1-phenylethyl]amino}acetyl)pentylcarbamate;

[1-({[2-(4-methyl-1-piperazinyl)-4-pyrimidinyl]oxy}methyl)cyclobutyl]methyl(1S)-1-(oxo{[(1R)-1-phenylethyl]amino}acetyl)pentylcarbamate;

[1-({[2-(4-morpholinyl)-4-pyrimidinyl]oxy}methyl)cyclobutyl]methyl(1S)-1-(oxo{[(1R)-1-phenylethyl]amino}acetyl)pentylcarbamate;

{1-[(2-pyrimidinylsulfanyl)methyl]cyclobutyl}methyl(1S)-1-(oxo{[(1R)-1-phenylethyl]amino}acetyl)pentylcarbamate;

{1-[(1,3-benzoxazol-2-ylsulfanyl)methyl]cyclobutyl}methyl(1S)-1-(oxo{[(1R)-1-phenylethyl]amino}acetyl)pentylcarbamate;

{1-[(1,3-thiazol-2-yloxy)methyl]cyclobutyl}methyl(1S)-1-(oxo{[(1R)-1-phenylethyl]amino}acetyl)pentylcarbamate;

(1-{[(3-phenyl-1,2,4-thiadiazol-5-yl)oxy]methyl}cyclobutyl)methyl(1S)-1-(oxo{[(1R)-1-phenylethyl]amino}acetyl)pentylcarbamate;

[1-({[2-(4-phenyl-1-piperazinyl)-4-pyrimidinyl]oxy}methyl)cyclobutyl]methyl(1S)-1-(oxo{[(1R)-1-phenylethyl]amino}acetyl)pentylcarbamate;

(1-{[(1-phenyl-1H-imidazol-2-yl)sulfanyl]methyl}cyclobutyl)methyl(1S)-1-(oxo{[(1R)-1-phenylethyl]amino}acetyl)pentylcarbamate;

{1-[(thieno[3,2-d]pyrimidin-4-yloxy)methyl]cyclobutyl}methyl(1S)-1-(oxo{[(1R)-1-phenylethyl]amino}acetyl)pentylcarbamate;

{1-[(2-pyrimidinyloxy)methyl]cyclobutyl}methyl(1S)-1-(oxo{[(1R)-1-phenylethyl]amino}acetyl)pentylcarbamate;

[1-({[4-(4-methylphenyl)-1,3-thiazol-2-yl]oxy}methyl)cyclobutyl]methyl(1S)-1-(oxo{[(1R)-1-phenylethyl]amino}acetyl)pentylcarbamate;

[1-(hydroxymethyl)cyclobutyl]methyl(1S)-1-(oxo{[(1R)-1-phenylethyl]amino}acetyl)pentylcarbamate;

[1-({[4-(4-chlorophenyl)-2-pyrimidinyl]sulfanyl}methyl)cyclobutyl]methyl(1S)-1-(oxo{[(1R)-1-phenylethyl]amino}acetyl)pentylcarbamate;

[1-({[5-(4-chlorophenyl)-1-methyl-1H-imidazol-2-yl]sulfanyl}methyl)cyclobutyl]methyl(1S)-1-(oxo{[(1R)-1-phenylethyl]amino}acetyl)pentylcarbamate;

{1-[(4-methyl-1,3-thiazol-2-yl)methyl]cyclobutyl}methyl(1S)-1-(oxo{[(1R)-1-phenylethyl]amino}acetyl)pentylcarbamate;

(1-{2-[(1-methyl-1H-imidazol-2-yl)sulfanyl]ethyl}cyclobutyl)methyl(1S)-1-(oxo{[(1R)-1-phenylethyl]amino}acetyl)pentylcarbamate;

(1-{3-[(1-methyl-1H-imidazol-2-yl)sulfanyl]propyl}cyclobutyl)methyl(1S)-1-(oxo{[(1R)-1-phenylethyl]amino}acetyl)pentylcarbamate; and (1-{3-[(2-chloro-4-pyrimidinyl)oxy]propyl}cyclobutyl)methyl(1S)-1-(oxo{[(1R)-1-phenylethyl]amino}acetyl)pentylcarbamate;

or a salt, solvate, or physiologically functional derivative thereof.

Typically, the salts of the present invention are pharmaceutically acceptable salts. Salts encompassed within the term "pharmaceutically acceptable salts" refer to non-toxic salts of the compounds of this invention. Salts of the compounds of the present invention may comprise acid addition salts derived from a nitrogen on a substituent in the compound of formula (I). Representative salts include the following salts: acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, laurate, malate, maleate, mandelate, mesylate, methylbromide, methylnitrate, methylsulfate, monopotassium maleate, mucate, napsylate, nitrate, N-methylglucamine, oxalate, pamoate (embonate), palmitate, pantothenate, phosphate/diphosphate, polygalacturonate, potassium, salicylate, sodium, stearate, subacetate, succinate, tannate, tartrate, teoclate, tosylate, triethiodide, trimethylammonium, and valerate. Other salts, which are not pharmaceutically acceptable, may be useful in the preparation of compounds of this invention and these form a further aspect of the invention.

While it is possible that, for use in therapy, therapeutically effective amounts of a compound of formula (I), as well as salts, solvates and physiological functional derivatives thereof, may be administered as the raw chemical, it is possible to present the active ingredient as a pharmaceutical composition. Accordingly, the invention further provides pharmaceutical compositions, which include therapeutically effective amounts of compounds of the formula (I) and salts, solvates and physiological functional derivatives thereof, and one or more pharmaceutically acceptable carriers, diluents, or excipients. The compounds of the formula (I) and salts, solvates and physiological functional derivatives thereof, are as described above. The carrier(s), diluent(s) or excipient(s) must be acceptable in the sense of being compatible with the other ingredients of the formulation and not deleterious to the recipient thereof. In accordance with another aspect of the invention there is also provided a process for the preparation of a pharmaceutical formulation including admixing a compound of the formula (I), or salts, solvates and physiological functional derivatives thereof, with one or more pharmaceutically acceptable carriers, diluents or excipients.

Pharmaceutical formulations may be presented in unit dose forms containing a predetermined amount of active ingredient per unit dose. Such a unit may contain, for example, 0.5 mg to 1 g, preferably 1 mg to 700 mg, of a compound of the formula (I) depending on the condition being treated, the route of administration and the age, weight and condition of the patient. Preferred unit dosage formulations are those containing a daily dose or sub-dose, as herein above recited, or an appropriate fraction thereof, of an active ingredient. Furthermore, such pharmaceutical formulations may be prepared by any of the methods well known in the pharmacy art.

Pharmaceutical formulations may be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing and coloring agent can also be present.

Capsules are made by preparing a powder mixture as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant, and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials, and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids such as solution, syrups and elixirs can be prepared in dosage unit form so that a given quantity contains a predetermined amount of the compound. Syrups can be prepared by dissolving the compound in a suitably flavored aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives; flavor additives such as peppermint oil, or natural sweeteners, saccharin, or other artificial sweeteners; and the like can also be added.

Where appropriate, dosage unit formulations for oral administration can be microencapsulated. The formulation can also be prepared to prolong or sustain the release as for example by coating or embedding particulate material in polymers, wax or the like.

The compounds of formula (I) and salts, solvates and physiological functional derivatives thereof, can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds of formula (I) and salts, solvates and physiologically functional derivatives thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds may be coupled to a class of biodegradable polymers useful in achieving controlled release of a drug; for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a coarse powder having a particle size for example in the range 20 to 500 microns, which is administered in the manner in which snuff is taken, i.e., by rapid inhalation through the nasal passage from a container of the powder held close up to the nose. Suitable formulations wherein the carrier is a liquid, for administration as a nasal spray or as nasal drops, include aqueous or oil solutions of the active ingredient.

Pharmaceutical formulations adapted for administration by inhalation include fine particle dusts or mists, which may be generated by means of various types of metered, dose pressurised aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and solutes that render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavouring agents.

A therapeutically effective amount of a compound of the present invention will depend upon a number of factors including, for example, the age and weight of the animal, the precise condition requiring treatment and its severity, the nature of the formulation, and the route of administration, and will ultimately be at the discretion of the attendant physician or veterinarian. However, an effective amount of a compound of formula (I) for the treatment of osteoporosis will generally be in the range of 0.1 to 100 mg/kg body weight of recipient (mammal) per day and more usually in the range of 1 to 10 mg/kg body weight per day. Thus, for a 70 kg adult mammal, the actual amount per day would usually be from 70 to 700 mg and this amount may be given in a single dose per day or more usually in a number (such as two, three, four, five or six) of sub-doses per day such that the total daily dose is the same. An effective amount of a salt or solvate, or physiologically functional derivative thereof, may be determined as a proportion of the effective amount of the compound of formula (I) per se. It is envisaged that similar dosages would be appropriate for treatment of the other conditions referred to above.

The compounds of the present invention and their salts and solvates, and physiologically functional derivatives thereof, may be employed alone or in combination with other therapeutic agents for the treatment of the above-mentioned conditions. In particular, in osteoporosis therapy, combination with other osteoporosis therapeutic agents is envisaged. Combination therapies according to the present invention thus comprise the administration of at least one compound of formula (I) or a pharmaceutically acceptable salt or solvate thereof, or a physiologically functional derivative thereof, and the use of at least one other osteoporosis treatment method. Preferably, combination therapies according to the present invention comprise the administration of at least one compound of formula (I) or a pharmaceutically acceptable salt or solvate thereof, or a physiologically functional derivative thereof, and at least one other osteoporosis treatment agent, preferably a bone building agent, such as parathyroid hormone. The compound(s) of formula (I) and the other pharmaceutically active agent(s) may be administered together or separately and, when administered separately, this may occur simultaneously or sequentially in any order. The amounts of the compound(s) of formula (I) and the other pharmaceutically active agent(s) and the relative timings of administration will be selected in order to achieve the desired combined therapeutic effect The administration in combination of a compound of formula (I) or salts, solvates, or physiologically functional derivatives thereof with other osteoporosis treatment agents may be in combination in accordance with the invention by administration concomitantly in (1) a unitary pharmaceutical composition including both compounds or (2) separate pharmaceutical compositions each including one of the compounds. Alternatively, the combination may be administered separately in a sequential manner wherein one osteoporosis treatment agent is administered first and the other second or vice versa. Such sequential administration may be close in time or remote in time.

A preferred additional osteoporosis treatment agent is a bone building (anabolic) agent such as parathyroid hormone. Bone building agents can lead to increases in parameters such as bone mineral density greater than those than can be achieved with anti-resorptive agents. In some cases, such anabolic agents can increase trabecular connectivity leading to greater structural integrity of the bone. A combination therapy composed of a bone forming agent with an anti-resorptive drug such as a cathepsin K inhibitor could provide even greater efficacy than treatment with either agent alone.

The present invention is directed to methods of regulating, modulating, or inhibiting cathepsin K for the prevention and/or treatment of disorders related to enhanced bone turnover, which can ultimately lead to fracture. In particular, the compounds of the present invention can also be used in the treatment of osteoporosis. Furthermore, the compounds of the present invention can be used to provide additive or synergistic effects with existing osteoporosis therapies.

The present invention thus also provides compounds of formula (I) and pharmaceutically acceptable salts or solvates thereof, or physiologically functional derivatives thereof, for use in medical therapy, and particularly in the treatment of disorders mediated by enhanced bone turnover which can ultimately leading to fracture.

The present invention also provides compounds of formula (I) and pharmaceutically acceptable salts or solvates thereof, or physiologically functional derivatives thereof, for use in medical therapy, and particularly in the treatment of disorders characterized by bone loss or characterized by excessive cartilage or matrix degradation.

The compounds of the present invention are also useful in the treatment of one or more diseases afflicting mammals that are characterized by potential involvement of cathepsin K in autoimmune diseases such as rheumatoid arthritis, osteoathritis, neoplastic disdeases, parasitic diseases, and atherosclerosisis.

A further aspect of the invention provides a method of treatment of a mammal suffering from a disorder mediated by enhanced bone turnover that can ultimately lead to fracture, which includes administering to said subject an effective amount of a compound of formula (I) or a pharmaceutically acceptable salt, solvate, or a physiologically functional derivative thereof.

A further aspect of the invention provides a method of treatment of a mammal suffering from a disorder characterized by bone loss, which includes administering to said subject an effective amount of a compound of formula (I) or a pharmaceutically acceptable salt, solvate, or a physiologically functional derivative thereof. In a preferred embodiment, the disorder is osteoporosis.

A further aspect of the invention provides a method of treatment of a mammal suffering from osteoporosis, which includes administering to said subject an effective amount of a compound of formula (I) or a pharmaceutically acceptable salt or solvate thereof, or a physiologically functional derivative thereof.

A further aspect of the present invention provides the use of a compound of formula (I), or a pharmaceutically acceptable salt or solvate thereof, or a physiologically functional derivative thereof, in the preparation of a medicament for the treatment of a disorder characterized by enhanced bone turnover that can ultimately lead to fracture. In a preferred embodiment, the disorder is osteoporosis.

A further aspect of the present invention provides the use of a compound of formula (I), or a pharmaceutically acceptable salt or solvate thereof, or a physiologically functional derivative thereof, in the preparation of a medicament for the treatment of a disorder characterized by bone loss. In a preferred embodiment, the disorder is osteoporosis.

A further aspect of the present invention provides the use of a compound of formula (I), or a pharmaceutically acceptable salt or solvate thereof, or a physiologically functional derivative thereof, in the preparation of a medicament for the treatment of osteoporosis.

The mammal requiring treatment with a compound of the present invention is typically a human being.

In another embodiment, therapeutically effective amounts of the compounds of formula (I) or salts, solvates or physiologically derived derivatives thereof and at least one bone building agent may be administered in combination to a mammal for treatment of osteoporosis.

The compounds of this invention may be made by a variety of methods, including standard synthetic methods. Any previously defined variable will continue to have the previously defined meaning unless otherwise indicated. Illustrative general synthetic methods are set out below and then specific compounds of the invention are prepared in the working Examples.

Compounds of general formula (I) may be prepared by methods known in the art of organic synthesis as set forth in part by the following synthetic schemes. It is also recognized that in all of the schemes described below, it is well understood that protecting groups for sensitive or reactive groups are employed where necessary in accordance with general principles of synthetic chemistry. Protecting groups are manipulated according to standard methods of organic synthesis (T. W. Green and P. G. M. Wuts (1991) *Protecting Groups in Organic Synthesis*, John Wiley & Sons). These groups are removed at a convenient stage of the compound synthesis using methods that are readily apparent to those skilled in the art. The selection of processes as well as the reaction conditions and order of their execution shall be consistent with the preparation of compounds of formula (I). Those skilled in the art will recognize if a stereocenter exists in compounds of formula (I). Accordingly, the present invention includes all possible stereoisomers and includes not only racemic compounds but the individual enantiomers as well. When a compound is desired as a single enantiomer, it may be obtained by stereospecific synthesis or by resolution of the final product or any convenient intermediate. Resolution of the final product, an intermediate, or a starting material may be effected by any suitable method known in the art. See, for example, *Stereochemistry of Organic Compounds* by E. L. Eliel, S. H. Wilen, and L. N. Mander (Wiley-Interscience, 1994).

Compounds of formula (I), can be prepared according to the synthetic sequences shown in Schemes I, II, and III which are further detailed in the Examples section following.

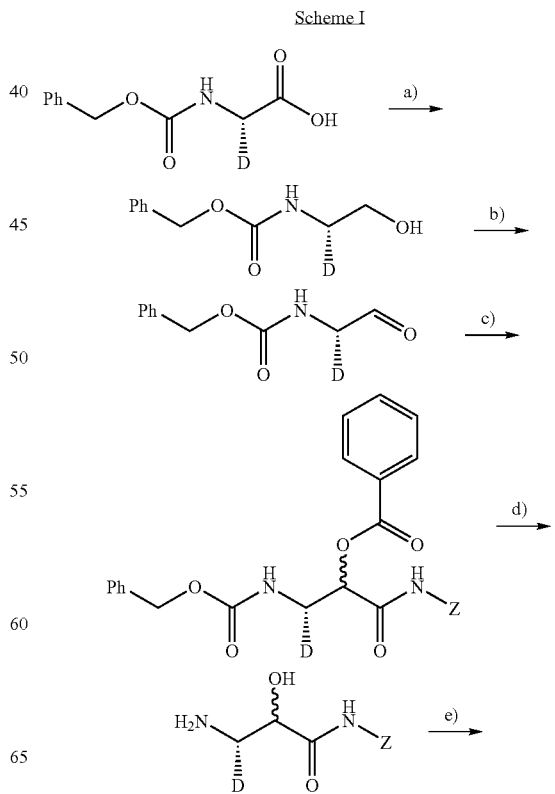

Scheme I

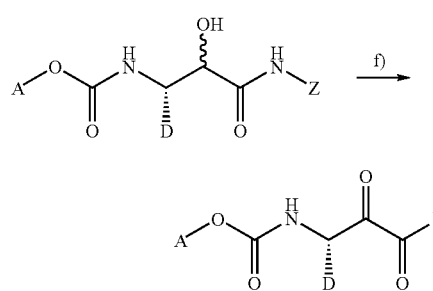
a) iPrOCOCl, NEt₃, THF, 0° C., NaBH₄, THF, H₂O, 0° C. to rt;
b) pyridine•SO₃, NEt₃, DMSO, CH₂Cl₂, -10° C. to rt;
c) isonitrile, PhCOOH, CH₂Cl₂;
d) NaOH, dioxane, H₂O, 100° C.;
e) chloroformate, THF, iPr₂NEt;
f) Dess-Martin Periodinane, Swern, or TEMPO oxidation.
Scheme II
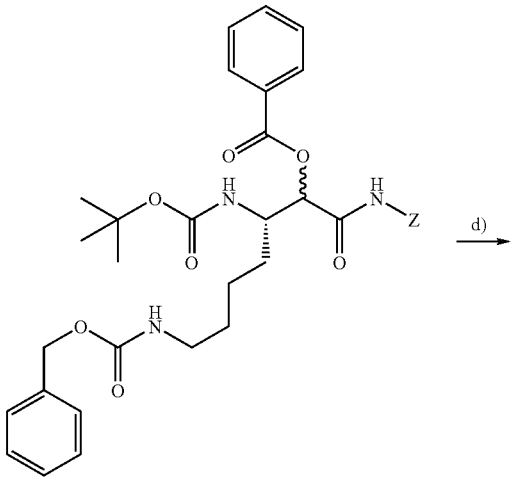
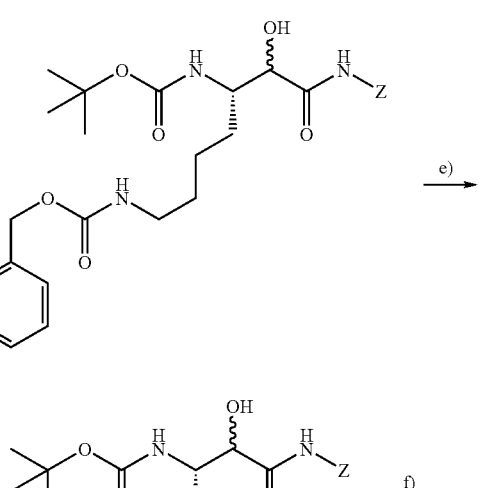
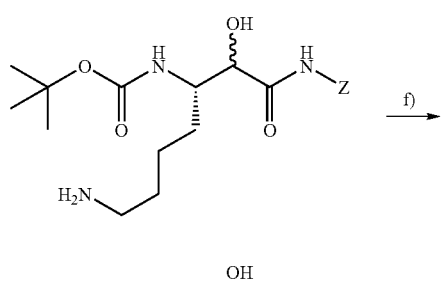
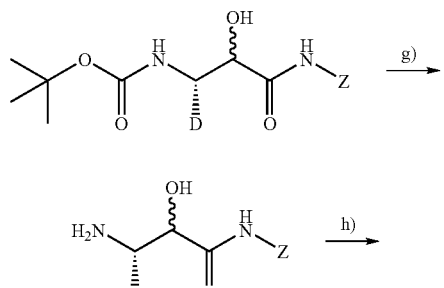
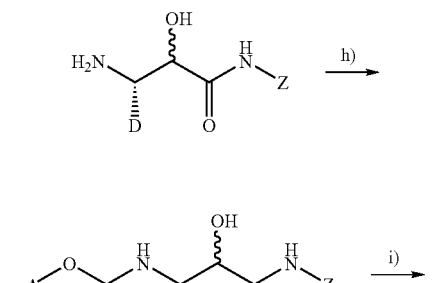
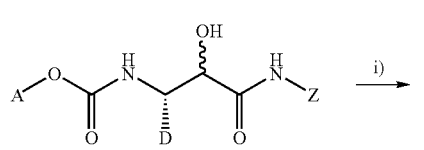

-continued

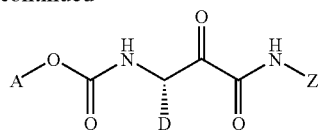

a) iPrOCOCl, NEt₃, THF, 0° C., NaBH₄, THF, H₂O, 0° C. to rt;
b) pyridine•SO₃, NEt₃, DMSO, CH₂Cl₂, -10° C. to rt;
c) isonitrile, PhCOOH, CH₂Cl₂;
d) LiOH•H₂O, THF, H₂O, 1N HCl;
e) H₂, 10% Pd/C, ethanol;
f) isocyanate, dioxane, NEt₃; or sulfonyl chloride, THF, iPr₂Net;
g) 4N HCl in dioxane, dioxane;
h) chloroformate, THF, iPr₂NEt;
i) Dess-Martin Periodinane, Swern, or TEMPO oxidation.

Scheme III

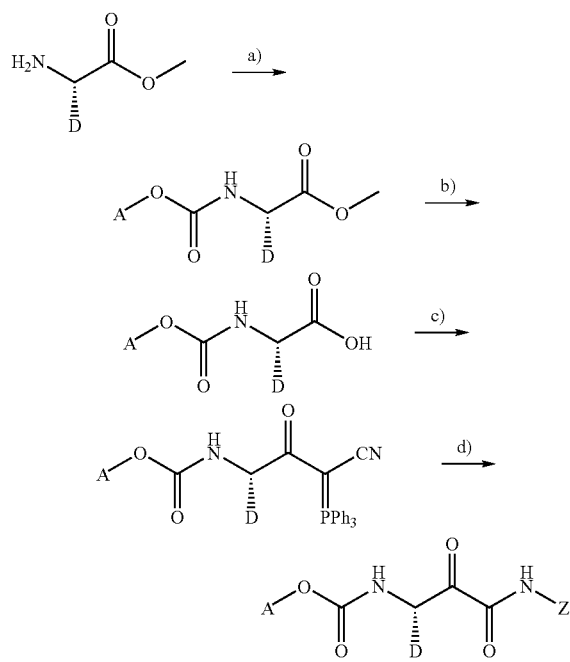

a) chloroformate, THF, NEt₃;
b) LiOH•H₂O, THF, H₂O, 1N HCl;
c) Ph₃P=CCN, EDC, DMAP, CH₂Cl₂;
d) O₃, CH₂Cl₂, -78° C.; N₂; amine, THF; AgNO₃, THF, H₂O.

Certain embodiments of the present invention will now be illustrated by way of example only. The physical data given for the compounds exemplified is consistent with the assigned structure of those compounds.

EXAMPLES

As used herein the symbols and conventions used in these processes, schemes and examples are consistent with those used in the contemporary scientific literature, for example, the *Journal of the American Chemical Society* or the *Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

g (grams); mg (milligrams);
L (liters); mL (milliliters);
μL (microliters); psi (pounds per square inch);
M (molar); mM (millimolar);
h (hour(s)); Hz (Hertz);
MHz (megahertz); mol (moles);
mmol (millimoles); RT (room temperature);
min (minutes); d (day(s));
mp (melting point); TLC (thin layer chromatography);
$T_r$ (retention time); RP (reverse phase);
MeOH (methanol); i-PrOH (isopropanol);
TEA (triethylamine); TFA (trifluoroacetic acid);
TFAA (trifluoroacetic anhydride); THF (tetrahydrofuran);
DMSO (dimethylsulfoxide); EtOAc (ethyl acetate);
DME (1,2-dimethoxyethane); DCM (dichloromethane);
DCE (dichloroethane); DMF (N,N-dimethylformamide);
DMPU (N,N'-dimethylpropyleneurea); CDI (1,1-carbonyldiimidazole);
IBCF (isobutyl chloroformate); HOAc (acetic acid);
HOSu (N-hydroxysuccinimide); HOBT (1-hydroxybenzotriazole);
mCPBA (meta-chloroperbenzoic acid; EDC (ethylcarbodiimide hydrochloride);
BOC (tert-butyloxycarbonyl); FMOC (9-fluorenylmethoxycarbonyl);
DCC (dicyclohexylcarbodiimide); CBZ (benzyloxycarbonyl);
Ac (acetyl); atm (atmosphere);
TMSE (2-(trimethylsilyl)ethyl); TMS (trimethylsilyl);
TIPS (triisopropylsilyl); TBS (t-butyldimethylsilyl);
DMAP (4-dimethylaminopyridine); Me (methyl);
HPLC (high pressure liquid chromatography);
BOP (bis(2-oxo-3-oxazolidinyl)phosphinic chloride);
TBAF (tetra-n-butylammonium fluoride);
Et (ethyl); tBu (tert-butyl).

All references to ether are to diethyl ether; brine refers to a saturated aqueous solution of NaCl. Unless otherwise indicated, all temperatures are expressed in ° C. (degrees Centigrade). All reactions were conducted under an inert atmosphere at room temperature unless otherwise noted.

¹H NMR spectra were recorded on a Varian VXR-300, a Varian Unity-300, a Varian Unity-400 instrument, or a General Electric QE-300. Chemical shifts are expressed in parts per million (ppm, δ units). Coupling constants are in units of hertz (Hz). Splitting patterns describe apparent multiplicities and are designated as s (singlet), d (doublet), t (triplet), q (quartet), qnt (quintet), m (multiplet), br (broad).

Low-resolution mass spectra (MS) were recorded on a JOEL JMS-AX505HA, JOEL SX-102, or a SCIEX-APIiii spectrometer; high resolution MS were obtained using a JOEL SX-102A spectrometer. All mass spectra were taken under electrospray ionization (ESI), chemical ionization (CI), electron impact (EI) or by fast atom bombardment (FAB) methods. Infrared (IR) spectra were obtained on a Nicolet 510 FT-IR spectrometer using a 1-mm NaCl cell. All reactions were monitored by thin-layer chromatography on 0.25 mm E. Merck silica gel plates (60F-254), visualized with UV light, 5% ethanolic phosphomolybdic acid, iodine, iodoplatinate(potassium), permanganate(potassium), or p-anisaldehyde solution. Flash column chromatography was performed on silica gel (230-400 mesh, Merck). Optical rotations were obtained using a Perkin Elmer Model 241 Polarimeter. Melting points were determined using a Mel-Temp II apparatus and are uncorrected.

The following examples describe the syntheses of compounds of Formula (I) and (II) as well as intermediates particularly useful in the synthesis of compounds of Formula (I) and (II):

Example 1

1-Benzylcyclobutyl (1S)-1-(oxo{[(1R)-1-phenylethyl]amino}acetyl)pentylcarbamate

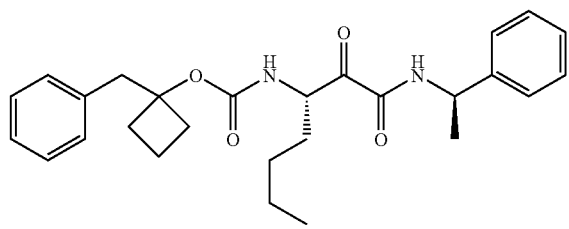

Example 1a

Preparation of methyl(2S)-2-isocyanatohexanoate

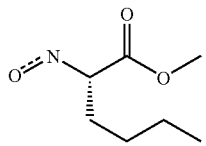

To 25.00 g (137.62 mmol) of methyl(2S)-2-aminohexanoate hydrochloride in 458 mL of dichloromethane at 0° C. was added 44.52 mL (550.49 mmol) of pyridine. Then, 85.57 mL (165.14 mmol) of a 1.93 M solution of phosgene in toluene was added to the solution and the mixture was stirred at 0° C. for 3 h. The solution was poured into 1N hydrochloric acid at 0° C. and extracted with dichloromethane. The organic layer was washed with 1N hydrochloric acid and saturated sodium chloride. The organic layer was dried over magnesium sulfate, filtered, and concentrated. The residue was purified by vacuum distillation at 80° C. @ 2 torr to give 21.32 g (91%) of methyl(2S)-2-isocyanatohexanoate. $R_f$=0.46 (1:4 ethyl acetate:hexanes); $^1$H NMR (300 MHz, DMSO-$d_6$)δ 4.37 (dd, J=7 Hz, J=5 Hz, 1H), 3.73 (s, 3H), 1.78-1.60 (m, 2H), 1.36-1.16 (m, 4H), 0.85 (t, J=7 Hz, 3H); ES-MS m/z 172 (M+H).

Example 1b

Preparation of methyl(2S)-2-({[(1-benzylcyclobutyl)oxy]carbonyl}amino)hexanoate

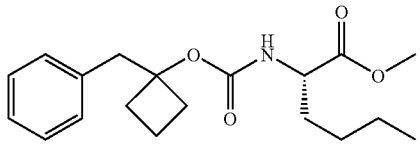

To 3.00 g (42.80 mmol) of cyclobutanone in 143 mL of tetrahydrofuran at 0° C. was added 51.36 mL (51.36 mmol) of a 1 M solution of benzyl magnesium chloride in diethyl ether and the mixture was allowed to warm to RT and stirred for 20 h. The reaction was quenched with methanol, followed by water. The mixture was extracted with ethyl acetate. The organic layer was washed with saturated sodium chloride. The organic layer was dried over magnesium sulfate, filtered, and concentrated to give 6.52 g (94%) of 1-benzylcyclobutanol. Then, 1.90 g (11.69 mmol) of the compound was dissolved in 12 mL of toluene and 2.00 g (11.69 mmol) of methyl(2S)-2-isocyanatohexanoate was added. The mixture was heated at 85° C. for 3 d. The solution was concentrated and the residue was purified by silica gel column chromatography eluting with an ethyl acetate:hexanes solution (1:6) to give 2.44 g (63%) of methyl (2S)-2-({[(1-benzylcyclobutyl)oxy]carbonyl}amino)hexanoate. $R_f$=0.30 (1:4 ethyl acetate:hexanes); $^1$H NMR (300 MHz, DMSO-$d_6$) δ 7.48 (d, J=8 Hz, 1H), 7.29-7.13 (m, 5H), 4.02-3.94 (m, 1H), 3.64 (s, 3H), 3.16 (ABq, $J_{AB}$=16 Hz, $\Delta_{84\ AB}$=12 Hz, 2H), 2.22-2.02 (m, 4H), 1.82-1.44 (m, 4H), 1.36-1.18 (m, 4H), 0.86 (t, J=7 Hz, 3H).

Example 1c

Preparation of 1-benzylcyclobutyl(1S)-1-[cyano(triphenylphosphoranylidene)acetyl]pentylcarbamate

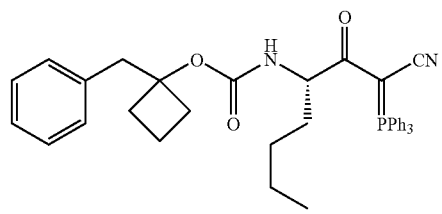

To 2.44 g (7.32 mmol) of methyl(2S)-2-({[(1-benzylcyclobutyl)oxy]carbonyl}amino)hexanoate in 24 mL of tetrahydrofuran:water (1:1) was added 429.9 mg (10.24 mmol) of lithium hydroxide monohydrate and the mixture was stirred at room temperature for 4 h. The solution was concentrated and extracted with diethyl ether. The aqueous layer was acidified with 1 N hydrochloric acid and extracted with diethyl ether. The organic layer was dried over magnesium sulfate, filtered, and concentrated. The residue was dissolver in 36 mL of dichloromethane, then 44.7 mg (365.9 µmol) of 4-dimethylaminopyridine was added. To this solution was added 2.31 g (7.68 mmol) of (triphenylphosphoranylidene)acetonitrile, followed by 1.55 g (8.05 mmol) of 1-ethyl-3-(3-dimethyl-aminopropyl)carbodiimide, and the mixture was stirred at room temperature for 17 h. Water was added to the solution and it was extracted with ethyl acetate. The organic layer was washed with 10% citric acid, followed by saturated sodium bicarbonate, and saturated sodium chloride. The organic layer was dried over magnesium sulfate, filtered, and concentrated. The residue was purified by silica gel column chromatography eluting with an ethyl acetate:hexanes solution (1:1) to give 3.25 g (74%) of 1-benzylcyclobutyl(1S)-1-[cyano(triphenylphosphoranylidene)acetyl]pentylcarbamate. $R_f$=0.25 (1:1 ethyl acetate:hexanes); $^1$H NMR (300 MHz, DMSO-$d_6$) δ 7.75-7.66 (m, 3H), 7.64-7.54 (m, 12H), 7.20-7.14 (m, 5H), 7.03 (d, J=8 Hz, 1H), 4.55-4.50 (m, 1H), 3.21 (m, 2H), 2.24-2.16 (m, 2H), 2.14-2.06 (m, 2H), 1.80-1.70 (m, 2H), 1.70-1.60

(m, 1H), 1.60-1.46 (m, 1H), 1.42-1.24 (m, 4H), 0.89 (t, J=7 Hz, 3H); ES-LCMS m/z 603 (M+H).

Example 1d

Preparation of 1-benzylcyclobutyl(1S)-1-(oxo{[(1R)-1-phenylethyl]amino}acetyl)pentylcarbamate

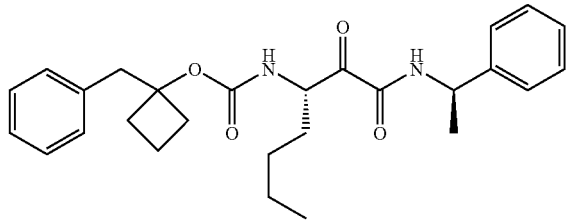

Ozone was bubbled through a solution of 402.0 mg (667.0 μmol) of 1-benzylcyclobutyl (1S)-1-[cyano(triphenylphosphoranylidene)acetyl]pentylcarbamate in 13 mL of dichloromethane at −78° C. for 15 min. The solution was purged with nitrogen for 5 min, then 86.0 μL (667.0 μmol) of (S)-α-methylbenzylamine was added and the solution was stirred at −78° C. for 15 min. The solution was concentrated and 5 mL of a 1 M solution of silver nitrate in tetrahydrofuran:water (4:1) was added and the mixture was stirred for 16 h at room temperature. The solution was extracted with ethyl acetate. The organic layer was washed with 10% citric acid, followed by saturated sodium bicarbonate, and saturated sodium chloride. The organic layer was dried over magnesium sulfate, filtered, and concentrated. The residue was purified by silica gel column chromatography eluting with an acetone:hexanes solution (1:3) to give 30.2 mg (10%) of 1-benzylcyclobutyl(1S)-1-(oxo{[(1R)-1-phenylethyl]amino}acetyl)pentylcarbamate. $R_f$=0.24 (1:4 acetone:hexanes); $^1$H NMR (300 MHz, DMSO-$d_6$) δ 9.20 (d, J=8 Hz, 1H), 7.46 (d, J=7 Hz, 1H), 7.34-7.09 (m, 10H), 4.98 (p, J=8 Hz, 1H), 4.80-4.72 (m, 1H), 3.15 (s, 2H), 2.22-2.02 (m, 4H), 1.80-1.54 (m, 3H), 1.42 (d, J=7 Hz, 3H), 1.42-1.14 (m, 5H), 0.81 (t, J=7 Hz, 3H); HRMS $C_{27}H_{34}N_2O_4$+Na m/z 473.2416 (M+Na)$_{Cal}$; 473.2423 (M+Na)$_{Obs}$.

Example 2

1-Benzylcyclopentyl(1S)-1-(oxo{[(1R)-1-phenylethyl]amino}acetyl)pentylcarbamate

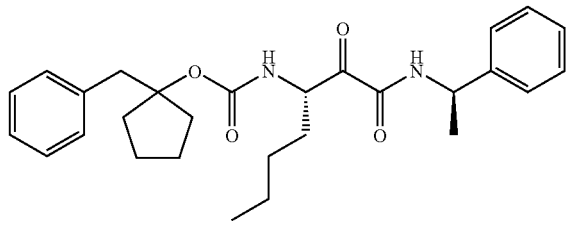

Example 2a

Preparation of 1-benzylcyclopentanol

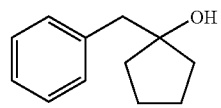

To 2.85 g (33.88 mmol) of cyclobutanone in 170 mL of tetrahydrofuran at 0° C. was added 25.41 mL (50.82 mmol) of a 2 M solution of benzyl magnesium chloride in tetrahydrofuran and the mixture was allowed to warm to RT and stirred for 17 h. The reaction was quenched with ice, then acidified with 1 N hydrochloric acid. The mixture was extracted with ethyl acetate. The organic layer was washed with saturated sodium chloride. The organic layer was dried over magnesium sulfate, filtered, and concentrated. The residue was purified by silica gel column chromatography eluting with an ethyl acetate:hexanes solution (1:6) to give 3.14 g (53%) of 1-benzylcyclopentanol. $^1$H NMR (300 MHz, DMSO-$d_6$) δ 7.27-7.19 (m, 5H), 4.19 (s, 1H), 2.78 (s, 2H), 1.69 (br m, 2H), 1.51 (br m, 6H); ES-LCMS m/z 176 (M+H).

Example 2b

Preparation of methyl(2S)-2-({[(1-benzylcyclopentyl)oxy]carbonyl}amino)hexanoate

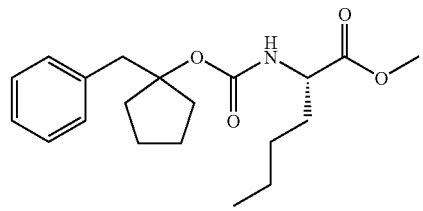

To 840.8 mg (4.77 mmol) of 1-benzylcyclopentanol in 2.4 mL of toluene was added 816.7 mg (4.77 mmol) of methyl (2S)-2-isocyanatohexanoate. The mixture was heated at 85° C. for 4 d. The solution was concentrated and the residue was purified by silica gel column chromatography eluting with an ethyl acetate:hexanes solution (1:4) to give 1.31 g (79%) of methyl(2S)-2-({[(1-benzylcyclopentyl)oxy]carbonyl}amino)hexanoate. $R_f$=0.31 (1:4 ethyl acetate:hexanes); $^1$H NMR (300 MHz, DMSO-$d_6$) δ 7.37 (d, J=8 Hz, 1H), 7.27-7.06 (m, 5H), 4.00 (m, 1H), 3.64 (s, 3H), 3.19 (ABq, $J_{AB}$=14 Hz, $\Delta_{vAB}$=9 Hz, 2H), 1.96-1.78 (m, 2H), 1.76-1.38 (m, 8H), 1.36-1.14 (m, 4H), 0.86 (t, J=7 Hz, 3H); ES-LCMS m/z 370 (M+Na).

Example 2c

Preparation of 1-benzylcyclopentyl(1S)-1-[cyano (triphenylphosphoranylidene)acetyl]pentylcarbamate

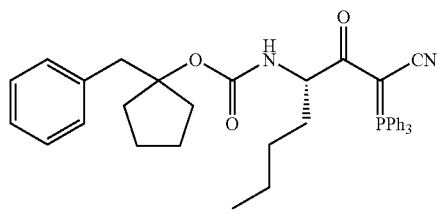

To 1.31 g (3.77 mmol) of methyl(2S)-2-({[(1-benzylcyclopentyl)oxy]carbonyl}amino)hexanoate in 12 mL of tetrahydrofuran:water (1:1) was added 221.5 mg (5.28 mmol) of lithium hydroxide monohydrate and the mixture was stirred at room temperature for 4 h. The solution was concentrated and extracted with ethyl acetate. The aqueous layer was acidified with 1 N hydrochloric acid and extracted with ethyl acetate. The organic layer was dried over magnesium sulfate, filtered, and concentrated. The residue was dissolved in 19 mL of dichloromethane, then 23.0 mg (188.5 μmol) of 4-dimethylaminopyridine was added. To this solution was added 1.19 g (3.96 mmol) of (triphenylphosphoranylidene)acetonitrile, followed by 799.2 mg (4.15 mmol) of 1-ethyl-3-(3-dimethyl-aminopropyl)carbodiimide, and the mixture was stirred at room temperature for 19 h. Water was added to the solution and it was extracted with ethyl acetate. The organic layer was washed with 10% citric acid, followed by saturated sodium bicarbonate, and saturated sodium chloride. The organic layer was dried over magnesium sulfate, filtered, and concentrated. The residue was purified by silica gel column chromatography eluting with an ethyl acetate:hexanes solution (1:1) to give 789.8 mg (34%) of 1-benzylcyclopentyl(1S)-1-[cyano(triphenylphosphoranylidene)acetyl]pentylcarbamate. $R_f$=0.31 (1:1 ethyl acetate:hexanes); $^1$H NMR (300 MHz, DMSO-$d_6$) δ 7.76-7.66 (m, 3H), 7.64-7.54 (m, 12H), 7.20-7.14 (m, 5H), 6.90 (d, J=8 Hz, 1H), 4.58-4.50 (m, 1H), 3.24 (ABq, $J_{AB}$=14 Hz, $\Delta_{vAB}$=31 Hz, 2H), 1.88-1.66 (m, 4H), 1.64-1.44 (m, 6H), 1.42-1.14 (m, 4H), 0.89 (t, J=7 Hz, 3H); ES-LCMS m/z 617 (M+H).

Example 2d

Preparation of 1-benzylcyclopentyl(1S)-1-(oxoqj {[(1R)-1-phenylethyl]amino}acetyl)pentylcarbamate

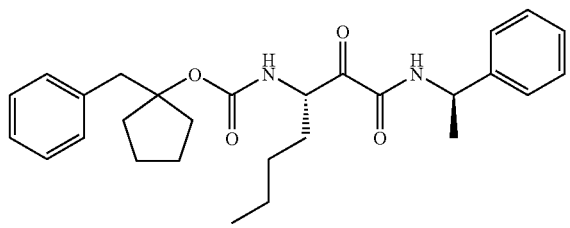

Ozone was bubbled through a solution of 304.6 mg (493.9 μmol) of 1-benzylcyclopentyl(1S)-1-[cyano(triphenylphosphoranylidene)acetyl]pentylcarbamate in 10 mL of dichloromethane at −78° C. for 15 min. The solution was purged with nitrogen for 5 min, then 63.7 μL (493.9 μmol) of (S)-α-methylbenzylamine was added and the solution was stirred at −78° C. for 15 min. The solution was concentrated and 5 mL of a 1 M solution of silver nitrate in tetrahydrofuran:water (4:1) was added and the mixture was stirred for 16 h at room temperature. The solution was extracted with ethyl acetate. The organic layer was washed with 10% citric acid, followed by saturated sodium bicarbonate, and saturated sodium chloride. The organic layer was dried over magnesium sulfate, filtered, and concentrated. The residue was purified by silica gel column chromatography eluting with an ethyl acetate:hexanes solution (1:4) to give 33.4 mg (15%) of 1-benzylcyclopentyl(1S)-1-(oxo{[(1R)-1-phenylethyl]amino}acetyl)pentylcarbamate. $R_f$=0.23 (1:4 ethyl acetate:hexanes); $^1$H NMR (300 MHz, DMSO-$d_6$) δ 9.19 (d, J=8 Hz, 1H), 8.31-7.11 (m, 11H), 4.98 (p, J=8 Hz, 1H), 4.82-4.74 (m, 1H), 3.18 (s, 2H), 1.94-1.80 (m, 2H), 1.78-1.54 (m, 6H), 1.42 (d, J=7 Hz, 3H), 1.40-1.16 (m, 6H), 0.81 (t, J=7 Hz, 3H); HRMS $C_{28}H_{36}N_2O_4$+Na m/z 487.2573 (M+Na)$_{Cal}$; 487.2568 (M+Na)$_{Obs}$.

Example 3

Benzyl (2S)-2-{[(3S)-3-({[(1-benzylcyclopentyl)oxy]carbonyl}amino)-2-oxoheptanoyl]amino}propanoate

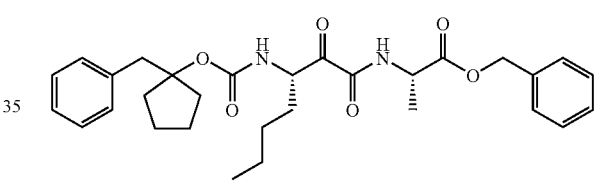

Ozone was bubbled through a solution of 205.1 mg (332.6 μmol) of 1-benzylcyclopentyl(1S)-1-[cyano(triphenylphosphoranylidene)acetyl]pentylcarbamate in 7 mL of dichloromethane at −78° C. for 15 min. The solution was purged with nitrogen for 5 min, then 71.7 mg (332.6 μmol) of benzyl(2S)-2-aminopropanoate hydrochloride and 58.2 mL (332.6 mmol) of diisopropylethylamine were added and the solution was stirred at −78° C. for 15 min. The solution was concentrated and 5 mL of a 1 M solution of silver nitrate in tetrahydrofuran:water (4:1) was added and the mixture was stirred for 19 h at room temperature. The solution was extracted with ethyl acetate. The organic layer was washed with 10% citric acid, followed by saturated sodium bicarbonate, and saturated sodium chloride. The organic layer was dried over magnesium sulfate, filtered, and concentrated. The residue was purified by silica gel column chromatography eluting with an acetone:hexanes solution (1:3) to give 29.5 mg (11%) of benzyl (2S)-2-{[(3S)-3-({[(1-benzylcyclopentyl)oxy]carbonyl}amino)-2-oxoheptanoyl]amino}propanoate. $R_f$=0.19 (1:4 acetone:hexanes); $^1$H NMR (400 MHz, DMSO-$d_6$) δ 9.17 (d, J=7 Hz, 1H), 7.38-7.08 (m, 1 H), 5.13 (s, 2H), 4.81 (m, 1H), 4.40 (p, J=8 Hz, 1H), 3.18 (ABq, $J_{AB}$=14 Hz, $\Delta_{vAB}$=8 Hz, 2H), 1.94-1.82 (m, 2H), 1.78-1.54 (m, 6H), 1.48-1.18 (m, 6H), 1.36 (d, J=7 Hz, 3H), 0.86 (t, J=7 Hz, 3H); HRMS $C_{30}H_{38}N_2O_6$+Na m/z 545.2628 (M+Na)$_{Cal}$; 545.2605 (M+Na)$_{Obs}$.

Example 4

1-Benzylcyclohexyl(1S)-1-(oxo{[(1R)-1-phenylethyl]amino}acetyl)pentylcarbamate

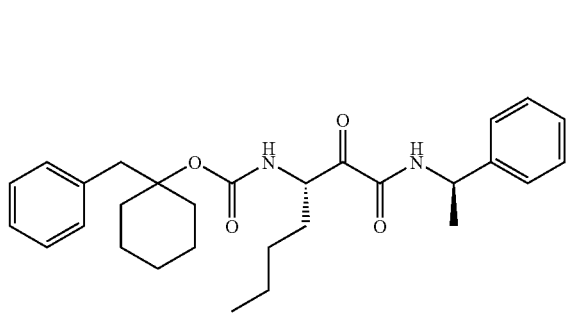

Example 4a

Preparation of methyl(2S)-2-({[(1-benzylcyclohexyl)oxy]carbonyl}amino)hexanoate

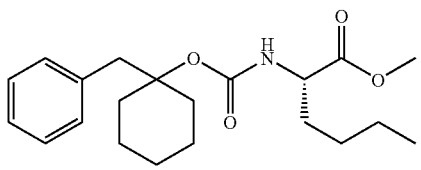

To 3.00 g (30.57 mmol) of cyclohexanone in 102 mL of tetrahydrofuran at 0° C. was added 36.68 mL (36.68 mmol) of a 1 M solution of benzyl magnesium chloride in diethyl ether and the mixture was allowed to warm to RT and stirred for 17 h. The reaction was quenched with methanol, followed by water. The mixture was extracted with ethyl acetate. The organic layer was washed with saturated sodium chloride. The organic layer was dried over magnesium sulfate, filtered, and concentrated to give 3.84 g (66%) of 1-benzylcyclohexanol. Then, 2.23 g (11.69 mmol) of the compound was dissolved in 5.8 mL of toluene and 2.00 g (11.69 mmol) of methyl(2S)-2-isocyanatohexanoate was added. The mixture was heated at 85° C. for 12 d. The solution was concentrated and the residue was purified by silica gel column chromatography eluting with an ethyl acetate:hexanes solution (1:6) to give 1.90 g (45%) of methyl(2S)-2-({[(1-benzylcyclohexyl)oxy]carbonyl}amino)hexanoate. $R_f$=0.39 (1:4 ethyl acetate:hexanes); $^1$H NMR (300 MHz, DMSO-$d_6$) δ 7.36 (d, J=8 Hz, 1H), 7.25-7.10 (m, 5H), 4.02-3.97 (m, 1H), 3.65 (s, 3H), 3.12 (s, 2H), 1.72-1.06 (m, 16H), 0.87 (t, J=7 Hz, 3H).

Example 4b

Preparation of 1-benzylcyclohexyl(1S)-1-[cyano(triphenylphosphoranylidene)acetyl]pentylcarbamate

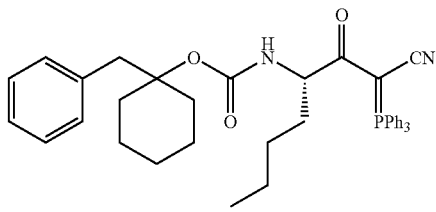

To 1.90 g (5.26 mmol) of methyl(2S)-2-({[(1-benzylcyclohexyl)oxy]carbonyl}amino)hexanoate in 18 mL of tetrahydrofuran:water (1:1) was added 308.8 mg (7.36 mmol) of lithium hydroxide monohydrate and the mixture was stirred at room temperature for 4 h. The solution was concentrated and extracted with diethyl ether. The aqueous layer was acidified with 1 N hydrochloric acid and extracted with diethyl ether. The organic layer was dried over magnesium sulfate, filtered, and concentrated. The residue was dissolved in 15 mL of dichloromethane, then 19.0 mg (155.4 μmol) of 4-dimethylaminopyridine was added. To this solution was added 983.4 mg (3.26 mmol) of (triphenylphosphoranylidene)acetonitrile, followed by 658.8 mg (3.42 mmol) of 1-ethyl-3-(3-dimethyl-aminopropyl)carbodiimide, and the mixture was stirred at room temperature for 16 h. Water was added to the solution and it was extracted with ethyl acetate. The organic layer was washed with 10% citric acid, followed by saturated sodium bicarbonate, and saturated sodium chloride. The organic layer was dried over magnesium sulfate, filtered, and concentrated. The residue was purified by silica gel column chromatography eluting with an ethyl acetate:hexanes solution (1:1) to give 1.29 g (39%) of 1-benzylcyclohexyl(1S)-1-[cyano(triphenylphosphoranylidene)acetyl]pentylcarbamate. $R_f$=0.32 (1:1 ethyl acetate:hexanes); $^1$H NMR (300 MHz, DMSO-$d_6$) δ 7.74-7.70 (m, 3H), 7.62-7.50 (m, 12H), 7.22-7.12 (m, 5H), 6.90 (d, J=8 Hz, 1H), 4.60-4.52 (m, 1H), 3.23 (ABq, $J_{AB}$=13 Hz, $\Delta_{vAB}$=40 Hz, 2H), 2.19 (d, J=13 Hz, 1H), 1.95 (d, J=16 Hz, 1H), 1.86-1.68 (m, 1H), 1.60-1.10 (m, 13H), 0.90 (t, J=7 Hz, 3H).

Example 4c

Preparation of 1-benzylcyclohexyl(1S)-1-(oxo{[(1R)-1-phenylethyl]amino}acetyl)pentylcarbamate

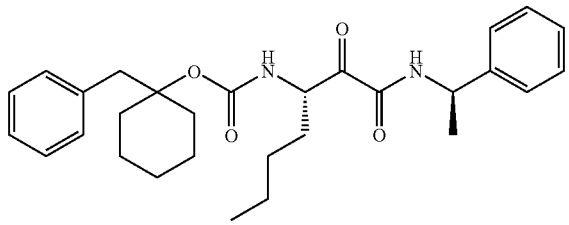

Ozone was bubbled through a solution of 393.0 mg (623.0 μmol) of 1-benzylcyclohexyl (1S)-1-[cyano(triphenylphosphoranylidene)acetyl]pentylcarbamate in 12 mL of dichloromethane at −78° C. for 15 min. The solution was purged with nitrogen for 5 min, then 80.3 μL (623.0 μmol) of (S)-α-methylbenzylamine was added and the solution was stirred at −78° C. for 15 min. The solution was concentrated and 5 mL of a 1 M solution of silver nitrate in tetrahydrofuran:water (4:1) was added and the mixture was stirred for 66 h at room temperature. The solution was extracted with ethyl acetate. The organic layer was washed with 10% citric acid, followed by saturated sodium bicarbonate, and saturated sodium chloride. The organic layer was dried over magnesium sulfate, filtered, and concentrated. The residue was purified by silica gel column chromatography eluting with an ethyl acetate:hexanes solution (1:4) to give 115.6 mg (39%) of 1-benzylcyclohexyl(1S)-1-(oxo{[(1R)-1-phenylethyl]amino}acetyl)pentylcarbamate. $R_f$=0.30 (1:4 ethyl acetate:hexanes); $^1$H NMR (300 MHz, DMSO-$d_6$) δ 9.18 (d, J=8 Hz, 1H), 7.36-7.06 (m, 11H), 4.98 (p, J=8 Hz, 1H), 4.82-4.74 (m, 1H), 3.10 (s, 2H), 2.01 (d, J=12 Hz, 2H), 1.80-1.10 (m, 14H), 1.42 (d, J=7 Hz, 3H), 0.82 (t, J=7 Hz, 3H); HRMS $C_{29}H_{38}N_2O_4$+Na m/z 501.2729 (M+Na)$_{Cal}$; 501.2711 (M+Na)$_{Obs}$.

Example 5

(1-Benzylcyclobutyl)methyl(1S)-1-(oxo{[(1R)-1-phenylethyl]amino}acetyl)pentylcarbamate

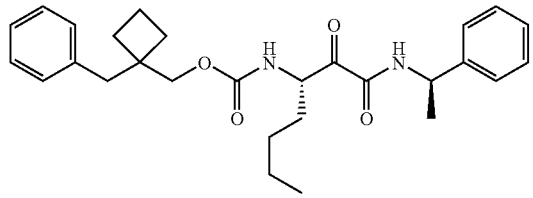

Example 5a

Preparation of benzyl(1S)-1-(hydroxymethyl)pentylcarbamate

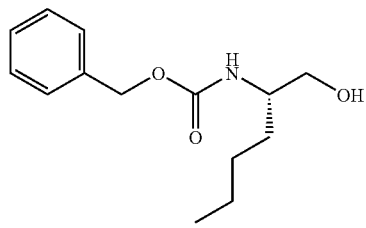

A solution of 95.0 mL (95.0 mmol) of 1 M isopropylchloroformate in toluene was added dropwise to a solution of 13.2 mL (95.0 mmol) of triethylamine and 25.16 g (95.0 mmol) of (2S)-2-{[(benzyloxy)carbonyl]amino}hexanoic acid in 200 mL of anhydrous tetrahydrofuran at 0° C. under nitrogen. After 2 h, the resulting mixture was filtered directly into a solution of 7.2 g (190 mmol) of sodium borohydride in 200 mL of water. The resulting mixture was stirred for 18 h, and then extracted with ethyl acetate. The extract was washed with saturated aqueous sodium bicarbonate, dried over magnesium sulfate, and concentrated under vacuum. The oily solid was further purified by column chromatography on silica gel, eluting with 4:6 ethyl acetate:hexane to afford 9.63 g (40%) of (1S)-1-(hydroxymethyl)pentylcarbamate. $^1$H NMR (300 MHz, DMSO-$d_6$) δ 7.37 (m, 5H), 6.97 (d, J=9 Hz, 1H), 5.03 (s, 2H), 4.62 (bs, 1H), 3.46-3.23 (m under water peak, 3H), 1.53 (m, 1H), 1.26 (m, 5H), 0.87 (t, J=6 Hz, 3H); ES-LCMS m/z 274 (M+Na).

Example 5b

Preparation of benzyl(1S)-1-formylpentylcarbamate

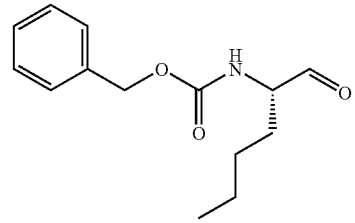

A solution of 16.38 g (103 mmol) of sulfur trioxide pyridine complex in 130 mL of dimethylsulfoxide was added to a solution of 8.64 g (34.4 mmol) of (1S)-1-(hydroxymethyl)pentylcarbamate) and 14.4 mL (103 mmol) of triethylamine in 130 mL of dichloromethane at −10° C. After 1 h, the cold bath was removed, and the reaction mixture was stirred for 18 h. It was then poured slowly into a mixture of ice and saturated aqueous sodium chloride. The resulting mixture was extracted with ether. The ether extracts were then washed with 5% aqueous citric acid, and saturated aqueous sodium chloride. After drying over magnesium sulfate, volatiles were removed under vacuum to afford 7.27 g (85%) of benzyl (1S)-1-formylpentylcarbamate. $^1$H NMR (400 MHz, DMSO-$d_6$) δ 9.41 (s, 1H), 7.66 (d, J=8 Hz, 1H), 7.33-7.28 (m, 5H), 5.00 (s, 2H), 3.85 (m, 1H), 1.65 (m, 1H), 1.40 (m, 1H), 1.27-1.18 (m, 4H), 0.79 (m, 3H). ES-LCMS m/z 248 (M−H).

Example 5c

Preparation of (1R)-α-methylbenzylisonitrile

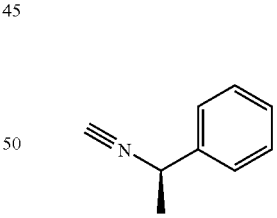

50 mL of 50% (w/w) aqueous sodium hydroxide was added to a solution of 17.5 mL (136 mmol) of (1R)-1-phenylethanamine, 10.8 mL (136 mmol) of chloroform, and 0.5 g (2.2 mmol) of benzyltriethylammonium chloride in 50 mL of dichloromethane. The resulting mixture was stirred for 3 h, and was then diluted with 100 mL of water and extracted with three 150 mL portions of dichloromethane. The combined extracts were washed with 50 mL portions of water and saturated aqueous sodium chloride, dried over magnesium sulfate, and concentrated under vacuum to afford a dark liquid, which was further purified by column chromatography on silica gel. Elution with dichloromethane afforded 9.86 g (55%) of (1R)-α-methylbenzylisonitrile. $^1$H NMR (400 MHz, DMSO-d$_6$) δ 7.38-7.36 (m, 4H), 7.32 (m, 1H), 5.08 (m, 1H), 1.53 (m, 3H).

Example 5d

Preparation of (2S)-2-{[(benzyloxy)carbonyl]amino}-1-({[(1R)-1-phenylethyl]amino}carbonyl)hexyl benzoate

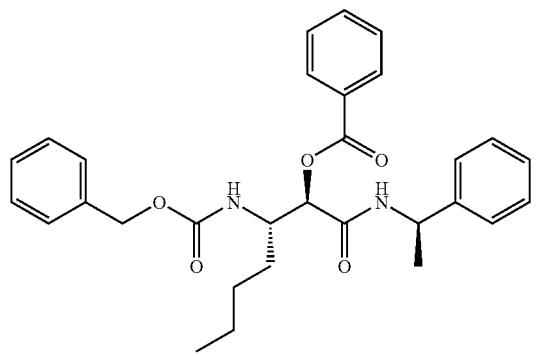

+

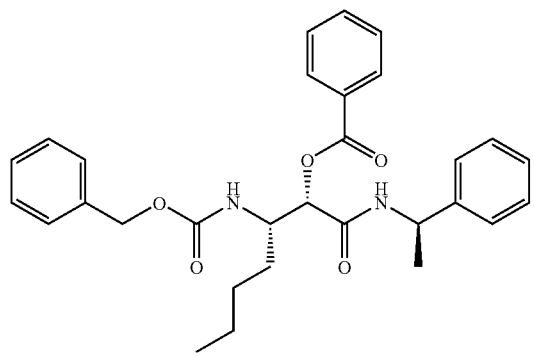

To a solution of 7.27 g (29 mmol) of benzyl (1S)-1-formylpentylcarbamate in 300 ml. of dichloromethane was added 3.8 g (29 mmol) of (1R)-α-methylbenzylisonitrile and 3.54 g (29 mmol) of benzoic acid. The reaction was stirred at room temperature for 48 h and diluted with a copious amount of hexanes. The precipitate was collected by filtration and the wash filtered through a silica plug with 1:9 ethyl ether:dichloromethane. The wash was concentrated and the residue was combined with the collected precipitate to afford 8.7 g (60%) of (2S)-2-{[(benzyloxy)carbonyl]amino}-1-({[(1R)-1-phenylethyl]amino}carbonyl)hexyl benzoate. $^1$H NMR (400 MHz, DMSO-d$_6$) δ 8.60 (d, J=8 Hz, 1H), 8.05 (d, J=7 Hz, 2H), 7.62 (t, J=8 Hz, 1H), 7.47 (t, J=8 Hz, 2H), 7.31-7.07 (m, 11H), 4.96 (m, 3H), 4.85 (qnt, J=7 Hz, 1H), 4.06 (m, 1H), 1.45-1.05 (m, 9H), 0.73 (t, J=7 Hz, 3H). ES-LCMS m/z 525 (M+Na).

Example 5e

Preparation of (3S)-3-amino-2-hydroxy-N-[(1R)-1-phenylethyl]heptanamide

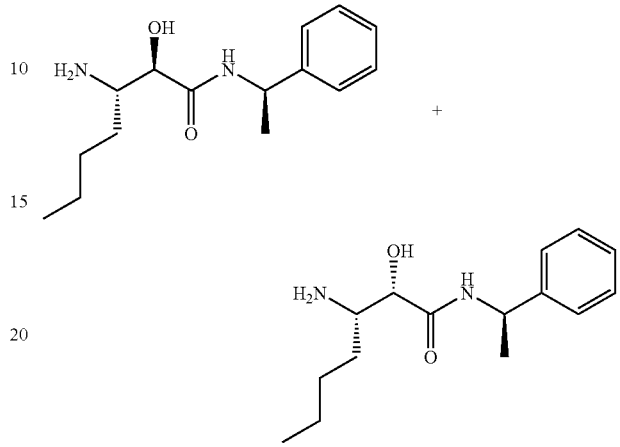

A mixture of 8.75 g (17.4 mmol) of (2S)-2-{[(benzyloxy)carbonyl]amino}-1-({[(1R)-1-phenylethyl]amino}carbonyl)hexyl benzoate and 6.97 g (174 mmol) of sodium hydroxide in 175 mL of dioxane and 75 mL of water was heated to reflux for 3 h and then let cool to room temperature. The reaction was diluted with 100 mL of water and extracted with ethyl acetate. The combined ethyl acetate layers were dried over potassium carbonate and concentrated to afford 4.38 g (95%) of (3S)-3-amino-2-hydroxy-N-[(1R)-1-phenylethyl]heptanamide as a white solid. $^1$H NMR (300 MHz, DMSO-d$_6$) δ 8.08 (d, J=8 Hz, 1H), 7.39-7.20 (m, 5H), 4.99 (m, 1H), 4.51 (bs, 1H), 3.71 (d, J=3 Hz, 1H), 2.81 (m, 1H), 1.50-1.05 (m, 9H), 0.87 (t, 3H). ES-LCMS m/z 265 (M+H).

Example 5f

Preparation of ethyl (1-benzylcyclobutyl)methanol

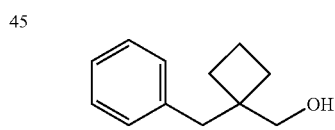

To a −78° C. solution of 2.8 mL (20.0 mmol) of diisopropylamine in 40 mL of dry tetrahydrofuran was added 13.75 mL (22 mmol) of 1.6 M n-butyllithium in hexanes. The reaction was let warm to 0° C. and then cooled to −78° C. A solution of 2.7 mL (20 mmol) of ethyl cyclobutanecarboxylate in 10 mL of tetrahydrofuran was added dropwise and the reaction let warm to 0° C. The reaction was stirred for 15 min before being cooled to −78° C. To the solution was added 3.1 mL (26 mmol) of benzyl bromide dropwise and the reaction stirred for 15 min before being let warm to room temperature and stirred overnight. The reaction was quenched with water and extracted with ethyl acetate. The organic phase was washed with saturated ammonium chloride, washed with brine, dried over magnesium sulfate, and concentrated under reduced pressure to afford 5.24 g of crude ethyl 1-benzylcyclobutanecarboxylate. The crude product was dissolved in 100 mL of tetrahydrofuran and cooled to 0° C. To this solution was added dropwise 14.1 mL (14.1 mmol) of 1M lithium aluminum hydride in tetrahydrofuran. The reaction was stirred for 1 h before being carefully quenched with brine. The mixture was filtered through a celite plug and the filter cake washed with ethyl acetate. The filtrate was washed with brine, dried over magnesium sulfate, and concentrated under reduced pressure to afford 1.6 g (45%) of ethyl (1-benzylcyclobutyl) methanol. $^1$H NMR (300 MHz, DMSO-$d_6$) δ 7.18-7.34 (m, 5H), 4.63 (t, J=5 Hz, 1H), 3.24-3.25 (d, J=5H, 2H), 2.71 (s, 2H), 1.66-1.79 (m, 6H).

Example 5g

Preparation of (1-benzylcyclobutyl)methyl(1S)-1-(1-hydroxy-2-oxo-2-{[(1R)-1-phenylethyl]amino}ethyl)pentylcarbamate

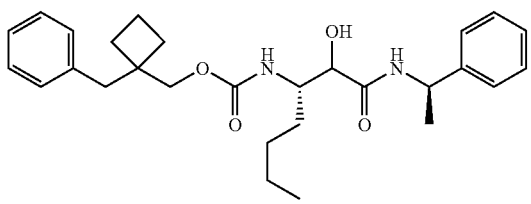

To a solution of 100 mg (0.57 mmol) of ethyl (1-benzylcyclobutyl)methanol in 3 mL of tetrahydrofuran was added 0.68 mL (1.31 mmol) of 1.93 M phosgene in toluene in one portion. The reaction was stirred overnight at room temperature. The mixture was concentrated under vacuum. The remaining oil was dissolved in 1 mL tetrahydrofuran and added to a solution of 136 mg (0.516 mmol) of (3S)-3-amino-2-hydroxy-N-[(1R)-1-phenylethyl]heptanamide and 0.079 mL (0.568 mmol) of triethylamine in 5 mL tetrahydrofuran. The reaction was stirred at room temperature for 3 h, diluted with ethyl acetate, and washed with 1M hydrochloric acid. The organic phase was washed with brine, dried over magnesium sulfate, and concentrated under reduced pressure to afford 240 mg (99%) of (1-benzylcyclobutyl) methyl(1S)-1-(1-hydroxy-2-oxo-2-{[(1R)-1-phenylethyl]amino}ethyl)pentylcarbamate. $^1$H NMR (300 MHz, DMSO-$d_6$) δ 8.07 (d, J=9 Hz, 1H), 7.17-7.36 (m, 10H), 6.57 (d, J=9 Hz, 1H), 5.57 (d, J=6 Hz, 1H), 4.90-5.02 (m, 1H), 3.89-3.94 (m, 1H), 3.75-3.84 (m, 3H), 2.77 (s, 2H), 1.70-1.93 (m, 6H), 1.25-1.53 (m, 9H), 0.88 (t, J=7 Hz, 3H). ES-LCMS m/z 489 (M+Na).

Example 5h

Preparation of (1-benzylcyclobutyl)methyl(1S)-1-(oxo{[(1R)-1-phenylethyl]amino}acetyl)pentylcarbamate

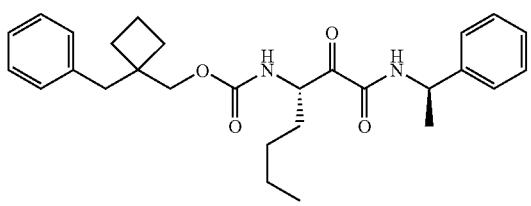

To a solution of 240 mg (0.51 mmol) of (1-benzylcyclobutyl)methyl(1S)-1-(1-hydroxy-2-oxo-2-{[(1R)-1-phenylethyl]amino}ethyl)pentylcarbamate in 2 mL of dichloromethane at 0° C. was added 1 mg of 2,2,6,6-tetramethyl-1-piperidinyloxy free radical and 5 mg of potassium bromide. A solution of 30 mg of sodium bicarbonate in 2.5 mL of household bleach was added and the reaction stirred for 30 min. The reaction was extracted with ethyl acetate and and washed 0.5 N hydrochloric acid. The organic phase was washed with saturated sodium bicarbonate, washed with brine, dried over magnesium sulfate, and concentrated under vacuum. The product was purified by silica chromatography eluting with 2.5:7.5 acetone:hexanes to afford 128 mg (53%) of (1-benzylcyclobutyl)methyl(1S)-1-(oxo{[(1R)-1-phenylethyl]amino}acetyl)pentylcarbamate. M.P.=96-98° C. Elemental analysis: Theory; C=72.39%, H=7.81%, N=6.03%. Found; C=72.14%, H=7.81%, N=5.99%. $^1$H NMR (300 MHz, 80° C., DMSO-$d_6$) δ 8.83 (d, J=8 Hz, 1H), 7.19-7.38 (m, 11H), 5.02 (qnt, J=7 Hz, 1H), 4.85 (m, 1H), 3.83 (s, 2H), 2.79 (s, 1H), 1.67-1.89 (m, 7H), 1.51-1.60 (m, 1H), 1.47 (d, J=7 Hz, 3H), 1.25-1.40 (m, 4H), 0.86 (t, J=7 Hz, 3H). ES-LCMS m/z 487 (M+Na). HRMS $C_{28}H_{36}N_2O_4$ m/z 487.2573 $(M+Na)_{Cal}$; 487.2552 $(M+Na)_{Obs}$.

Example 6

[1-(2-Phenylethyl)cyclobutyl]methyl(1S)-1-(oxo{[(1R)-1-phenylethyl]amino}acetyl)pentylcarbamate

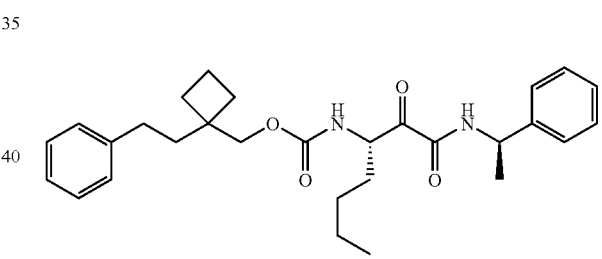

Example 6a

Preparation of [1-(2-phenylethyl)cyclobutyl]methanol

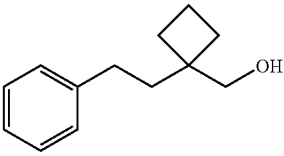

[1-(2-Phenylethyl)cyclobutyl]methanol was prepared as in example 5f except that (2-bromoethyl)benzene was substituted for benzyl bromide. $^1$H NMR (300 MHz, DMSO-$d_6$) δ 7.17-7.38 (m, 5H), 4.59 (t, J=5 Hz, 1H), 3.41 (d, J=5 Hz, 2H), 2.50 under DMSO peak (m, 2H), 1.66-1.81 (m, 8H).

Example 6b

Preparation of [1-(2-phenylethyl)cyclobutyl]methyl (1S)-1-(1-hydroxy-2-oxo-2-{[(1R)-1-phenylethyl]amino}ethyl)pentylcarbamate

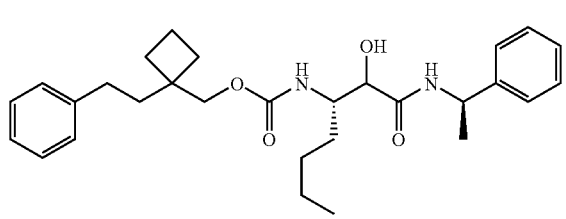

[1-(2-Phenylethyl)cyclobutyl]methyl(1S)-1-(1-hydroxy-2-oxo-2-{[(1R)-1-phenylethyl]amino}ethyl)pentylcarbamate was prepared as in example 5 g except that [1-(2-phenylethyl)cyclobutyl]methanol was substituted for ethyl (1-benzylcyclobutyl)methanol. $^1$H NMR (400 MHz, DMSO-$d_6$) δ 7.98 (d, J=8 Hz, 1H), 7.10-7.25 (m, 10H), 6.41 (d, J=9 Hz, 1H), 5.46 (d, J=6 Hz, 1H), 4.86 (m, 1H), 4.00 (d, J=11 Hz, 1H), 3.87 (d, J=11 Hz, 1H), 3.82 (m, 1H), 3.75 (m, 1H), 1.63-1.77 (m, 8H), 1.20-1.45 (m, 10H), 0.77(t, J=7 Hz, 3H). ES-LCMS m/z 503 (M+Na).

Example 6c

Preparation of [1-(2-phenylethyl)cyclobutyl]methyl (1S)-1-(oxo{[(1R)-1-phenylethyl]amino}acetyl)pentylcarbamate

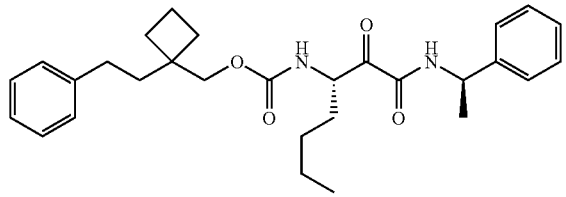

To a solution of 75 mg (0.16 mmol) of [1-(2-phenylethyl)cyclobutyl]methyl(1S)-1-(1-hydroxy-2-oxo-2-{[(1R)-1-phenylethyl]amino}ethyl)pentylcarbamate in 1 mL of dichloromethane was added 67 mg (0.78 mmol) of sodium bicarbonate and 330 mg (0.78 mmol) of Dess-Martin periodinane. The reaction was stirred at room temperature for 3.5 h. The reaction was poured onto a silica gel column and eluted with 2.5:7.5 acetone:hexanes. Fractions containing product were concentrated to leave 74 mg of a clear oil. The oil was triturated in hexanes and the resulting white precipitate collected by filtration and air dried to afford 36 mg (48%) of [1-(2-phenylethyl)cyclobutyl]methyl(1S)-1-(oxo{[(1R)-1-phenylethyl]amino}acetyl)pentylcarbamate. M.P.=86-88° C. Elemental analysis: Theory; C=72.77%, H=8.00%, N=5.85%. Found; C=72.70%, H=7.98%, N=5.84%. $^1$H NMR (400 MHz, DMSO-$d_6$) δ 9.12 (d, J=8 Hz, 1H), 7.50 (d, J=8 Hz, 1H), 7.11-7.26 (m, 10H), 4.91 (m, 1H, 4.73 (m, 1H), 3.96 (s, 2H), 1.56-1.82 (m, 10H), 1.12-1.37 (m, 9H), 0.73 (t, J=7 Hz, 3H). ES-LCMS m/z 501 (M+Na). HRMS $C_{29}H_{38}N_2O_4$ m/z 501.2729 (M+Na)$_{Cal}$; 501.2709 (M+Na)$_{Obs}$.

Example 7

[1-(3-Phenylpropyl)cyclobutyl]methyl(1S)-1-(oxo{[(1R)-1-phenylethyl]amino}acetyl)pentylcarbamate

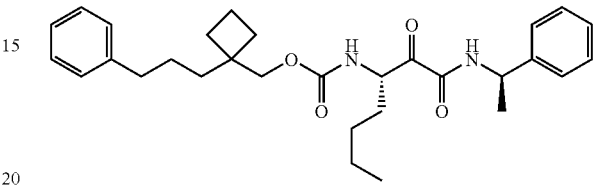

Example 7a

Preparation of [1-(3-phenylpropyl)cyclobutyl]methanol

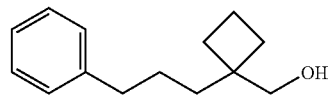

[1-(3-Phenylpropyl)cyclobutyl]methanol was prepared as in example 5f except that 1-bromo-3-phenylpropane was substituted for benzyl bromide. $^1$H NMR (300 MHz, DMSO-$d_6$) δ 7.18-7.32 (m, 5H), 4.49 (bs, 1H), 3.31 (s, 2H), 2.57 (t, J=7 Hz, 2H), 1.46-1.77 (m, 10H).

Example 7b

Preparation of [1-(3-phenylpropyl)cyclobutyl]methyl(1S)-1-(1-hydroxy-2-oxo-2-{[(1R)-1-phenylethyl]amino}ethyl)pentylcarbamate

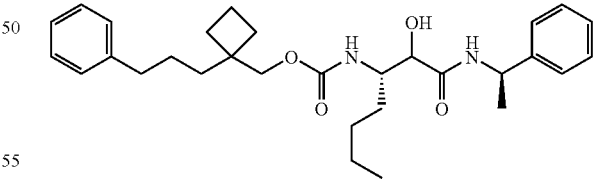

[1-(3-Phenylpropyl)cyclobutyl]methyl(1S)-1-(1-hydroxy-2-oxo-2-{[(1R)-1-phenylethyl]amino}ethyl)pentylcarbamate was prepared as in example 5g except that [1-(3-phenylpropyl)cyclobutyl]methanol was substituted for ethyl (1-benzylcyclobutyl)methanol. $^1$H NMR (400 MHz, DMSO-$d_6$) δ 7.98 (d, J=8 Hz, 1H), 7.10-7.25 (m, 10H), 6.34 (d, J=9 Hz, 1H), 5.45 (d, J=6 Hz, 1H), 4.88 (qnt, J=8 Hz, 1H), 3.69-3.91 (m, 4H), 2.48 (m, 2H), 1.41-1.63 (m, 6H), 1.19-1.45 (m, 13H), 0.79 (t, J=7 Hz, 3H). ES-LCMS m/z 517 (M+Na).

Example 7c

Preparation of [1-(3-phenylpropyl)cyclobutyl]methyl(1S)-1-(oxo{[(1R)-1-phenylethyl]amino}acetyl)pentylcarbamate

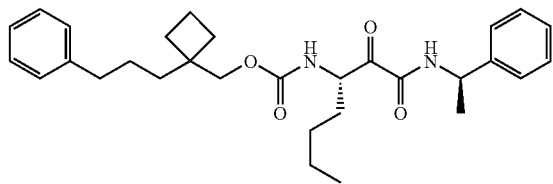

[1-(3-phenylpropyl)cyclobutyl]methyl(1S)-1-(oxo[(1R)-1-phenylethyl]amino}acetyl)pentylcarbamate was prepared as in example 6c except that [1-(3-phenylpropyl)cyclobutyl]methyl(1S)-1-(1-hydroxy-2-oxo-2-{[(1R)-1-phenylethyl]amino}ethyl)pentylcarbamate was substituted for [1-(2-phenylethyl)cyclobutyl]methyl(1S)-1-(1-hydroxy-2-oxo-2-{[(1R)-1-phenylethyl]amino}ethyl)pentylcarbamate. M.P.=91-93° C. Elemental analysis: Theory; C=73.14%, H=8.18%, N=5.69%. Found; C=72.81%, H=8.22%, N=5.82%. $^1$H NMR (400 MHz, DMSO-$d_6$) δ 9.10 (d, J=8 Hz, 1H), 7.45 (d, J=8 Hz, 1H), 7.11-7.26 (m, 10H), 4.91 (qnt, J=8 Hz, 1H), 4.70 (m, 1H), 3.85 (s, 2H), 2.50 (m, 2H), 1.55-1.74 (m, 6H), 1.13-1.45 (m, 13H), 0.74 (t, J=7 Hz, 13H). ES-LCMS m/z 515 (M+Na). HRMS $C_{30}H_{40}N_2O_4$ m/z 515.2886 (M+Na)$_{Cal}$; 515.2891 (M+Na)$_{Obs}$.

Example 8

(1-Benzylcyclopentyl)methyl(1S)-1-(oxo{[(1R)-1-phenylethyl]amino}acetyl)pentylcarbamate

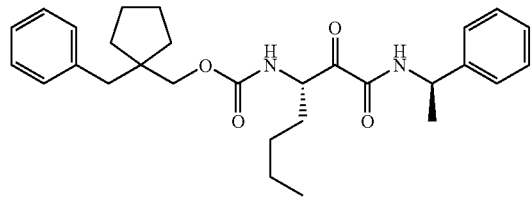

Example 8a

Preparation of (1-benzylcyclopentyl)methanol

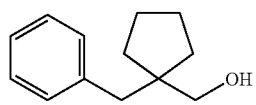

(1-Benzylcyclopentyl)methanol was prepared as in example 5g except that methyl cyclopentanecarboxylate was substituted for ethyl cyclobutanecarboxylate. $^1$H NMR (300 MHz, DMSO-$d_6$) δ 7.19-7.30 (m, 5H), 4.64 (t, J=5 Hz, 1H), 3.10 (d, J=5 Hz, 2H), 2.62 (s, 2H), 1.15-1.56 (m, 4H), 1.32-1.38 (m, 4H).

Example 8b

Preparation of (1-benzylcyclopentyl)methyl(1S)-1-(1-hydroxy-2-oxo-2-{[(1R)-1-phenylethyl]amino}ethyl)pentylcarbamate

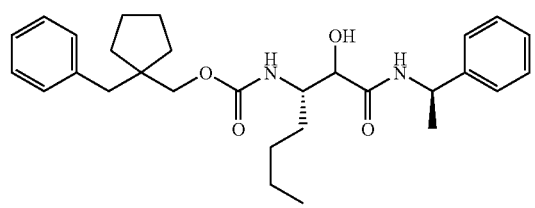

(1-Benzylcyclopentyl)methyl(1S)-1-(1-hydroxy-2-oxo-2-{[(1R)-1-phenylethyl]amino}ethyl)pentylcarbamate was prepared as in example 5f except that (1-benzylcyclopentyl)methanol was substituted for (1-benzylcyclobutyl)methanol. $^1$H NMR (300 MHz, DMSO-$d_6$) δ 8.07 (d, J=8 Hz, 1H), 7.17-7.36 (m, 10H), 6.59 (d, J=9 Hz, 1H), 5.60 (d, J=7 Hz, 1H), 4.96 (qnt, J=7 Hz, 1H), 3.92 (bs, 1H), 3.82 (m, 1H), 3.54-3.68 (m, 2H), 2.66 (m, 2H), 1.30-1.60 (m, 17H), 0.89 (t, J=6 Hz, 3H). ES-LCMS m/z 503 (M+Na).

Example 8c

Preparation of (1-benzylcyclopentyl)methyl(1S)-1-(oxo{[(1R)-1-phenylethyl]amino}acetyl)pentylcarbamate

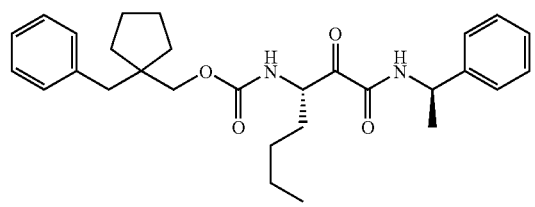

(1-Benzylcyclopentyl)methyl(1S)-1-(oxo{[(1R)-1-phenylethyl]amino}acetyl)pentylcarbamate was prepared as in example 6c except that (1-benzylcyclopentyl)methyl(1S)-1-(1-hydroxy-2-oxo-2-{[(1R)-1-phenylethyl]amino}ethyl)pentylcarbamate was substituted for (1-benzylcyclobutyl)methyl(1S)-1-(1-hydroxy-2-oxo-2-{[(1R)-1-phenylethyl]amino}ethyl)pentylcarbamate. M.P.=108-110° C. Elemental analysis: Theory; C=72.77%, H=8.00%, N=5.85%. Found; C=72.62%, H=8.00%, N=5.84%. $^1$H NMR (300 MHz, 80° C., DMSO-$d_6$) δ 8.82 (d, J=8 Hz, 1H), 7.19-7.39 (m, 11H), 5.02 (qnt, J=7 Hz, 1H), 4.86 (m, 1H), 3.69 (d, J=3 Hz, 2H), 2.69 (s, 2H), 1.20-1.65 (m, 17H), 0.87 (t, J=7 Hz, 3H). ES-LCMS m/z 501 (M+Na). HRMS $C_{29}H_{38}N_2O_4$ m/z 501.2729 (M+Na)$_{Cal}$; 501.2731 (M+Na)$_{Obs}$.

Example 9

(1-Benzylcyclohexyl)methyl(1S)-5-[(4-morpholinylcarbonyl)amino]-1-(oxo{[(1R)-1-phenylethyl]amino}acetyl)pentylcarbamate

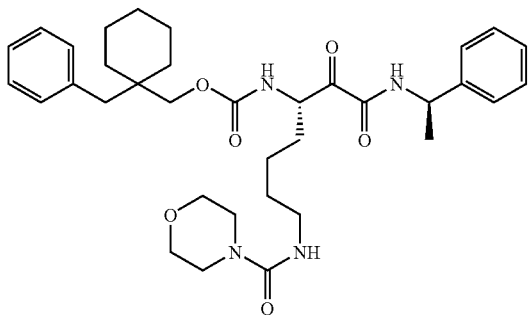

Example 9a

Preparation of benzyl (5S)-5-{[t-butyloxycarbonyl]amino}-6-hydroxyhexylcarbamate

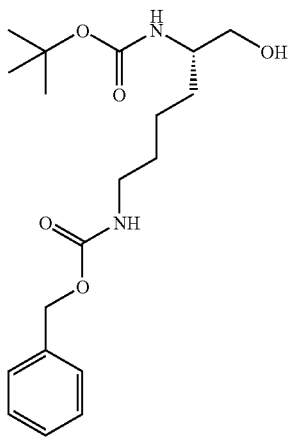

A solution of 150.0 mL (150.0 mmol) of 1 M isopropylchloroformate in toluene was added dropwise to a solution of 20.9 mL (150.0 mmol) of triethylamine and 57.06 g (150.0 mmol) of (2S)-6-{[(benzyloxy)carbonyl]amino}-2-[(tert-butoxycarbonyl)amino]hexanoic acid in 500 mL of anhydrous tetrahydrofuran at 0° C. After 2 h, the resulting mixture was filtered to remove solids, rinsing with 100 mL of anhydrous tetrahydrofuran. The filtrate was then added dropwise to a stirred solution of 11.35 g (300.0 mmol) of sodium borohydride in 500 mL of 0° C. water. The cold bath was removed, and the resulting mixture was stirred for 18 h. It was then diluted with 800 mL of ethyl acetate and 300 mL of saturated aqueous sodium bicarbonate. The two layers were separated, the aqueous layer was extracted with two 250 mL aliquots of ethyl acetate, and the extracts were combined with the original ethyl acetate layer. The combined ethyl acetate phase was washed with three 100 ml portions of saturated aqueous sodium bicarbonate, dried over magnesium sulfate, and concentrated under vacuum. The yellow oil was further purified by column chromatography on silica gel, eluting with 4:1 ethyl acetate:hexane to afford 37.70 g (68%) of benzyl (5S)-5-{[t-butyloxycarbonyl]amino}-6-hydroxyhexylcarbamate. $^1$H NMR (300 MHz, DMSO-$d_6$) δ 7.43-7.30 (m, 5H), 7.25 (t, J=5 Hz, 1H), 6.45 (d, J=8 Hz, 1H), 5.02 (s, 2H), 4.57 (br s, 1H), 3.35-3.29 (m overlapping water peak, 2H), 3.26-3.16 (m, 1H), 3.04-2.93 (m, 2H), 1.39 (s, 9H), 1.57-1.16 (m, 6H). ES-LCMS m/z 389 (M+Na).

Example 9b

Preparation of (2S)-6-{[(benzyloxy)carbonyl]amino}-2-[(tert-butoxycarbonyl)amino]hexanal

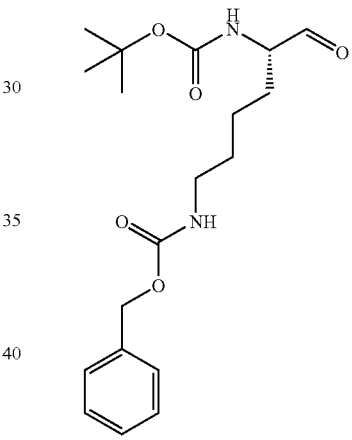

A solution of 53.0 g (333 mmol) of sulfur trioxide pyridine complex in 300 mL of dimethylsulfoxide was added to a solution of 8.64 g (34.4 mmol) of benzyl (5S)-5-{[t-butyloxycarbonyl]amino}-6-hydroxyhexylcarbamate and 14.4 mL (103 mmol) of triethylamine in 130 mL of dichloromethane at 0° C. The cold bath was removed, and the reaction mixture was stirred for 23 h. It was then poured slowly into a mixture of ice and 1 L of saturated aqueous sodium chloride. The resulting mixture was extracted with three 600 mL portions of ether. The ether extracts were then combined, washed with three 150 mL portions of saturated aqueous sodium chloride, and concentrated to 1.2 L. The concentrated ether phase was further washed with three 200 mL aliquots of 5% aqueous citric acid, and a 200 mL portion of saturated aqueous sodium chloride. After drying over magnesium sulfate, volatiles were removed under vacuum to afford 37.58 g (93%) of (2S)-6-{[(benzyloxy)carbonyl]amino}-2-[(tert-butoxycarbonyl)amino]hexanal. $^1$H NMR (300 MHz, DMSO-$d_6$) δ 9.44 (s, 1H), 7.46-7.23 (m, 6H), 5.02 (s, 2H), 3.85-3.75 (m, 1H), 3.07-2.93 (m, 2H), 1.77-1.60 (m, 1H), 1.56-1.23 (m, 5H), 1.41 (s, 9H).

Example 9c

Preparation of (2S)-6-{[(benzyloxy)carbonyl]amino}-2-[(tert-butoxycarbonyl)amino]-1-({[(1R)-1-phenylethyl]amino}carbonyl)hexyl benzoate

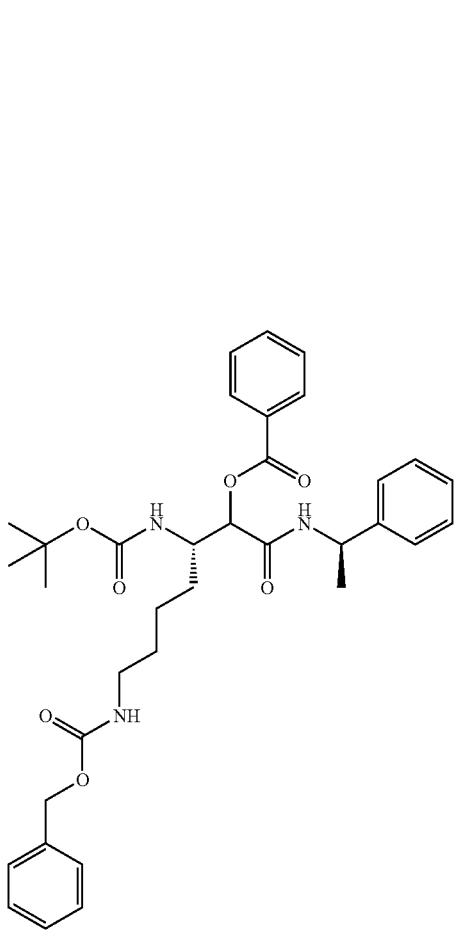

A solution of 9.6 g (73 mmol) of (1R)-α-methylbenzylisonitrile in 200 mL of dichloromethane was added to a solution of 355 mL (73.0 mmol) of 0.206 M (2S)-6-{[(benzyloxy)carbonyl]amino}-2-[(tert-butoxycarbonyl)amino]hexanal in dichloromethane. Then, 8.9 g (73 mL) of benzoic acid was added, and the resulting solution was stirred at room temperature for 18 h. Volatiles were then removed under vacuum, and the resulting yellow solid was further purified by column chromatography on silica gel. Elution with a gradient of 5-15% ether in dichloromethane afforded an oil, which was precipitated from hot ether with hexane to provide 28.03 g (62%) of (2S)-6-{[(benzyloxy)carbonyl]amino}-2-[(tert-butoxycarbonyl)amino]-1-({[(1R)-1-phenylethyl]amino}carbonyl)hexyl benzoate as a white solid, after drying under vacuum. $^1$H NMR (300 MHz, DMSO-d$_6$) δ 8.67 (d, J=8 Hz) and 8.58 (d, J=8 Hz) total 1H; 8.15 (d, J=7 Hz), 8.09 (d, J=8 Hz), and 7.97 (d, J=7 Hz) total 2H; 7.72-7.67 (m, 1H); 7.68-7.60 (m, 2H); 7.44-7.18 (m, 10H); 6.86 (d, J=10 Hz, 1H); 5.08-4.89 (m, 3H); 4.11-3.98 (m, 1H); 3.04-2.89 (m, 2H); 1.50-1.13 (m, 18H). ES-LCMS m/z 618 (M+H).

Example 9d

Preparation of tert-butyl (1S)-5-{[(benzyloxy)carbonyl]amino}-1-(1-hydroxy-2-oxo-2-{[(1R)-1-phenylethyl]amino}ethyl)pentylcarbamate

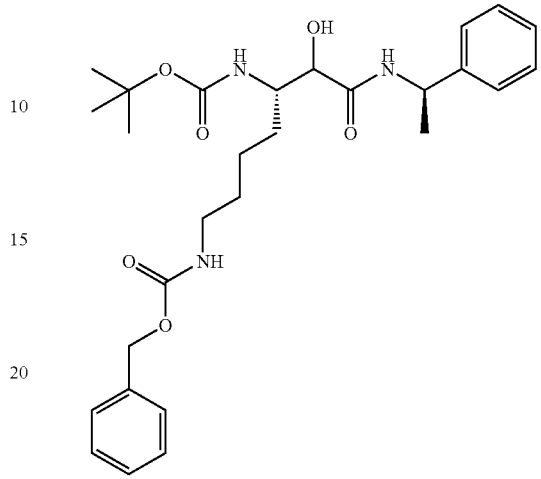

28.0 g (45.0 mmol) of (2S)-6-{[(Benzyloxy)carbonyl]amino}-2-[(tert-butoxycarbonyl)amino]-1-({[(1R)-1-phenylethyl]amino}carbonyl)hexyl benzoate was dissolved in 200 mL of dioxane, and a solution of 2.47 g (174 mmol) of lithium hydroxide in 100 mL of water was added. The resulting mixture was stirred for 24 h at room temperature. It was then diluted with 500 mL of ethyl acetate, and washed with 300 mL of 1N hydrochloric acid. The aqeous layer was back-extracted with two 100 mL portions of ethyl acetate. The extracts were then combined with the original ethyl acetate layer, washed with three 200 mL aliquots of saturated aqueous sodium bicarbonate, followed by 100 mL of saturated aqueous sodium chloride, and dried over magnesium sulfate. Volatiles were then removed under vacuum to afford 25.61 g (quantitative crude yield) of tert-butyl (1S)-5-{[(benzyloxy)carbonyl]amino}-1-(1-hydroxy-2-oxo-2-{[(1R)-1-phenylethyl]amino}ethyl)pentylcarbamate as a waxy light yellow solid. $^1$H NMR (300 MHz, DMSO-d$_6$) δ 7.98-7.88 (m, 1H); 7.68-7.63 (m) and 7.49-7.42 (m) total 1H; 7.35-7.10 (m, 10H); 6.31 (d, J=9 Hz) and 6.02 (d, J=9 Hz) total 1H; 5.62-5.53 (br s) and 5.53-5.42 (br s) total 1H; 4.94 (s, 2H), 4.91-4.83 (m, 1H); 3.87 (br s) and 3.79 (br s) total 1H; 3.72-3.58 (m, 1H); 2.99-2.76 (m, 2H); 1.47-1.10 (m, 18H). ES-LCMS m/z 514 (M+H).

Example 9e

Preparation of tert-butyl (1S)-5-amino-1-(1-hydroxy-2-oxo-2-{[(1R)-1-phenylethyl]amino}ethyl)pentylcarbamate

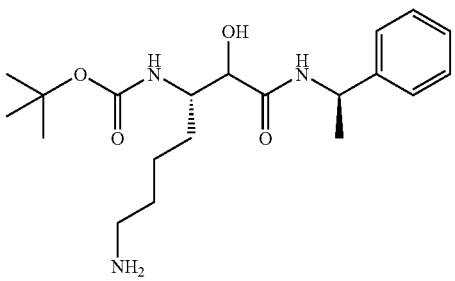

A slurry of 1.5 g of 10 wt % palladium on carbon in 3 mL of water was added to a solution of 15.28 g (29.70 mmol) of tert-butyl (1S)-5-{[(benzyloxy)carbonyl]amino}-1-(1-hydroxy-2-oxo-2-{[(1R)-1-phenylethyl]amino}ethyl)pentylcarbamate in 200 mL of ethanol. The resulting slurry was stirred vigorously under 45 psi of hydrogen gas at 50° C. for 18 h. The catalyst was then filtered off, rinsing with 400 mL of ethanol. Concentration of the filtrate under vacuum afforded 10.52 g (93%) of tert-butyl (1S)-5-amino-1-(1-hydroxy-2-oxo-2-{[(1R)-1-phenylethyl]amino}ethyl)pentylcarbamate as a colorless oil that crystallized upon standing under vacuum. $^1$H NMR (300 MHz, DMSO-$d_6$) δ 8.15 (d, J=8 Hz) and 8.08 (d, J=8 Hz) total 1H; 7.90-7.87 (m, ca 1H); 7.87-7.28 (m, 4H); 7.25-7.20 (m, 1H); 6.51 (d, J=9 Hz) and 6.17 (d, J=9 Hz) total 1H; 4.99-4.92 (m, 1H); 3.96 (d, J=4 Hz) and 3.90 (d, J=3 Hz) total 1H; 3.80-3.69 (m, 1H); 2.68-2.64 (m) and 2.53-2.57 (m) total 1H; 1.53-1.23 (m, 18H). ES-LCMS m/z 380 (M+H).

Example 9f

Preparation of tert-butyl (1S)-1-(1-hydroxy-2-oxo-2-{[(1R)-1-phenylethyl]amino}ethyl)-5-[(4-morpholinylcarbonyl)amino]pentylcarbamate

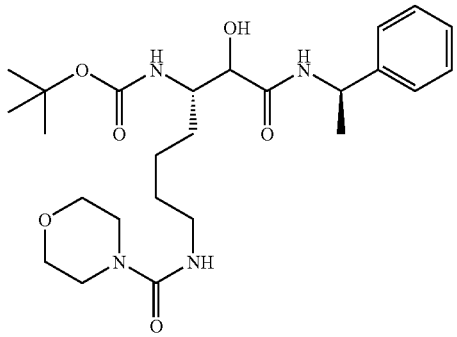

To a slurry of 1.04 g (2.7 mmol) of tert-butyl (1S)-5-amino-1-(1-hydroxy-2-oxo-2-{[(1R)-1-phenylethyl]amino}ethyl)pentylcarbamate and 0.38 mL (2.7 mmol) of trietylamine in 45 mL of dioxane was added 0.24 mL (2.7 mmol) of 4-morpholinecarbonyl chloride. The flask was heated with a heat gun until the mixture became homogeneous and was stirred at room temperature for 5 d. The reaction was concentrated under reduced pressure and the residue was purified by silica gel chromatography eluting with 6:4 acetone:hexanes to afford 1.05 g (78%) of tert-butyl (1S)-1-(1-hydroxy-2-oxo-2-{[(1R)-1-phenylethyl]amino}ethyl)-5-[(4-morpholinylcarbonyl)amino]pentylcarbamate. $^1$H NMR (400 MHz, DMSO-$d_6$) δ 7.95 (m, 1H), 7.27 (m, 4H), 7.16 (m, 1H), 6.41 (m, 1H), 6.01 (d, J=9 Hz, 1H), 5.47 (d, J=6 Hz, 1H), 4.87 (qnt, J=7 Hz, 1H), 3.80 (dd, J=3 Hz, J=6 Hz, 1H), 3.65 (m, 1H), 3.46 (t, J=5 Hz, 4H), 3.16 (t, J=5 Hz, 4H), 2.93 (q, J=6 Hz, 2H), 1.13-1.44 (m, 18H). ES-LCMS m/z 493 (M+H).

Example 9g

Preparation of (1-benzylcyclohexyl)methanol

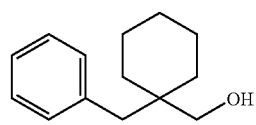

(1-Benzylcyclohexyl)methanol was prepared as in example 5f except that methyl 1-benzylcyclohexanecarboxylate was substituted for ethyl cyclobutanecarboxylate. $^1$H NMR (300 MHz, DMSO-$d_6$) δ 7.12-7.28 (m, 5H), 4.46 (t, J=5 Hz, 1H), 3.06 (d, J=5 Hz, 2H), 2.55 (s, 2H), 1.10-1.55 (m, 10H).

Example 9h

Preparation of N-((5S)-5-amino-6-hydroxy-7-oxo-7-{[(1R)-1-phenylethyl]amino}heptyl)-4-morpholinecarboxamide hydrochloride

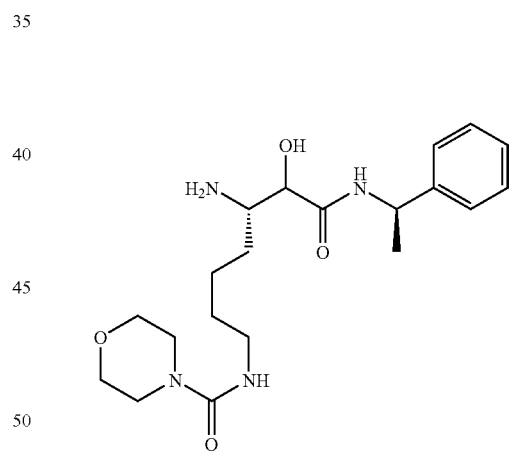

A solution of 830 mg (1.7 mmol) of tert-butyl (1S)-1-(1-hydroxy-2-oxo-2-{[(1R)-1-phenylethyl]amino}ethyl)-5-[(4-morpholinylcarbonyl)amino]pentylcarbamate in 100 mL of ethyl acetate was bubbled with hydrogen chloride gas for 5 min and the reaction allowed to stir for 10 min before being conentrated under reduced pressure to afford 720 mg (>99%) of N-((5S)-5-amino-6-hydroxy-7-oxo-7-{[(1R)-1-phenylethyl]amino}heptyl)-4-morpholinecarboxamide hydrochloride. $^1$H NMR (300 MHz, DMSO-$d_6$) δ 8.46 (d, J=8 Hz, 1H), 7.97 (m, 1H), 7.82 (m, 2H), 7.31 (m, 4H), 7.22 (m, 1H), 6.50 (m, 1H), 4.94 (qnt, 1H), 3.83 under water peak (m, 2H), 3.50 (t, J=5 Hz, 4H), 3.22 (t, J=5 Hz, 4H), 2.98 (m, 2H), 1.20-1.61 (m, 9H). ES-LCMS m/z 393 (M+H).

Example 9i

Preparation of (1-benzylcyclohexyl)methyl(1S)-1-(1-hydroxy-2-oxo-2-{[(1R)-1-phenylethyl]amino}ethyl)-5-[(4-morpholinylcarbonyl)amino]pentylcarbamate

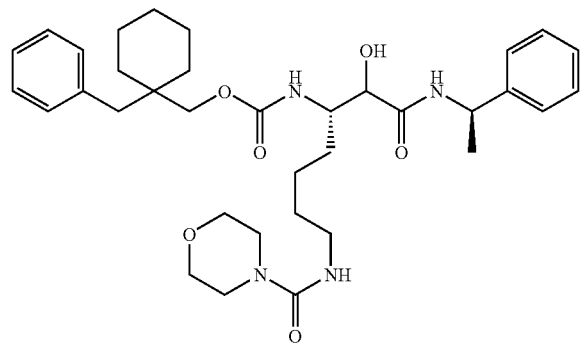

To a solution of 63 mg (0.31 mmol) of (1-benzylcyclohexyl)methanol in 1 mL of tetrahydrofuran was added 0.32 mL (0.62 mmol) of 1.93 M phosgene in toluene. The reaction was stirred at room temperature for 18 h, quenched with a stream of nitrogen gas for 5 min, and concentrated under reduced pressure. The resulting liquid was added to a solution of 133 mg (0.31 mmol) of N-((5S)-5-amino-6-hydroxy-7-oxo-7-{[(1R)-1-phenylethyl]amino}heptyl)-4-morpholinecarboxamide hydrochloride and 0.095 mL (0.68 mmol) of triethylamine in 2 mL of methanol. The reaction was stirred at room temperature for 24 h and concentrated under reduced pressure. The residue was purified by silica chromatography eluting with 6:4 acetone:hexanes to afford 110 mg (57%) of (1-benzylcyclohexyl)methyl(1S)-1-(1-hydroxy-2-oxo-2-{[(1R)-1-phenylethyl]amino}ethyl)-5-[(4-morpholinylcarbonyl)amino]pentylcarbamate. $^1$H NMR (400 MHz, DMSO-$d_6$) δ 7.96 (m, 1H), 7.06-7.29 (m, 10H), 6.53 (d, J=9 Hz, 1H), 6.41 (m, 1H), 5.56-5.75 (m, 1H), 4.88 (qnt, J=7 Hz, 1H), 3.88 (m, 1H), 3.73 (m, 1H), 3.51 (m, 2H), 3.45 (t, J=4 Hz, 4H), 3.16 (t, J=4 Hz, 4H), 2.96 (m, 2H), 2.57 (s, 2H), 1.17-1.54 (m, 19H). ES-LCMS m/z 645 (M+Na).

Example 9j

Preparation of (1-benzylcyclohexyl)methyl(1S)-5-[(4-morpholinylcarbonyl)amino]-1-(oxo{[(1R)-1-phenylethyl]amino}acetyl)pentylcarbamate

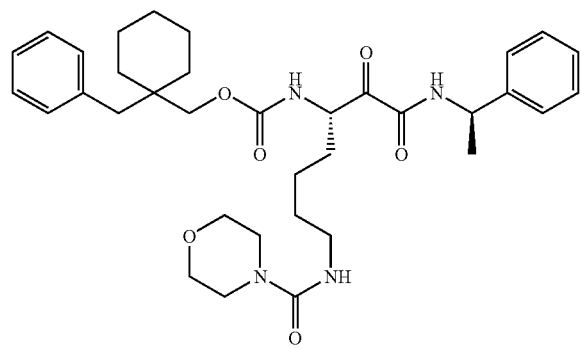

To a −60° C. solution of 0.034 mL (0.39 mmol) of oxalyl chloride in 1 mL of dichloromethane was added 0.055 mL (0.78 mmol) of dimethylsulfoxide, dropwise. A solution of 110 mg (0.177 mmol) of (1-benzylcyclohexyl)methyl(1S)-1-(1-hydroxy-2-oxo-2-{[(1R)-1-phenylethyl]amino}ethyl)-5-[(4-morpholinylcarbonyl)amino]pentylcarbamate in 1 mL of dichloromethane was added dropwise and the reaction stirred for 10 min before 0.12 mL (0.89 mmol) of triethylamine was added dropwise. The reaction was let warm to room temperature and stirred for 15 min before being applied directly to a silica gel column eluting with 3:7 acetone:dichloromethane to afford 90 mg (82%) of (1-benzylcyclohexyl)methyl(1S)-5-[(4-morpholinylcarbonyl)amino]-1-(oxo{[(1R)-1-phenylethyl]amino}acetyl)pentylcarbamate. $^1$H NMR (300 MHz, 80° C., DMSO-$d_6$) δ 8.91 (m, 1H), 7.15-7.38 (m, 11H), 6.30 (m, 1H) 5.01 (qnt, J=7 Hz, 1H), 4.85 (m, 1H), 3.63-3.72 (m, 2H), 3.54 (t, J=5 Hz, 4H), 3.26 (t, J=5 Hz, 4H), 3.04 (m, 2H), 2.66 (s, 2H), 1.316-1.714 (m, 19H). ES-LCMS m/z 643 (M+Na). HRMS $C_{35}H_{48}N_4O_6$ m/z 621.3652 (M+H)$_{Cal}$; 621.3641 (M+Na)$_{Obs}$.

Example 10

[1-(4-Fluorobenzyl)cyclobutyl]methyl(1S)-5-[(4-morpholinylcarbonyl)amino]-1-(oxo{[(1R)-1-phenylethyl]amino}acetyl)pentylcarbamate

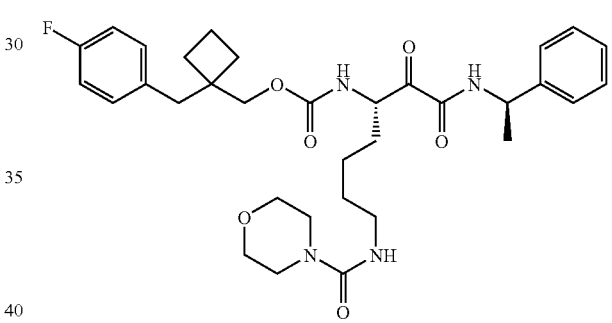

Example 10a

Preparation of [1-(4-fluorobenzyl)cyclobutyl]methanol

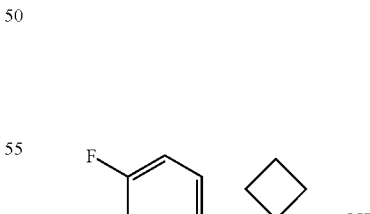

[1-(4-Fluorobenzyl)cyclobutyl]methanol was prepared as in example 5f except that 4-fluorobenzyl bromide was substituted for benzyl bromide. $^1$H NMR (300 MHz, DMSO-$d_6$) δ 7.20 (m, 2H), 7.06 (t, J=9 Hz, 2H), 4.61 (t, J=5 Hz, 1H), 3.19 (d, J=5 Hz, 2H), 2.67 (s, 2H), 1.62-1.75 (m, 6H).

Example 10b

Preparation of [1-(4-fluorobenzyl)cyclobutyl]methyl (1S)-1-(1-hydroxy-2-oxo-2-{[(1R)-1-phenylethyl]amino}ethyl)-5-[(4-morpholinylcarbonyl)amino]pentylcarbamate

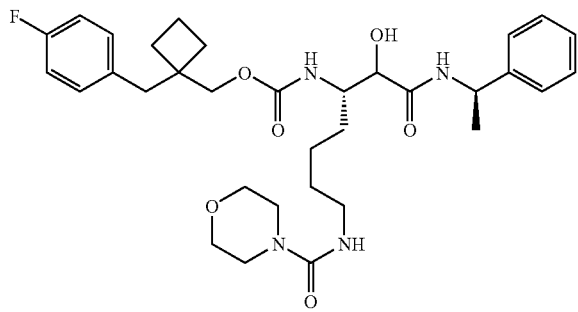

[1-(4-Fluorobenzyl)cyclobutyl]methyl(1S)-1-(1-hydroxy-2-oxo-2-{[(1R)-1-phenylethyl]amino}ethyl)-5-[(4-morpholinylcarbonyl)amino]pentylcarbamate was prepared as in example 9i except that [1-(4-fluorobenzyl)cyclobutyl]methanol was substituted for (1-benzylcyclohexyl)methanol. $^1$H NMR (300 MHz, DMSO-$d_6$) δ 7.98 (m, 1H), 7.21-7.28 (m, 4H), 7.12-718 (m, 3H), 7.02 (q, J=8 Hz, 2H), 6.51 (d, J=9 Hz, 1H), 6.42 (m, 1H), 5.53 (m, 1H), 4.88 (qnt, J=7 Hz, 1H), 3.84 (bs, 1H), 3.64-3.77 (m, 3H), 3.45 (t, J=5 Hz, 4H), 3.16 (t, J=5 Hz, 4H), 2.95 (m, 2H), 2.69 (s, 2H), 1.60-1.85 (m, 6H), 1.15-1.50 (m, 9H). ES-LCMS m/z 635 (M+Na).

Example 10c

Preparation of [1-(4-fluorobenzyl)cyclobutyl]methyl (1S)-5-[(4-morpholinylcarbonyl)amino]-1-(oxo{[(1R)-1-phenylethyl]amino}acetyl)pentylcarbamte

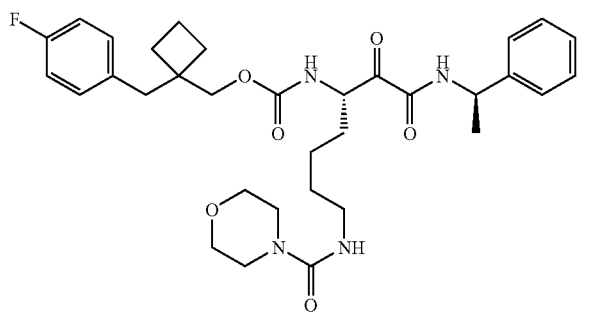

[1-(4-Fluorobenzyl)cyclobutyl]methyl(1S)-5-[(4-morpholinylcarbonyl)amino]-1-(oxo{[(1R)-1-phenylethyl]amino}acetyl)pentylcarbamate was prepared as in example 9j except that [1-(4-fluorobenzyl)cyclobutyl]methyl(1S)-1-(1-hydroxy-2-oxo-2-{[(1R)-1-phenylethyl]amino}ethyl)-5-[(4-morpholinylcarbonyl)amino]pentylcarbamate was substituted for (1-benzylcyclohexyl)methyl(1S)-1-(1-hydroxy-2-oxo-2-{[(1R)-1-phenylethyl]amino}ethyl)-5-[(4-morpholinylcarbonyl)amino]pentylcarbamate. $^1$H NMR (300 MHz, 80° C., DMSO-$d_6$) δ 8.90 (d, J=7 Hz, 1H), 7.07-7.38 (m, 10H), 6.28 (m, 1H), 5.01 (qnt, J=7 Hz, 1H), 4.83 (m, 1H), 3.81 (s, 2H), 3.54 (m, 4H), 3.26 (m, 4H), 3.04 (m, 2H), 2.77 (s, 2H), 1.80-1.90 (m, 6H), 1.19-1.48 (m, 9H). ES-LCMS m/z 633 (M+Na). HRMS $C_{33}H_{43}N_4O_6F_1$ m/z 633.3064 (M+Na)$_{Cal}$; 633.3072 (M+Na)$_{Obs}$.

Example 11

[1-(4-Pyridinylmethyl)cyclobutyl]methyl(1S)-5-[(4-morpholinylcarbonyl)amino]-1-(oxo{[(1R)-1-phenylethyl]amino}acetyl)pentylcarbamate

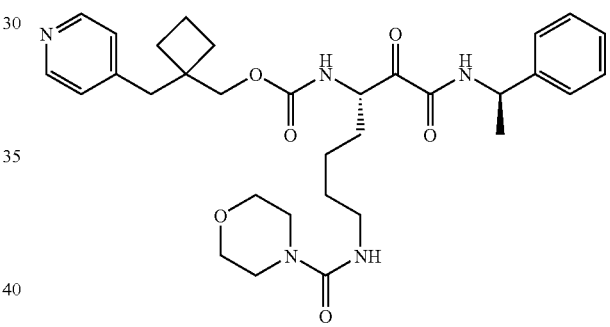

Example 11a

Preparation of [1-(4-pyridinylmethyl)cyclobutyl]methanol

[1-(4-Pyridinylmethyl)cyclobutyl]methanol was prepared as in example 5f except that 4-picolyl chloride was substituted for benzyl bromide. $^1$H NMR (300 MHz, DMSO-$d_6$) δ 8.46 (d, J=6 Hz, 2H), 7.23 (d, J=6 Hz, 2H), 4.74 (t, J=5 Hz, 1H), 3.24 (d, J=5 Hz, 2H), 2.74 (s, 2H), 1.67-1.85 (m, 6H).

Example 11b

Preparation of [1-(4-pyridinylmethyl)cyclobutyl]methyl(1S)-1-(1-hydroxy-2-oxo-2-{[(1R)-1-phenylethyl]amino}ethyl)-5-[(4-morpholinylcarbonyl)amino]pentylcarbamate

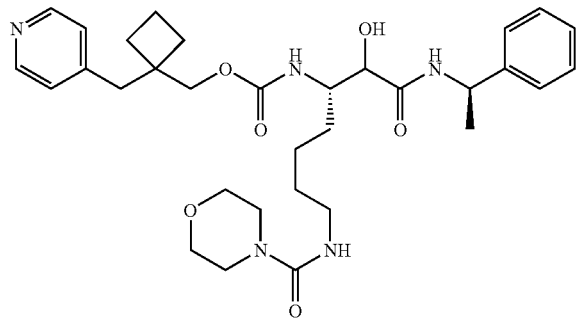

[1-(4-Pyridinylmethyl)cyclobutyl]methyl(1S)-1-(1-hydroxy-2-oxo-2-{[(1R)-1-phenylethyl]amino}ethyl)-5-[(4-morpholinylcarbonyl)amino]pentylcarbamate was prepared as in example 9i except that [1-(4-pyridinylmethyl)cyclobutyl]methanol was substituted for (1-benzylcyclohexyl)methanol. Product was carried forward without purification or characterization.

Example 11c

Preparation of [1-(4-pyridinylmethyl)cyclobutyl]methyl(1S)-5-[(4-morpholinylcarbonyl)amino]-1-(oxo{[(1R)-1-phenylethyl]amino}acetyl)pentylcarbamate

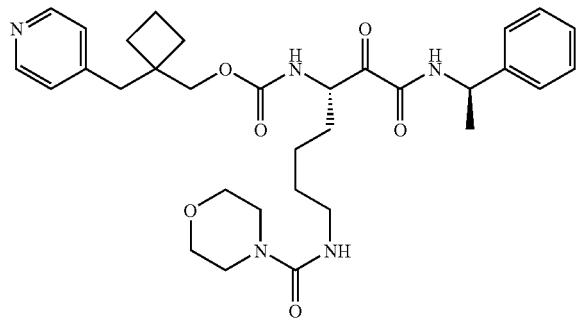

[1-(4-Pyridinylmethyl)cyclobutyl]methyl(1S)-5-[(4-morpholinylcarbonyl)amino]-1-(oxo{[(1R)-1-phenylethyl]amino}acetyl)pentylcarbamate was prepared as in example 9j except that [1-(4-pyridinylmethyl)cyclobutyl]methyl(1S)-1-(1-hydroxy-2-oxo-2-{[(1R)-1-phenylethyl]amino}ethyl)-5-[(4-morpholinylcarbonyl)amino]pentylcarbamate was substituted for (1-benzylcyclohexyl)methyl(1S)-1-(1-hydroxy-2-oxo-2-{[(1R)-1-phenylethyl]amino}ethyl)-5-[(4-morpholinylcarbonyl)amino]pentylcarbamate. $^1$H NMR (300 MHz, 80° C., DMSO-$d_6$) δ 8.92 (m, 1H), 8.49 (m, 2H), 7.20-7.36 (m, 8H), 6.31 (m, 1H), 5.01 (qnt, J=7 Hz, 1H), 4.82 (m, 1H), 3.78 (s, 2H), 3.53 (t, J=5 Hz, 4H), 3.24 (t, J=5 Hz, 4H), 3.01 (m, 2H), 2.80 (s, 2H), 1.83-1.90 (m, 6H), 1.42-1.48 (m, 9H). ES-LCMS m/z 594 (M+H). HRMS $C_{32}H_{43}N_5O_6$ m/z 594.3291 (M+H)$_{Cal}$; 594.3279 (M+Na)$_{Obs}$.

Example 12

[1-(3-Pyridinylmethyl)cyclobutyl]methyl(1S)-5-[(4-morpholinylcarbonyl)amino]-1-(oxo{[(1R)-1-phenylethyl]amino}acetyl)pentylcarbamate

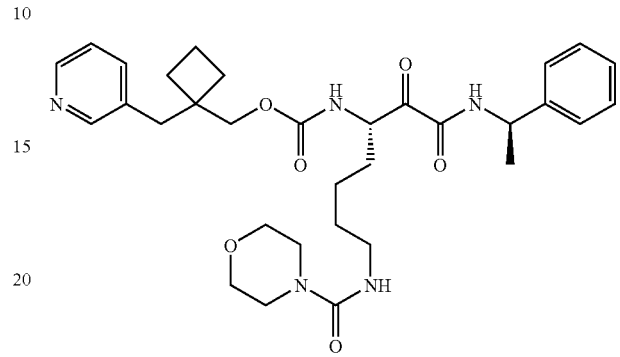

Example 12a

Preparation of [1-(3-pyridinylmethyl)cyclobutyl]methanol

[1-(3-Pyridinylmethyl)cyclobutyl]methanol was prepared as in example 5f except that 3-picolyl chloride was substituted for benzyl bromide. $^1$H NMR (300 MHz, DMSO-$d_6$) δ 8.42 (bs, 2H), 7.62 (d, J=8 Hz, 1H), 7.31 (dd, J=5 Hz, J=8 Hz, 1H), 4.72 (t, J=5 Hz, 1H), 3.22 (d, J=5 Hz, 2H), 2.73 (s, 2H), 1.65-1.81 (m, 6H).

Example 12b

Preparation of [1-(3-pyridinylmethyl)cyclobutyl]methyl(1S)-1-(1-hydroxy-2-oxo-2-{[(1R)-1-phenylethyl]amino}ethyl)-5-[(4-morpholinylcarbonyl)amino]pentylcarbamate

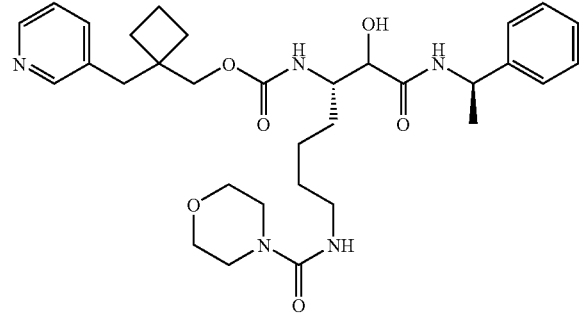

[1-(3-Pyridinylmethyl)cyclobutyl]methyl(1S)-1-(1-hydroxy-2-oxo-2-{[(1R)-1-phenylethyl]amino}ethyl)-5-[(4-morpholinylcarbonyl)amino]pentylcarbamate was prepared as in example 9i except that[1-(3-pyridinylmethyl)cyclobutyl]methanol was substituted for (1-benzylcyclohexyl)methanol. $^1$H NMR (300 MHz, DMSO-d$_6$) δ 8.35 (s, 2H), 7.96 (d, J=8 Hz, 1H), 7.53 (d, J=8 Hz, 1H), 7.21-7.29 (m, 5H), 7.15 (t, J=7 Hz, 1H), 6.54 (d, J=9 Hz, 1H), 6.43 (m, 1H), 5.55 (d, J=6 Hz, 1H), 4.88 (qnt, J=7 Hz, 1H), 3.85 (dd, J=3 Hz, J=6 Hz, 1H), 3.66-3.77 (m, 3H), 3.45 (t, J=5 Hz, 4H), 3.16 (t, J=5 Hz, 4H), 2.95 (m, 2H), 2.71 (s, 2H), 1.63-1.87 (m, 6H), 1.15-1.50 (m, 9H). ES-LCMS m/z 596 (M+H).

Example 12c

Preparation of [1-(3-pyridinylmethyl)cyclobutyl]methyl(1S)-5-[(4-morpholinylcarbonyl)amino]-1-(oxo{[(1R)-1-phenylethyl]amino}acetyl)pentylcarbamate

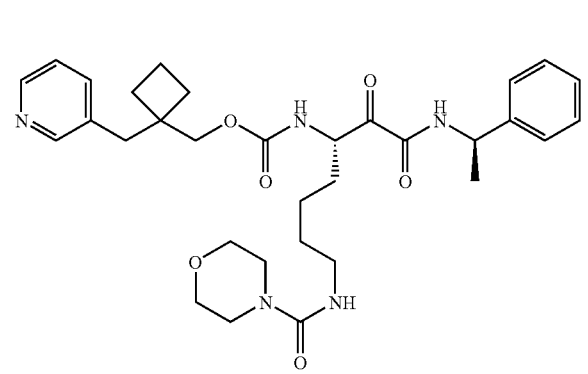

[1-(3-Pyridinylmethyl)cyclobutyl]methyl(1S)-5-[(4-morpholinylcarbonyl)amino]-1-(oxo{[(1R)-1-phenylethyl]amino}acetyl)pentylcarbamate was prepared as in example 9j except that [1-(3-pyridinylmethyl)cyclobutyl]methyl(1S)-1-(1-hydroxy-2-oxo-2-{[(1R)-1-phenylethyl]amino}ethyl)-5-[(4-morpholinylcarbonyl)amino]pentylcarbamate was substituted for (1-benzylcyclohexyl)methyl(1S)-1-(1-hydroxy-2-oxo-2-{[(1R)-1-phenylethyl]amino}ethyl)-5-[(4-morpholinylcarbonyl)amino]pentylcarbamate. ES-LCMS m/z 616 (M+Na). Retention time=2.94 min. LC-MS results obtained using a Phenomenex max RP 50×2 MM column with 4 u packing eluted at 0.8 mL/min with a 5 minute gradient from 85% water: 15% methanol to 100% methanol. The mobile phase contained a 0.1% formic acid modifier. HRMS C$_{32}$H$_{43}$N$_5$O$_6$ m/z 594.3292 (M+Na)$_{Cal}$; 594.3279 (M+Na)$_{Obs}$.

Example 13

[1-(2,6-Difluorobenzyl)cyclobutyl]methyl(1S)-5-{[(methylamino)carbonyl]amino}-1-(oxo{[(1R)-1-phenylethyl]amino}acetyl)pentylcarbamate

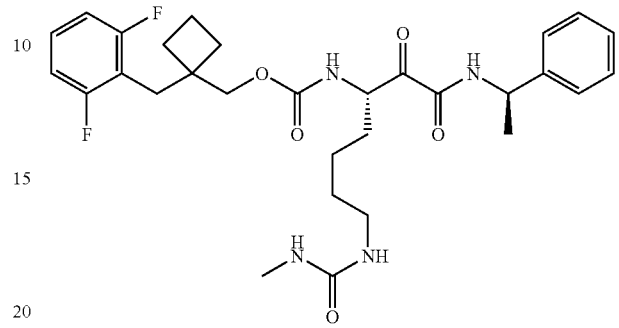

Example 13a

Preparation of tert-butyl (1S)-1-(1-hydroxy-2-oxo-2-{[(1R)-1-phenylethyl]amino}ethyl)-5-{[(methylamino)carbonyl]amino}pentylcarbamate

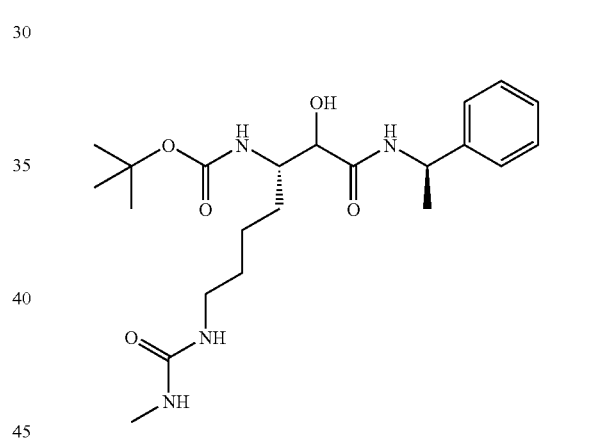

0.472 mL (8.00 mmol) of methylisocyanate was added to a slurry of 3.03 g (8.00 mmol) of tert-butyl (1S)-5-amino-1-1-(1-hydroxy-2-oxo-2-{[(1R)-1-phenylethyl]amino}ethyl)pentylcarbamate at 0° C. in 60 mL of anhydrous tetrahydrofuran under nitrogen. The mixture was stirred at 0° C. for 1 h, during which time all solids dissolved. The cold bath was then removed, and the solution was stirred overnight. Volatiles were removed under vacuum, and the resulting foam was further purified by column chromatography on silica gel. Elution with a gradient from 50% to 75% acetone in hexane afforded 3.00 g (86%) of tert-butyl (1S)-1-(1-hydroxy-2-oxo-2-{[(1R)-1-phenylethyl]amino}ethyl)-5-{[(methylamino)carbonyl]amino}pentylcarbamate as a white solid after drying under vacuum. $^1$H NMR (300 MHz, DMSO-d$_6$) δ 8.06-8.01 (m, 1H); 7.38-7.18 (m, 5H); 6.40 (d, J=10 Hz) and 6.08 (d, J=9 Hz) total 1H; 5.86-5.75 (m, 1H); 5.71-5.51 (m, 2H); 5.01-4.91 (m, 1H); 3.94 (br s) and 3.87 (br s) total 1H; 3.79-3.64 (m, 1H); 3.01-2.81 (m, 2H); 2.54 (d, J=5 Hz, 3H); 1.52-1.16 (m, 18H). ES-LCMS m/z 437 (M+H).

Example 13b

Preparation of (3S)-3-amino-2-hydroxy-7-{[(methylamino)carbonyl]amino}-N-[(1R)-1-phenylethyl]heptanamide hydrochloride

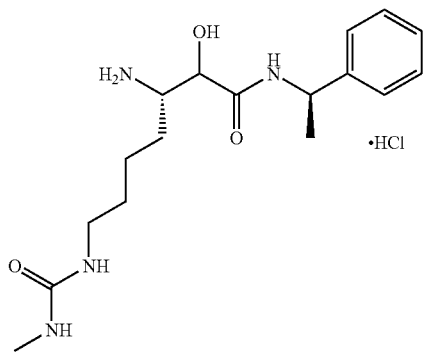

A solution of 2.86 g (6.55 mmol) of tert-butyl (1S)-1-(1-hydroxy-2-oxo-2-{[(1R)-1-phenylethyl]amino}ethyl)-5-{[(methylamino)carbonyl]amino}pentylcarbamate in 200 mL of ethyl acetate and 50 mL of methanol was cooled to 0° C., and saturated with hydrogen chloride by bubbling anhydrous hydrogen chloride through it for 7 min. The resulting solution was stirred for 1.5 h. Volatiles were then removed, and the resulting oil was dried further under vacuum to afford 2.74 g (quantitative yield) of (3S)-3-amino-2-hydroxy-7-{[(methylamino)carbonyl]amino}-N-[(1R)-1-phenylethyl]heptanamide hydrochloride as a solid foam containing ethanol (0.53 eq based on integration of signals in the $^1$H NMR spectrum). $^1$H NMR (300 MHz, DMSO-$d_6$) δ 8.56 (d, J=8 Hz) and 8.45 (d, J=8 Hz) total 1H; 8.14 (br s) and 7.95 (br s) total 3H; 7.39-7.18 (m, 5H); 7.16-6.50 (br s, ca 3H); 5.02-4.91 (m, 1H); 4.30 (br s) and 4.09 (d, J=5 Hz) total 1H; 3.38-3.17 (m, 1H); 3.02-2.82 (m, 2H); 2.55 (s, 3H); 1.63-1.15 (m, 6H); 1.44 (s, 3H). ES-LCMS m/z 337 (M+H).

Example 13c

Preparation of [1-(2,6-difluorobenzyl)cyclobutyl]methanol

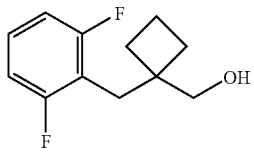

[1-(2,6-Difluorobenzyl)cyclobutyl]methanol was prepared as in example 5f except that 2,6-difluorobenzyl bromide was substituted for benzyl bromide. $^1$H NMR (300 MHz, DMSO-$d_6$) δ 7.30-7.41 (m, 1H), 7.00-7.16 (m, 2H), 4.76 (t, J=5 Hz, 1H), 3.39 (d, J=2H), 2.72 (s, 2H), 1.54-1.80 (m, 6H).

Example 13d

Preparation of [1-(2,6-difluorobenzyl)cyclobutyl]methyl(1S)-1-(1-hydroxy-2-oxo-2-{[(1R)-1-phenylethyl]amino}ethyl)-5-{[(methylamino)carbonyl]amino}pentylcarbamate

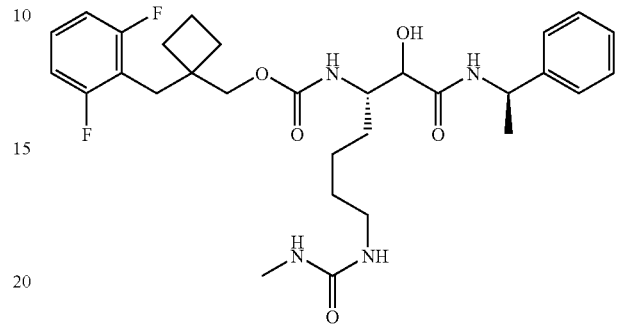

[1-(2,6-Difluorobenzyl)cyclobutyl]methyl(1S)-1-(1-hydroxy-2-oxo-2-{[(1R)-1-phenylethyl]amino}ethyl)-5-{[(methylamino)carbonyl]amino}pentylcarbamate was prepared as in example 9i except that [1-(2,6-difluorobenzyl)cyclobutyl]methanol was substituted for (1-benzylcyclohexyl)methanol, and (3S)-3-amino-2-hydroxy-7-{[(methylamino)carbonyl]amino}-N-[(1R)-1-phenylethyl]heptanamide hydrochloride was substituted for N-((5S)-5-amino-6-hydroxy-7-oxo-7-{[(1R)-1-phenylethyl]amino}heptyl)-4-morpholinecarboxamide hydrochloride. $^1$H NMR (300 MHz, DMSO-$d_6$) δ 8.06 (m, 1H), 7.01-7.45 (m, 8H), 6.43 (d, J=8 Hz, 1H), 5.83 (m, 1H), 5.60 (m, 2H), 4.94 (m, 1H), 3.70-4.00 (m, 4H), 3.35 under water peak (m, 3H), 2.65-3.00 (m, 4H), 1.60-1.85 (m, 6H), 1.10-1.50 (m, 9H). ES-LCMS m/z 573 (M−H).

Example 13e

Preparation of [1-(2,6-difluorobenzyl)cyclobutyl]methyl(1S)-5-{[(methylamino)carbonyl]amino}-1-(oxo{[(1R)-1-phenylethyl]amino}acetyl)pentylcarbamate

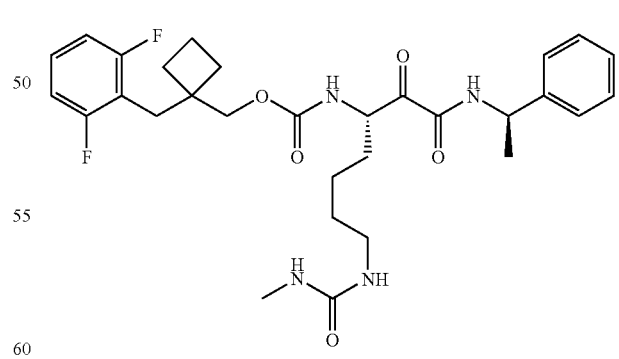

[1-(2,6-Difluorobenzyl)cyclobutyl]methyl(1S)-5-{[(methylamino)carbonyl]amino}-1-(oxo{[(1R)-1-phenylethyl]amino}acetyl)pentylcarbamate was prepared as in example 9j except that [1-(2,6-difluorobenzyl)cyclobutyl]methyl(1S)-1-(1-hydroxy-2-oxo-2-{[(1R)-1-phenylethyl]amino}ethyl)-5-{[(methylamino)carbonyl]

amino}pentylcarbamate was substituted for (1-benzylcyclohexyl)methyl(1S)-1-(1-hydroxy-2-oxo-2-{[(1R)-1-phenylethyl]amino}ethyl)-5-[(4-morpholinylcarbonyl)amino]pentylcarbamate. $^1$H NMR (300 MHz, DMSO-d$_6$) δ 9.19 (m, 1H), 7.58 (m, 1H), 7.05-7.43 (m, 8H), 5.86 (m, 1H), 5.65 (m, 1H), 4.98 (m, 1H), 4.76 (m, 1H), 3.95 (m, 2H). 3.25 under water peak (m, 3H), 2.96 (m, 2H), 2.78 (s, 2H), 1.60-1.90 (m, 6H), 1.25-1.50 (m, 9H). ES-LCMS m/z 571 (M–H).

Example 14

[1-(4-Fluorobenzyl)cyclobutyl]methyl(1S)-1-[oxo(1H-pyrazol-5-ylamino)acetyl]pentylcarbamate

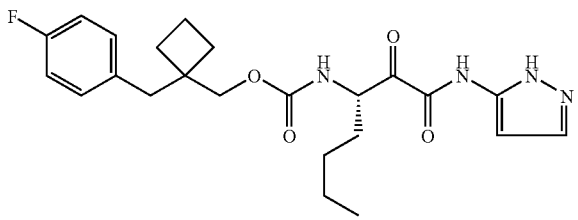

Example 14a

Preparation of methyl(2S)-2-[({[1-(4-fluorobenzyl)cyclobutyl]methoxy}carbonyl)amino]hexanoate

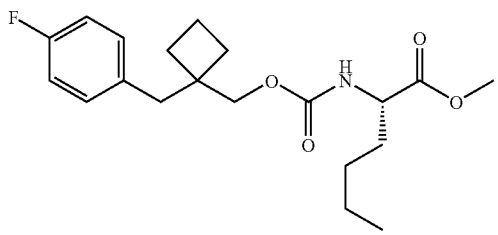

To a solution of 430 mg (2.2 mmol) of [1-(4-fluorobenzyl)cyclobutyl]methanol in 10 mL of tetrahydrofuran was added 2.4 mL (4.65 mmol) of 1.93 M phosgene in toluene and the reaction stirred for 18 h at room temperature. The solution was concentrated and the resulting liquid added to a suspension of 380 mg (2.1 mmol) of methyl(2S-2-aminohexanoate and 1.09 mL (6.3 mmol) of N,N-diisopropylethylamine in 10 mL of dioxane. The mixture was stirred at room temperature for 5 h before being diluted with water and extracted with ethyl acetate. The combined ethyl acetate layers were washed with water, dried over magnesium sulfate, and concentrated to give 760 mg (99%) of methyl (2S)-2-[({[1-(4-fluorobenzyl)cyclobutyl]methoxy}carbonyl)amino]hexanoate. $^1$H NMR (300 MHz, DMSO-d$_6$) δ 7.67 (d, J=8 Hz, 1H), 7.07-7.25 (m, 4H), 4.00 (m, 1H), 3.77 (s, 2H), 3.65 (s, 3H), 2.77 (s, 2H), 1.60-1.94 (m, 8H), 1.20-1.40 (m, 4H), 0.88 (t, J=7 Hz, 3H).

Example 14b

Preparation of [1-(4-fluorobenzyl)cyclobutyl]methyl (1S)-1-[cyano(triphenylphosphoranylidene)acetyl]pentylcarbamate

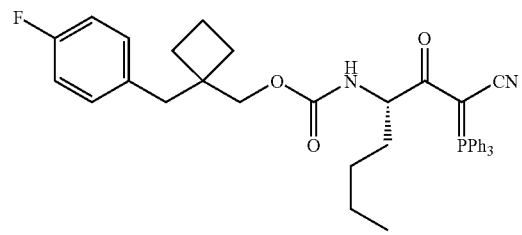

To a solution of 760 mg (2.1 mmol) of methyl(2S)-2-[({[1-(4-fluorobenzyl)cyclobutyl]methoxy}carbonyl) amino]hexanoate in 5 mL of tetrahydrofuran was added a solution of 105 mg (2.5 mmol) of lithium hydroxide monohydrate in 5 mL of water. The reaction was heated briefly to promote homogeneity and then let stir at room temperature for 18 h. The reaction was diluted with water, acidified with iced 1M hydrochloric acid, extracted with ethyl acetate, dried over magnesium sulfate, and concentrated under reduced pressure. The resulting carboxylic acid was dissolved in 50 mL of dichloromethane before 630 mg (2.1 mmol) of (triphenylphosphoranylidene) acetonitrile was added. The mixture was cooled to 0° C. before a catalytic amount of N,N-dimethylaminopyridine was added followed by 400 mg (2.1 mmol) of 1-(3-dimethylaminopropyl)-3-ethylcarbodiimide hydrochloride. The reaction was allowed to warm to room temperature and stirred for 18 h. The mixture was concentrated under reduced pressure and the residue was purified by silica gel chromatography eluting with 1:9 ethyl acetate:dichloromethane to afford 400 mg (300%) of [1-(4-fluorobenzyl)cyclobutyl]methyl(1S)-1-[cyano(triphenylphosphoranylidene)acetyl]pentylcarbamate. $^1$H NMR (300 MHz, DMSO-d$_6$) δ 7.75 (m, 3H), 7.50-7.68 (m, 12H), 7.22 (m, 3H), 7.01 (t, J=9 Hz, 2H), 4.56 (m, 1H), 3.81 (dd, J=11 Hz, J=39 Hz, 2H), 2.77 (s, 2H), 1.70-1.95 (m, 7H), 1.61 (m, 1H), 1.38 (m, 4H), 0.92 (t, J=7 Hz, 3H). ES-LCMS m/z 635 (M+H).

Example 14c

Preparation of [1-(4-fluorobenzyl)cyclobutyl]methyl (1S)-1-[oxo(1H-pyrazol-5-ylamino)acetyl]pentylcarbamate

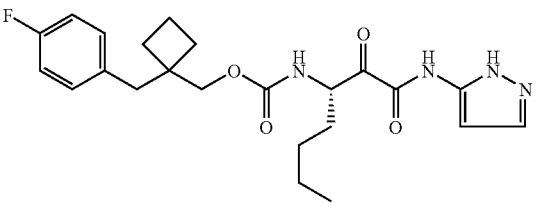

A –78° C. solution of 200 mg (0.32 mmol) of [1-(4-fluorobenzyl)cyclobutyl]methyl(1S)-1-[cyano(triphenylphosphoranylidene)acetyl]pentylcarbamate in 10 mL of dichloromethane was treated with a stream of ozone for 15 min before being purged with a stream of nitrogen for 5 min. To the reaction was added a solution of 26 mg (0.32 mmol) of 3-aminopyrazole in 1 mL of dichloromethane. The reaction was stirred for 30 min and concentrated under reduced pressure. The residue was dissolved in 5 mL of a 1M solution of silver nitrate in 4:1 tetrahydrofuran:water. The reacton was stirred at room temperature for 18 h and diluted with water. The mixture was extracted with dichloromethane, dried over magnesium sulfate, and concentrated. The residue was purified by silica gel chromatography eluting with 3.5:6.5 acetone:hexanes to afford 30 mg (21%) of [1-(4-fluorobenzyl)cyclobutyl]methyl(1S)-1-[oxo(1H-pyrazol-5-ylamino)acetyl]pentylcarbamate. $^1$H NMR (300 MHz, 80° C., DMSO-d$_6$) δ 7.65 (s, 1H), 7.42 (s, 1H), 7.22 (t, J=6 Hz, 2H), 7.08 (t, J=9 Hz, 2H), 6.54 (s, 1H), 4.93 (m, 1H), 3.82 (s, 2H), 2.78 (s, 2H), 1.70-1.95 (m, 2H), 1.61 (m, 2H), 1.38 (m, 4H), 0.91 (t, J=7 Hz, 3H). ES-LCMS m/z 467 (M+Na). HRMS C$_{23}$H$_{29}$N$_4$O$_4$F$_1$ m/z 467.2071 (M+Na)$_{Cal}$; 467.2073 (M+Na)$_{Obs}$.

Example 15

[1-(4-fluorobenzyl)cyclobutyl]methyl(1S)-1-[[(6-chloro-1H-indazol-3-yl)amino](oxo)acetyl]pentylcarbamate

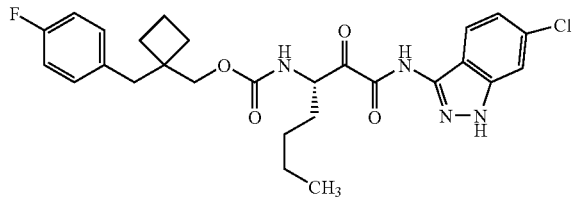

Example 15a

Preparation of [1-(4-fluorobenzyl)cyclobutyl]methyl (1S)-1-[[(6-chloro-1H-indazol-3-yl)amino](oxo) acetyl]pentylcarbamate

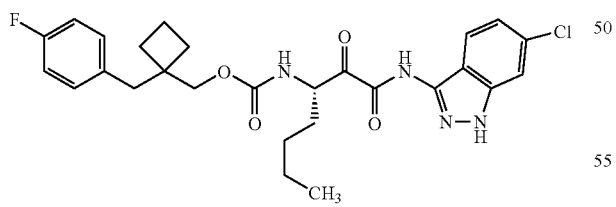

[1-(4-Fluorobenzyl)cyclobutyl]methyl(1S)-1-[[(6-chloro-1H-indazol-3-yl)amino](oxo)acetyl]pentylcarbamate was prepared as in example 14c except that 3-amino-6-chloroindazole was substituted for 3-aminopyrazole. $^1$H NMR (300 MHz, DMSO-d$_6$) δ 13.07 (s, 1H), 11.17 (s, 1H), 7.80 (m, 2H), 7.61 (s, 1H), 7.02-7.28 (m, 4H), 6.55 (m, 1H), 4.90 (m, 1H), 3.80 (s, 2H), 2.79 (s, 2H), 1.57-1.98 (m, 8H), 1.40 (m, 4H), 0.91 (t, J=7 Hz, 3H). ES-LCMS m/z 529 (M+Na).

Example 16

[1-(4-Fluorobenzyl)cyclobutyl]methyl(1S)-5-{[(dimethylamino)sulfonyl]amino}-1-{oxo[(3-pyridinylmethyl)amino] acetyl}pentylcarbamate

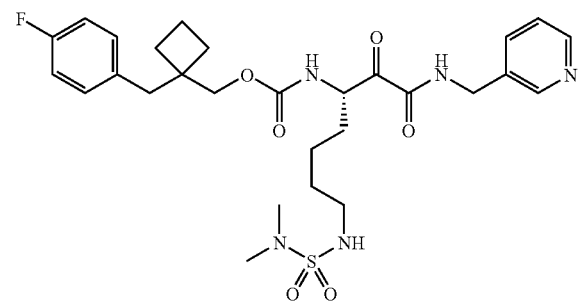

Example 16a

Preparation of 3-pyridinylmethyl isocyanide

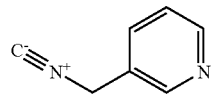

To a solution of 25 g (230 mmol) of 2-(aminomethyl) pyridine, 0.85 g of benzyltriethylammonium chloride, and 18.34 mL (230 mmol) of chloroform in 85 mL dichloromethane was added 85 mL 50% sodium hydroxide, dropwise. The mixture was stirred a total of 3 h and was diluted with water. The precipitate was filtered off and the filtrate extracted with dichloromethane. To the solution was added decolorizing carbon and magnesium sulfate. The mixture was filtered through celite and then through a silica plug, eluting with dichloromethane. The initial filtrate was discarded and the silica plug washed with ethyl acetate. The ethyl acetate wash was concentrated under reduced pressure to leave 3.8 g (14%) of 3-pyridinylmethyl isocyanide. $^1$H NMR (300 MHz, DMSO-d$_6$) δ 8.62 (m, 2H), 7.85 (d, J=8 Hz, 1H), 7.49 (dd, J=5 Hz, J=8 Hz, 1H), 4.96 (s, 2H).

Example 16b

Preparation of benzyl (5S)-5-[(tert-butoxycarbonyl) amino]-6,7-dioxo-7-[(3-pyridinylmethyl)amino]heptyl carbamate

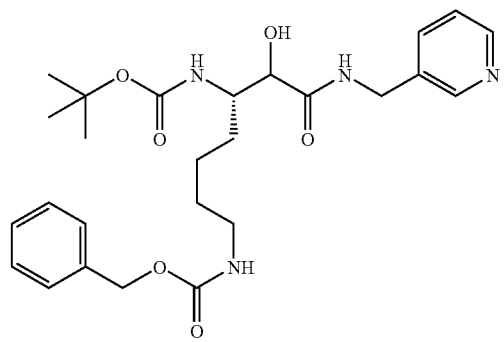

To a solution of 10.8 g (29.8 mmol) of benzyl (5S)-5-[(tert-butoxycarbonyl)amino]-6-oxohexyl carbamate in 300 mL of dichloromethane was added 3.52 g (29.8 mmol) of 3-pyridinylmethyl isocyanide followed by 7.3 g (59.7 mmol) of benzoic acid. The reaction was stirred at room temperature for 18 h and concentrated to 100 mL. The solution was added to a silica gel column and eluted with 2:8 acetone:dichloromethane to afford 11.64 g of a white solid. The solid was dissolved in 100 mL of dioxane before 100 mL of water was added followed by 1.05 g (25 mmol) of lithium hydroxide monohydrate. The mixture was heated briefly to promote homogeneity and then stirred at room temperature for 18 h. The mixture was extracted with ethyl acetate and dried over magnesium sulfate before being concentrated under reduced pressure. The residue was purified by silica gel chromatography eluting with 1:9 ethanol:ethyl acetate to afford 8.32 g (56%) of benzyl (5S)-5-[(tert-butoxycarbonyl)amino]-6,7-dioxo-7-[(3-pyridinylmethyl)amino]heptyl carbamate. $^1$H NMR (300 MHz, DMSO-$d_6$) δ 8.46 (m, 3H), 7.65 (d, J=7 Hz, 1H), 7.20-7.42 (m, 7H), (6.45 (d, J=9 Hz) and 6.05 (d, J=9 Hz), 1H), (5.72 (d, J=6 Hz) and 5.67 (d, J=6 Hz), 1H), 5.02 (s, 2H), 4.30 (m, 2H), 3.91-4.00 (m, 1H), 3.75 (m, 2H), 1.05-1.55 (m, 15H).

Example 16c

Preparation of tert-butyl (1S)-5-{[(dimethylamino)sulfonyl]amino}-1-{1-hydroxy-2-oxo-2-[(3-pyridinylmethyl)amino]ethyl}pentylcarbamate

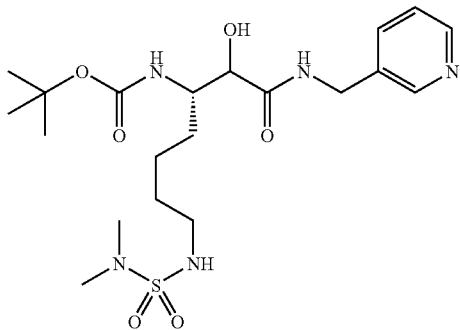

To a solution of 7.32 g (15 mmol) of benzyl (5S)-5-[(tert-butoxycarbonyl)amino]-6,7-dioxo-7-[(3-pyridinylmethyl)amino]heptyl carbamate in 200 mL of ethanol was added 500 mg of 10 wt % palladium on carbon and the mixture hydrogenated under 40 psi of hydrogen gas for 18 h. A precipitate was observed. To the reaction was added 500 mg of 10 wt % palladium on carbon and 100 mL of methanol to dissolve the precipitate. The mixture was hydrogenated under 40 psi hydrogen gas for 18 h before the catalyst was filtered off over celite. The wash was concentrated under reduced pressure to leave 5.6 g of an oil. The material was split and 1.81 g (4.9 mmol) of the oil was dissolved in 20 mL of tetrahydrofuran. To the solution was added 0.75 mL (5.4 mmol) of triethylamine and 0.56 mL (5.2 mmol) of dimethylsulfamoyl chloride. The reaction was stirred at room temperature for 18 h, heated to reflux for 5 h, and stirred at room temperature for 72 h. The mixture was concentrated under reduced pressure and the residue was purified by silica gel chromatography eluting with 7.5:2.5 acetone:hexanes to afford 1.13 g (48%) of tert-butyl (1S)-5-{[(dimethylamino)sulfonyl]amino}-1-{1-hydroxy-2-oxo-2-[(3-pyridinylm-ethyl)amino]ethyl}pentylcarbamate. $^1$H NMR (300 MHz, DMSO-$d_6$) δ 8.46 (m, 3H), 7.66 (m, 1H), 7.34 (m, 1H), 7.12 (m, 1H), (6.46 (d, J=9 Hz) and 6.06 (d, J=9 Hz), 1H), (5.73 (d, J=6 Hz) and 5.68 (d, J=6 Hz), 1H), 4.32 (m, 2H), 3.91-4.01 (m, 1H), 3.70-3.85 (m, 1H), 2.84 (m, 2H), 2.66 (s, 6H), 1.05-1.55 (m, 15H).

Example 16d

Preparation of (3S)-3-amino-7-{[(dimethylamino)sulfonyl]amino}-2-hydroxy-N-(3-pyridinylmethyl)heptanamide dihydrochloride

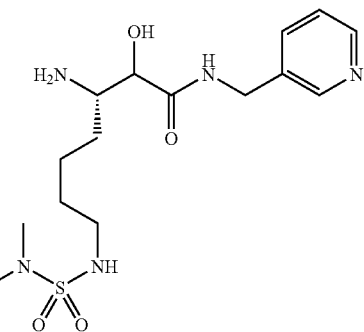

A 0° C. solution of 1.13 g (2.4 mmol) of tert-butyl (1S)-5-{[(dimethylamino)sulfonyl]amino}-1-{1-hydroxy-2-oxo-2-[(3-pyridinylmethyl)amino]ethyl}pentylcarbamate in 100 mL of ethyl acetate was bubbled with hydrogen chloride gas for 5 min and stirred at room temperature for 30 min before being concentrated under reduced pressure to afford 1.06 g (>99%) of (3S)-3-amino-7-{[(dimethylamino)sulfonyl]amino}-2-hydroxy-N-(3-pyridinylmethyl)heptanamide dihydrochloride. $^1$H NMR (300 MHz, DMSO-$d_6$) δ 8.92 (t, J=6 Hz, 1H), 8.76 (m, 2H), 8.09 (bs, 1H), 7.87 (m, 2H), 7.17 (m, 1H), 6.68 (m, 1H), 4.46 (m, 2H), (4.32 (d, J=3 Hz) and 4.18 (d, J=3 Hz), 1H), 3.37 (m, 1H), 2.83 (m, 2H), 2.67 (s, 6H), 1.25-1.60 (m, 6H). ES-LCMS m/z 374 (M+H).

Example 16e

Preparation of [1-(4-fluorobenzyl)cyclobutyl]methyl (1S)-5-{[(dimethylamino)sulfonyl]amino}-1-{1-hydroxy-2-oxo-2-[(3-pyridinylmethyl)amino]ethyl}pentylcarbamate

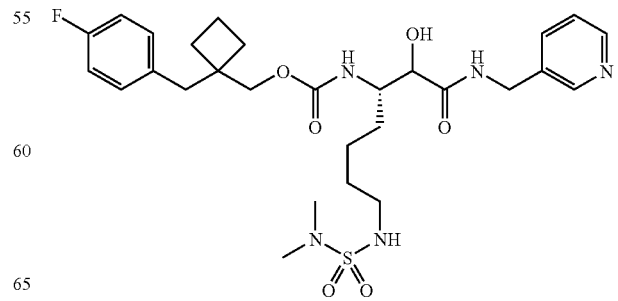

To 110 mg (0.57 mmol) of [1-(4-fluorobenzyl)cyclobutyl]methanol in 2 mL of tetrahydrofuran was added 0.59 mL (1.1 mmol) of 1.93 M phosgene in toluene and the reaction stirred at room temperature overnight. The mixture was concentrated under reduced pressure and added to a solution of 250 mg (0.57 mmol) of (3S)-3-amino-7-{[(dimethylamino)sulfonyl]amino}-2-hydroxy-N-(3-pyridinylmethyl)heptanamide dihydrochloride and 0.28 mL of triethylamine in 4 mL of tetrahydrofuran. The mixture was filtered through a frit and the wash concentrated under reduced pressure. The residue was purified by silica gel chromatography eluting with 7:3 acetone:hexanes to leave 200 mg (59%) of [1-(4-fluorobenzyl)cyclobutyl]methyl(1S)-5-{[(dimethylamino)sulfonyl]amino}-1-{1-hydroxy-2-oxo-2-[(3-pyridinylmethyl)amino]ethyl}pentylcarbamate. $^1$H NMR (300 MHz, DMSO-d$_6$) δ 8.38-8.55 (m, 2H), 7.65 (m, 1H), 6.7.00-7.40 (m, 7H), 6.55 (d, J=9 Hz, 1H), (5.83 (d, J=6 Hz) and 5.72 (J=6 Hz), 1H), 4.31 (m, 2H), 4.00 (m, 1H), 3.71-3.88 (m, 2H), 3.42 under water peak (m, 2H), 2.74-2.90 (m, 3H), 2.66 (s, 6H), 1.70-1.95 (m, 6H), 1.25-1.59 (m, 6H). ES-LCMS m/z 594 (M+H).

Example 16f

Preparation of [1-(4-fluorobenzyl)cyclobutyl]methyl (1S)-5-{[(dimethylamino)sulfonyl]amino}-1-{oxo[(3-pyridinylmethyl)amino]acetyl}pentylcarbamate

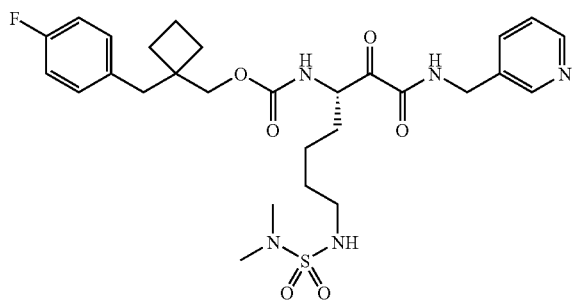

[1-(4-Fluorobenzyl)cyclobutyl]methyl(1S)-5-{[(dimethylamino)sulfonyl]amino}-1-{oxo[(3-pyridinylmethyl)amino]acetyl}pentylcarbamate was prepared as in example 9j except that [1-(4-fluorobenzyl)cyclobutyl]methyl(1S)-5-{[(dimethylamino)sulfonyl]amino}-1-{1-hydroxy-2-oxo-2-[(3-pyridinylmethyl)amino]ethyl}pentylcarbamate was substituted for (1-benzylcyclohexyl)methyl(1S)-1-(1-hydroxy-2-oxo-2-{[(1R)-1-phenylethyl]amino}ethyl)-5-[(4-morpholinylcarbonyl)amino]pentylcarbamate. $^1$H NMR (300 MHz, 80° C., DMSO-d$_6$) δ 9.07 (m, 1H), 8.52 (s, 1H), 8.47 (d, J=5 Hz, 1H), 7.68 (d, J=8 Hz, 1H), 7.33 (m, 1H), 7.21 (m, 2H), 7.08 (t, J=9 Hz, 2H), 6.82 (m, 1H), 4.85 (m, 1H), 4.40 (d, J=6 Hz, 2H), 3.81 (s, 2H), 3.10 under water peak (m, 2H), 2.92 (m, 2H), 2.70 (s, 6H), 1.70-1.95 (m, 6H), 1.37-1.65 (m, 6H). ES-LCMS m/z 592 (M+H).

Example 17

1-(1,3-Benzothiazol-2-yl)cyclopentyl(1S)-1-[oxo(1H-pyrazol-3-ylamino)acetyl]pentylcarbamate

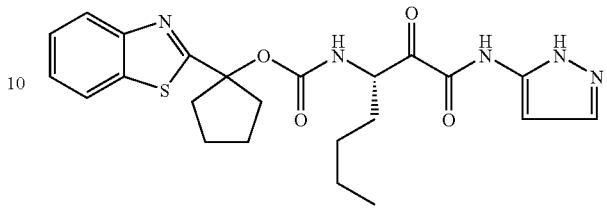

Example 17a

Preparation of 1-(1,3-benzothiazol-2-yl)cyclopentanol

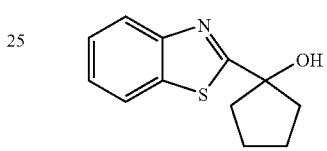

To a solution of 2 mL (18.3 mmol) of benzothiazole in 20 mL of tetrahydrofuran was added 11.4 mL (18.2 mmol) of 1.6 M n-BuLi at −78° C. After 45 min, 1.6 mL (18.1 mmol) of cyclopentanone was added at the same temperature. The reaction was let warm to room temperature over 1 h. Water was added to quench the reaction and the mixture was extracted with ether (3×). The ether layer was washed with brine (3×) and dried over magnesium sulfate. After removal of solvent, purification by silica gel column chromatography eluting with hexane:ethyl acetate (4:1) gave 2.8 g (71%) of 1-(1,3-benzothiazol-2-yl)cyclopentanol as a yellow solid. $^1$H NMR (300 MHz, CDCl$_3$) δ 8.02 (d, J=8 Hz, 1H), 7.92 (d, J=8 Hz, 1H), 7.51 (t, J=8 Hz, 1H), 7.41 (t, J=8 Hz, 1H), 2.25 (m, 4H), 2.00 (m, 4H).

Example 17b

Preparation of methyl(2S)-2-[({[1-(1,3-benzothiazol-2-yl)cyclopentyl]oxy}carbonyl)amino]hexanoate

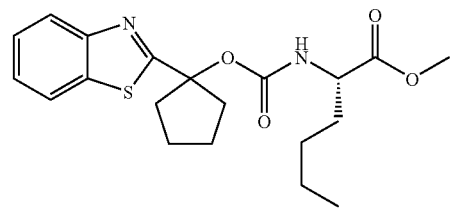

1.7 g (9.9 mmol) of (2S)-2-isocyanatohexanoate and 2.0 g (9.1 mmol) of 1-(1,3-benzothiazol-2-yl)cyclopentanol were dissolved in 5 mL of dry toluene and heated at 80° C. for 4 d. After removal of solvent, purification by silica gel column chromatography eluting with hexane:ethyl acetate (2:1) gave 3.5 g of methyl(2S)-2-[({[1-(1,3-benzothiazol-2- yl)cyclopentyl]oxy}carbonyl)amino]hexanoate as a yellow liquid, quantitatively. $^1$H NMR (300 MHz, CDCl$_3$) δ 8.02 (d, J=8 Hz, 1H), 7.86 (d, J=8 Hz, 1H), 7.47 (t, J=8 Hz, 1H), 7.37 (t, J=8 Hz, 1H), 5.42 (d J=8 Hz, 1H), 4.30 (m, 1H), 3.76 (s, 3H), 2.50 (m, 2H), 1.67-2.08 (m, 6H), 1.30 (m, 6H), 0.92 (t, J=8 Hz, 3H).

Example 17c

Preparation of 1-(1,3-benzothiazol-2-yl)cyclopentyl (1S)-1-[cyano(triphenylphosphoranylidene)acetyl] pentylcarbamate

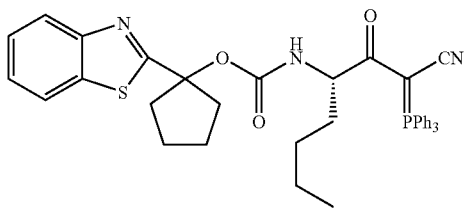

3.5 g (9 mmol) of methyl(2S)-2-[({[1-(1,3-benzothiazol-2-yl)cyclopentyl]oxy}carbonyl)amino] hexanoate was dissolved in 12 mL of tetrahydrofuran and 12 mL (12 mmol) of 1 M lithium hydroxide was added. The reaction was stirred at room temperature overnight. Water was added and the solution was acidified with 1 N hydrochloric acid to pH=3. The solution was extracted with ether (3×). The ether layer was washed with brine and dried over magnesium sulfate. After removal of solvent, the residue was dissolved in 20 mL of dichloromethane, and 2.23 g (11.6 mmol) of 1-(3-dimethylaminopropyl)-3-ethylcarbodiimide, 110 mg (0.9 mmol) of 4-dimethylaminopyridine and 2.8 g (9.3 mmol) of triphenylphosphenarylidene-acetonitrile were added. The reaction was stirred at room temperature overnight. More dichloromethane was added and the organic layer was washed with brine (3×) and dried over magnesium sulfate. After removal of solvent, purification by silica gel column chromatography eluting with hexane:ethyl acetate (1:1) gave 2.6 g (44%) of 1-(1,3-benzothiazol-2-yl)cyclopentyl(1S)-1-[cyano(triphenylphosphoranylidene)acetyl]pentylcarbamate as a solid. $^1$H NMR (300 Hz CDCl$_3$) δ 8.03 (d, J=8 Hz, 1H), 7.8 (d, J=8 Hz, 1H), 7.38-7.7 (m, 16H), 7.36 (t, J=8 Hz, 1H). 5.62 (d, J=8 Hz, 1H), 4.83 (m, 1H), 2.46-2.60 (m, 4H), 1.90-2.09 (m, 4H), 1.73 (m, 2H), 1.28-1.43 (m, 4H), 0.91 (t, J=7 Hz, 3H).

Example 17d

Preparation of 1-(1,3-benzothiazol-2-yl)cyclopentyl (1S)-1-[oxo(1H-pyrazol-3-ylamino)acetyl]pentylcarbamate

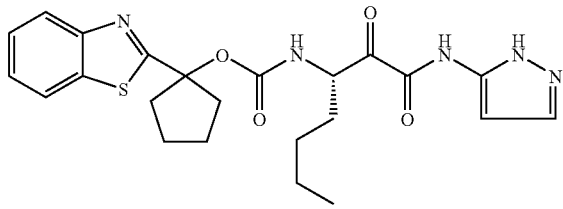

660 mg (1 mmol) of 1-(1,3-benzothiazol-2-yl)cyclopentyl (1S)-1-[cyano(triphenylphosphoranylidene)acetyl]pentylcarbamate was dissolved in 25 mL of dichloromethane and ozone was passed through the solution at −78° C. for 15 min. The reaction was quenched with N$_2$ for 5 min before 79 mg (0.95 mmol) of 3-aminopyrazole in 4 mL of tetrahydrofuran was added. The reaction was allowed to warm to room temperature over 1 h. Solvent was removed and the residue was redissolved in 5 mL of tetrahydrofuran. 1 mL of 1 M silver nitrate in water was added and the reaction was stirred at room temperature overnight. Water was added and the mixture was extracted with ether (4×). The ether layer was washed with brine (3×) and dried over magnesium sulfate. After removal of solvent, purification by silica gel column chromatography eluting with hexane:ethyl acetate (1:2) gave 150 mg (32%) of 1-(1,3-benzothiazol-2-yl)cyclopentyl (1S)-1-[oxo(1H-pyrazol-3-ylamino)acetyl]pentylcarbamate as a solid. $^1$H-NMR (400 MHz CDCl$_3$) δ 7.87 (d, J=8 Hz, 1H), 7.66 (d, J=8 Hz, 1H), 7.42 (s, 1H), 7.36 (t, J=8 Hz, 1H), 7.22 (m, 2H), 6.78 (s, 1H), 4.96 (br, 1H), 2.45 (m, 4H), 1.86 (m, 4H), 1.30 (m, 6H), 0.88 (t, J=8 Hz, 3H). ES-LCMS m/z 469 (M+H). C$_{23}$H$_{27}$N$_3$O$_4$S: 0.34 EtOAc: 0.13 H$_2$O: Anal C 58.3%, H 5.93%, N 13.95%; Calcd C, 58.3%, H, 6.02%, N, 13.95%.

Example 18

{1-[(4-phenyl-1,3-thiazol-2-yl)methyl]cyclobutyl}methyl (1S)-1-(oxo{[(1R)-1-phenylethyl]amino}acetyl)pentylcarbamate

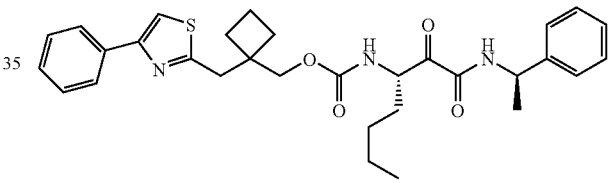

Example 18a

Preparation of [1-(hydroxymethyl)cyclobutyl]methanol

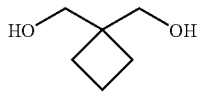

To a solution of 10.0 g (50.0 mmol) of diethyl 1,1-cyclobutane dicarboxylate in 200 ml of diethyl ether cooled to 0° C. was added a 1.0 M solution of lithium aluminum hydride in 200 mL of tetrahydrofuran over 15 min. The reaction was then warmed to room temperature and left to stir for 3 h. 200 mL of a 20% sodium hydroxide solution was then added, followed by addition of diethyl ether. The organic layer was isolated, dried with magnesium sulfate, and concentrated under vacuum to give a yellow oil, which was purified by silica gel chromatography using ethyl acetate as the eluent to afford 5.5 g (95%) of [1-(hydroxymethyl)cyclobutyl]methanol as a colorless oil. $^1$H NMR (300 MHz, CDCl$_3$) δ 3.73 (s, 4H), 2.81 (br s, 2H), 2.02-1.89 (m, 4H), 1.78 (t, J=8 Hz, 2H).

Example 18b

Preparation of {1-[(benzyloxy)methyl]cyclobutyl}methanol

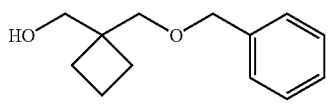

To a solution of 8.0 g (69 mmol) of [1-(hydroxymethyl)cyclobutyl]methanol in 120 ml of a 1:1 mixture of tetrahydrofuran:N,N-dimethylformamide was added 3.30 g (69 mmol) of a 60% dispersion of sodium hydride in oil and the contents stirred for 30 min. 8.6 mL (72.4 mmol) of benzyl bromide was then added and the contents stirred for 2 h. The reaction was quenched with aqueous ammonium chloride followed by the addition of diethyl ether. The organic phase was isolated, dried using magnesium sulfate, and concentrated under vacuum to afford the crude product which was purified by silica gel chromatography using ethyl acetate:hexane (3:7) as the eluent to afford 12.0 g (86%) of {1-[(benzyloxy)methyl]cyclobutyl}methanol as a colorless oil. $^1$H NMR (300 MHz, CDCl$_3$) δ 7.33-7.25 (m, 5H), 4.49 (s, 2H), 3.66 (d, J=6 Hz, 2H), 3.52 (s, 2H), 2.53 (t, J=6 Hz, 1H), 1.91-1.73 (m, 6H). GC-MS m/z 207 (M+H).

Example 18c

Preparation of {1-[(benzyloxy)methyl]cyclobutyl}methyl methanesulfonate

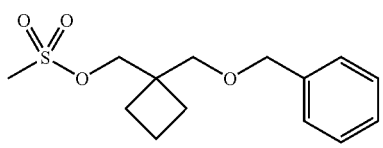

To a solution of 12.0 g (59.0 mmol) of {1-[(benzyloxy)methyl]cyclobutyl}methanol in 180 mL of dichloromethane was added 9.93 ml (70.8 mmol) of triethylamine at 0° C. followed by the addition of 5.02 mL (64.9 mmol) of methanesulfonyl chloride. After stirring for 2 h, saturated sodium chloride solution was added. The organic phase was isolated, dried using magnesium sulfate, and concentrated under vacuum to afford the crude product, which was used directly in the next step. $^1$H NMR (300 MHz, CDCl$_3$) δ 7.39-7.32 (m, 5H), 4.57 (s, 2H), 4.30 (s, 2H), 3.52 (s, 2H), 2.98 (s, 3H), 1.95 (m, 6H).

Example 18d

Preparation of {1-[(benzyloxy)methyl]cyclobutyl}acetonitrile

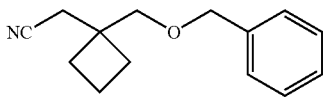

To a solution of 16.75 g (59.0 mmol) of {1-[(benzyloxy)methyl]cyclobutyl}methyl methanesulfonate in 150 mL of N,N-dimethylformamide and 15 mL of water was added 4.97 g (88.5 mmol) of potassium cyanide and the contents heated at 130° C. for 5 h. The reaction mixture was cooled, diluted with ether and water, and the layers separated. The organic phase was dried using magnesium sulfate and concentrated under vacuum to afford the crude product, which was purified by silica gel chromatography using ethyl acetate/hexane (1:3) as the eluent to afford 8.0 g (88%) of {1-[(benzyloxy)methyl]cyclobutyl}acetonitrile as a colorless oil. $^1$H NMR (300 MHz, CDCl$_3$). $^1$H NMR (300 MHz, CDCl$_3$) δ 7.43-7.29 (m, 5H), 4.59 (s, 2H), 3.5 (s, 2H), 2.6 (s, 2H), 2.08-1.92 (m, 6H).

Example 18e

Preparation of 2-{1-[(benzyloxy)methyl]cyclobutyl}ethanethioamide

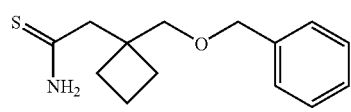

To a solution of 9.7 g (45 mmol) of {1-[(benzyloxy)methyl]cyclobutyl}acetonitrile in 100 mL of tetrahydrofuran and 10 mL of water was added 15.13 mL (90.2 mmol) of diethyldithiophosphate and the contents heated at reflux for 16 h. Ethyl acetate and water were added, and the layers separated. The organic phase was dried using magnesium sulfate and concentrated under vacuum to afford the crude product, which was purified by silica gel chromatography using ethyl acetate:hexane (2:8) as the eluent to afford 8.0 g (71%) of 2-{1-[(benzyloxy)methyl]cyclobutyl}ethanethioamide as a colorless oil. $^1$H NMR (300 MHz, CDCl$_3$) δ 8.00 (br s, 2H), 7.39-7.30 (m, 5H), 4.59 (s, 2H), 3.58 (s, 2H), 3.09 (s, 2H), 2.14-1.87 (m, 6H).

Example 18f

Preparation of 2-({1-[(benzyloxy)methyl]cyclobutyl}methyl)-4-phenyl-1,3-thiazole

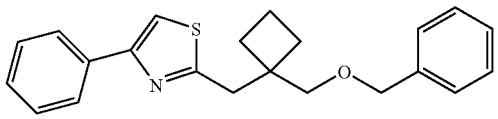

To a solution of 0.5 g (2.01 mmol) of 2-{1-[(benzyloxy)methyl]cyclobutyl}ethanethioamide in 10 mL of acetonitrile was added 0.39 g (2.01 mmol) of phenacyl bromide and the contents stirred at room temperature for 3 h. The mixture was concentrated under vacuum and the residue was purified by silica gel chromatography using ethyl acetate:hexane (2:8) as the eluent to afford 0.68 g (97%) of 2-({1-[(benzyloxy)methyl]cyclobutyl}methyl)-4-phenyl-1,3-thiazole as a colorless oil. $^1$H NMR (300 MHz, CDCl$_3$) δ 8.02 (s, 1H), 7.96-7.30 (m, 5H), 4.60 (s, 2H), 3.50 (s, 2H), 3.35 (s, 2H), 2.13-1.95 (m, 6H).

Example 18g

Preparation of {1-[(4-phenyl-1,3-thiazol-2-yl)methyl]cyclobutyl}methanol

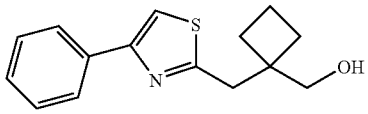

To a solution of 0.7 g (2.0 mmol) of 2-({1-[(benzyloxy)methyl]cyclobutyl}methyl)-4-phenyl-1,3-thiazole in 15 mL of dichloromethane was added a 1.0 M solution of 2.2 mL (2.2 mmol) of boron tribromide and the contents stirred at room temperature for 16 h. After quenching with 10 mL of methanol, the contents were concentrated under vacuum and the residue was purified by silica gel chromatography using ethyl acetate:hexane (1:9) as the eluent to afford 0.16 g (31%) of {1-[(4-phenyl-1,3-thiazol-2-yl)methyl]cyclobutyl}methanol as a colorless oil. $^1$H NMR (300 MHz, CDCl$_3$) δ 4.13 (t, J=7 Hz, 1H), 3.66 (d, J=6 Hz, 2H), 3.3 (s, 2H), 2.08-1.94 (m, 6H). GC-MS m/z 260 (M+H).

Example 18h

Preparation of {1-[(4-phenyl-1,3-thiazol-2-yl)methyl]cyclobutyl}methyl(1S)-1-(1-hydroxy-2-oxo-2-{[(1R)-1-phenylethyl]amino}ethyl)pentylcarbamate

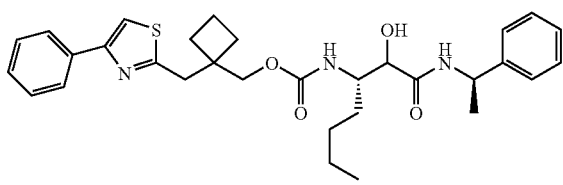

To a solution of 0.16 g (0.63 mmol) of {1-[(4-phenyl-1,3-thiazol-2-yl)methyl]cyclobutyl}methanol in 2 mL of dichloromethane (cooled to 0° C. was added a 1.0 M solution of 0.94 mL (1.41 mmol) of phosgene in toluene and the contents stirred for 16 h. The reaction mixture was concentrated and the residue was dissolved in 3 mL of tetrahydrofuran and added to a 0° C. solution of 0.165 g (0.63 mmol) of (3S)-3-amino-2-hydroxy-N-[(1R)-1-phenylethyl]heptanamide and 0.325 mL (1.89 mmol) of N,N-diisopropylethylamine in 2 mL of tetrahydrofuran. After stirring for 7 h, 30 mL of ethyl acetate and 20 mL of saturated sodium chloride were added. The organic phase was isolated, dried using magnesium sulfate, and concentrated under vacuum to afford the crude product, which was purified by silica gel chromatography using ethyl acetate:hexane (1:1) as the eluent to afford 0.34 g (98%) of {1-[(4-phenyl-1,3-thiazol-2-yl)methyl]cyclobutyl}methyl(1S)-1-(1-hydroxy-2-oxo-2-{[(1R)-1-phenylethyl]amino}ethyl)pentylcarbamate as a colorless oil. $^1$H NMR (300 MHz, CDCl$_3$) δ 7.90, 7.92 (2s, 1H), 7.46-7.18 (m, 10 H), 5.61 (d, J=9 Hz, 1H), 5.14-5.01 (m, 2H), 4.19-4.06 (m, 4H), 3.88 (m, 1H), 3.23 (s, 2H), 2.21-1.50 (m, 10 H), 1.46 (d, J=7 Hz, 3H), 1.37-1.27 (m, 2H), 0.94 (m, 3H). LC-MS m/z 550 (M+H).

Example 18i

Preparation of {1-[(4-phenyl-1,3-thiazol-2-yl)methyl]cyclobutyl}methyl (1S)-1-(oxo{[(1R)-1-phenylethyl]amino}acetyl)pentylcarbamate

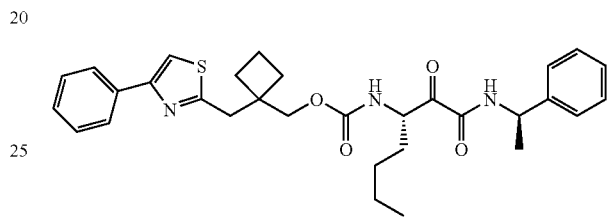

To a solution of 0.2 g (0.364 mmol) of {1-[(4-phenyl-1,3-thiazol-2-yl)methyl]cyclobutyl}methyl (1S)-1-(1-hydroxy-2-oxo-2-{[(1R)-1-phenylethyl]amino}ethyl)pentylcarbamate in 3 mL of dichloromethane cooled to −60° C. was added 0.079 mL (0.91 mmol) of oxalyl chloride and— 0.129 mL (1.82 mmol) od dimethylsulfoxide, followed by the addition of 0.204 mL (1.45 mmol) of triethylamine. After stirring for 15 min, the reaction was warmed to room temperature and applied directly to a silica gel column using ethyl acetate:hexane (3:7) as the eluent to afford 0.19 g (96%) of {1-[(4-phenyl-1,3-thiazol-2-yl)methyl]cyclobutyl}methyl (1S)-1-(oxo{[(1R)-1-phenylethyl]amino}acetyl)pentylcarbamate as a colorless oil. $^1$H NMR (300 MHz, DMSO-d$_6$) δ 9.21 (d, J=8 Hz, 1H), 7.98 (m, 3H), 7.64 (d, J=8 Hz, 1H), 7.25-7.23 (m, 8 H), 4.96-5.01 (m, 1H), 4.80 (m, 1H), 4.01 (s, 2H), 3.30 (s, 2H), 2.12-1.64 (m, 10 H), 1.42 (d, J=7 Hz, 3H), 1.29-1.21 (m, 2H), 0.82 (t, J=7 Hz, 3H). LC-MS m/z 548 (M+H).

Example 19

(1-{[(1-methyl-1H-imidazol-2-yl)sulfanyl]methyl}cyclobutyl)methyl (1S)-1-(oxo{[(1R)-1-phenylethyl]amino}acetyl)pentylcarbamate

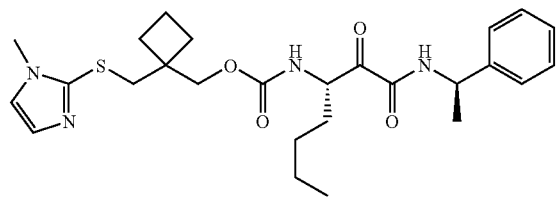

Example 19a

Preparation of (1-{[(1-methyl-1H-imidazol-2-yl)sulfanyl]methyl}cyclobutyl)methanol

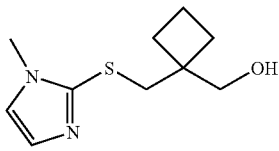

To a solution of 1.0 g (8.6 mmol) of [1-(hydroxymethyl)cyclobutyl]methanol in 20 mL of dichloromethane was added 2.48 g (9.48 mmol) of triphenylphosphine and 2.18 g (9.48 mmol) of di-tertbutylazodicarboxylate. After 5 min of stirring, 1.03 g (9.05 mmol) of 1-methyl-2-mercaptoimidazole was added as a solid. After stirring for 2 h, the reaction was concentrated under vacuum and the residue was purified using silica gel chromatography eluting with ethyl acetate:hexane (3:7) to afford 1.3 g (71%) of (1-{[(1-methyl-1H-imidazol-2-yl)sulfanyl]methyl}cyclobutyl)methanol as a yellow oil. $^1$H NMR (300 MHz, CDCl$_3$) δ 6.95 (s, 1H), 6.87 (s, 1H), 6.54 (br s, 1H), 3.62 (s, 2H), 3.56 (s, 3H), 3.43 (s, 2H), 1.98-1.75 (m, 6H).

Example 19b

Preparation of (1-{[(1-methyl-1H-imidazol-2-yl)sulfanyl]methyl}cyclobutyl)methyl (1S)-1-(1-hydroxy-2-oxo-2-{[(1R)-1-phenylethyl]amino}ethyl)pentylcarbamate

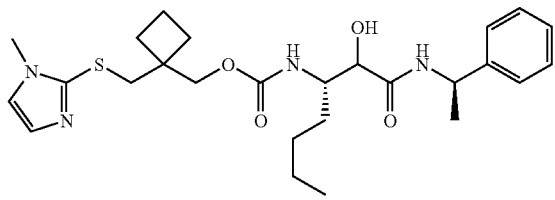

To a solution of 0.132 g (0.625 mmol) of (1-{[(1-methyl-1H-imidazol-2-yl)sulfanyl]methyl}cyclobutyl) methanol in 2 mL of dichloromethane cooled to 0° C. was added a 1.0 M solution of 0.94 mL (1.41 mmol) of phosgene in toluene and the contents were stirred for 16 h. The reaction mixture was concentrated and the residue was dissolved in 3 mL of tetrahydrofuran, and added to a 0° C. solution of 0.165 g (0.63 mmol) of (3S)-3-amino-2-hydroxy-N-[(1R)-1-phenylethyl]heptanamide and 0.325 mL (1.89 mmol) of N,N-diisopropylethylamine in 2 mL of tetrahydrofuran. After stirring for 6 h, 30 mL of ethyl acetate and 20 mL of saturated sodium chloride was added. The organic phase was isolated, dried using magnesium sulfate, and concentrated under vacuum to afford the crude product which was purified by silica gel chromatography eluting with ethyl acetate to afford 0.220 g (70%) of (1-{[(1-methyl-1H-imidazol-2-yl)sulfanyl]methyl}cyclobutyl)methyl (1S)-1-(1-hydroxy-2-oxo-2-{[(1R)-1-phenylethyl]amino}ethyl)pentylcarbamate as a colorless oil. $^1$H NMR (300 MHz, CDCl$_3$)) δ 7.63-7.52 (m, 1H), 7.41 (m, 1H), 7.39-7.15 (m, 5H), 6.91, 6.98 (2s, 1H), 6.03 (br s, 1H), 5.69 (m, 1H), 5.19-5.11 (m, 1H), 4.18-3.95 (m, 4H), 3.61, 3.63 (2s, 2H), 3.28 (m, 2H), 2.21-1.61 (m, 10H), 1.60-1.16 (m, 5H), 0.90 (m, 3H). LC-MS m/z 503 (M+H).

Example 19c

Preparation of (1-{[(1-methyl-1H-imidazol-2-yl)sulfanyl]methyl}cyclobutyl)methyl (1S)-1-(oxo{[(1R)-1-phenylethyl]amino}acetyl)pentylcarbamate

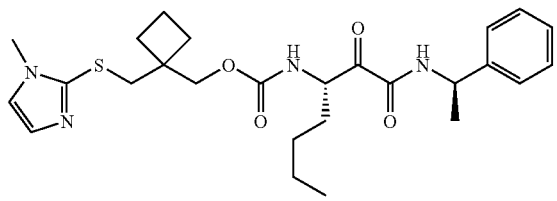

To a solution of 0.182 g (0.364 mmol) of (1-{[(1-methyl-1H-imidazol-2-yl)sulfanyl]methyl}cyclobutyl) methyl (1S)-1-(1-hydroxy-2-oxo-2-{[(1R)-1-phenylethyl]amino}ethyl)pentylcarbamate in 3 mL of dichloromethane cooled to −60° C. was added 0.079 mL (0.91 mmol) of oxalyl chloride and 0.129 ml (1.82 mmol) of dimethylsulfoxide, followed by 0.204 mL (1.45 mmol) of triethylamine. After stirring for 15 min, the reaction was warmed to room temperature and applied directly to a silica gel column eluting with ethyl acetate to afford 0.052 g (29%) of (1-{[(1-methyl-1H-imidazol-2-yl)sulfanyl]methyl}cyclobutyl)methyl (1S)-1-(oxo{[(1R)-1-phenylethyl]amino}acetyl)pentylcarbamate as a colorless oil. $^1$H NMR (300 MHz, CDCl$_3$) δ 7.41-7.30 (m, 6H), 7.17 (d, J=8 Hz, 1H), 6.98 (s, 1H), 5.41 (m, 1H), 5.23-5.11 (m, 2H), 4.16 (s, 2H), 3.58 (s, 3H), 3.36 (s, 2H), 2.07-1.89 (m, 6H), 1.48-1.16 (m, 6H), 1.56 (d, J=7 Hz, 3H), 0.89 (t, J=7 Hz, 3H). LC-MS m/z 501 (M+H).

Example 20

(1-{[(2-chloro-4-pyrimidinyl)oxy]methyl}cyclobutyl)methyl(1S)-1-(oxo{[(1R)-1-phenylethyl]amino}acetyl)pentylcarbamate

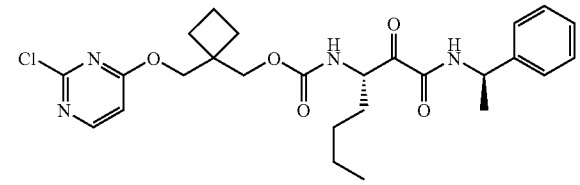

Example 20a

Preparation of (1-{[(2-chloro-4-pyrimidinyl)oxy]methyl}cyclobutyl)methanol

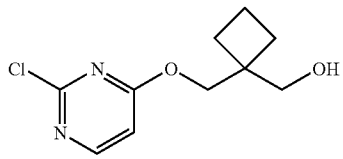

To a solution of 1.00 g (8.62 mmol) of [1-(hydroxymethyl)cyclobutyl]methanol in 20 ml of (1:1) tetrahydrofuran:dimethylforamide was added a 60% dispersion of 0.413 g (8.62 mmol) of sodium hydride in oil. The reaction was stirred for 15 min and 1.28 g (8.62 mmol) of 2,4-dichloropyrimidine was added. After stirring for 2 h, the reaction was concentrated under vacuum and the residue was purified using silica gel chromatography eluting with ethyl acetate:hexane (4:6) to afford 0.9 g (51%) of (1-{[(2-chloro-4-pyrimidinyl)oxy]methyl}cyclobutyl)methanol as a colorless oil. $^1$H NMR (300 MHz, CDCl$_3$) δ 8.32 (d, J=6 Hz, 1H), 6.69 (d, J=7 Hz, 1H), 4.51 (s, 2H), 3.67 (s, 2H), 2.35 (br s, 1H), 2.05-1.87 (m, 6H).

Example 20b

Preparation of (1-{[(2-chloro-4-pyrimidinyl)oxy]methyl}cyclobutyl)methyl (1S)-1-(1-hydroxy-2-oxo-2-{[(1R)-1-phenylethyl]amino}ethyl)pentylcarbamate

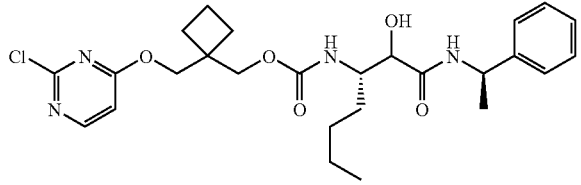

To a solution of 0.106 g (0.05 mmol) of (1-{[(2-chloro-4-pyrimidinyl)oxy]methyl}cyclobutyl)methanol in 2 mL of dichloromethane cooled to 0° C. was added a 1.0 M solution of 0.937 mL (0.75 mmol) of phosgene in toluene and the contents stirred for 16 h. The reaction mixture was concentrated and the residue was dissolved in 4 mL of tetrahydrofuran and added to a 0° C. solution of 0.132 g (0.50 mmol) of (3S)-3-amino-2-hydroxy-N-[(1R)-1-phenylethyl]heptanamide and 0.259 mL (1.5 mmol) of N,N-diisopropylethylamine in 2 mL of tetrahydrofuran. After stirring for 5 h, ethyl acetate and saturated sodium chloride were added. The organic phase was isolated, dried using magnesium sulfate, concentrated under vacuum, and the residue was purified by silica gel chromatography eluting with ethyl acetate:hexane (7:3) to afford 0.215 g (89%) of (1-{[(2-chloro-4-pyrimidinyl)oxy]methyl}cyclobutyl)methyl (1S)-1-(1-hydroxy-2-oxo-2-{[(1R)-1-phenylethyl]amino}ethyl)pentylcarbamate as a colorless oil. $^1$H NMR (300 MHz, CDCl$_3$) δ 8.29 (d, J=6 Hz, 1H), 7.32-7.10 (m, 6H), 6.67 (d, J=6 Hz, 1H), 5.61-5.53 (m, 1H), 5.13-5.08 (m, 1H), 4.79, 4.89 (2d, J=5, 6 Hz, 1H), 4.36, 4.39 (2s, 2H), 4.38-4.18 (m, 3H), 3.84 (m, 1H), 2.07-1.50 (m, 10 H), 1.47-1.26 (m, 5H), 0.88 (m, 3H). LC-MS m/z 519 (M+H).

Example 20c

Preparation of (1-{[(2-chloro-4-pyrimidinyl)oxy]methyl}cyclobutyl)methyl (1S)-1-(oxo{[(1R)-1-phenylethyl]amino}acetyl)pentylcarbamate

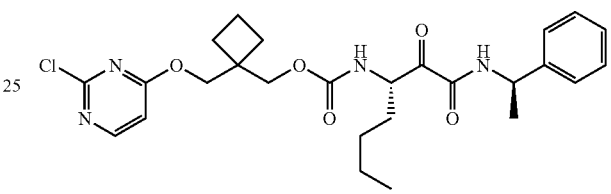

To a solution of 0.150 g (0.289 mmol) of (1-{[(2-chloro-4-pyrimidinyl)oxy]methyl}cyclobutyl)methyl (1S)-1-(1-hydroxy-2-oxo-2-{[(1R)-1-phenylethyl]amino}ethyl)pentylcarbamate in 2.0 mL of dichloromethane was added 0.031 g (0.375 mmol) of sodium bicarbonate followed by the addition of 0.159 g (0.375 mmol) of Dess-Martin periodinane. The reaction was stirred for 15 min and then poured directly onto a column of silica gel eluting with ethyl acetate:hexane (1:1) to afford 0.1 g (67%) of (1-{[(2-chloro-4-pyrimidinyl)oxy]methyl}cyclobutyl)methyl (1S)-1-(oxo{[(1R)-1-phenylethyl]amino}acetyl)pentylcarbamate as a colorless oil. $^1$H NMR (300 MHz, CDCl$_3$) δ 8.31 (m, 6 Hz, 1H), 7.41-7.29 (m, 5H), 7.13 (d, J=7 Hz, 1H), 6.69 (d, J=6 Hz, 1H), 5.29 (d, J=7 Hz, 1H), 5.18-5.08 (m, 2H), 4.41 (s, 2H), 4.20 (s, 2H), 2.07-1.71 (m, 7H), 1.56 (d, J=7 Hz, 3H), 1.26-1.32 (m, 5H), 0.88 (t, J=6 Hz, 3H). LC-MS m/z 517 (M+H).

Example 21

[1-({[2-(4-methyl-1-piperazinyl)-4-pyrimidinyl]oxy}methyl)cyclobutyl]methyl (1S)-1-(oxo{[(1R)-1-phenylethyl]amino}acetyl)pentylcarbamate

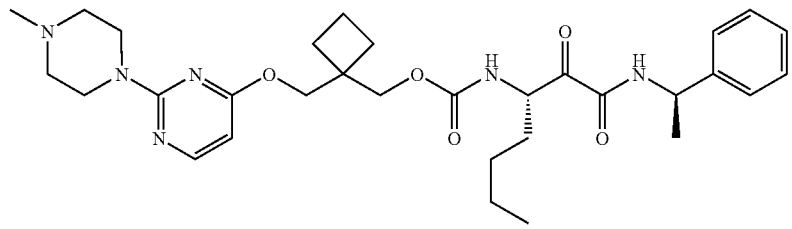

Example 21a

Preparation of [1-({[2-(4-methyl-1-piperazinyl)-4-pyrimidinyl]oxy}methyl)cyclobutyl]methanol

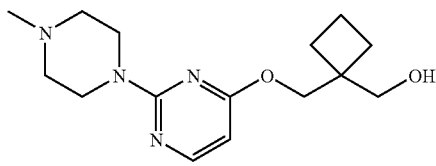

To a solution of 0.5 g (2.19 mmol) of (1-{[(2-chloro-4-pyrimidinyl)oxy]methyl}cyclobutyl)methyl (1S)-1-(oxo{[(1R)-1-phenylethyl]amino}acetyl)pentylcarbamate in 5.0 mL of N,N-dimethylformamide was added 0.36 mL (3.28 mmol) of N-methylpiperidine and the contents heated at 90° C. for 3 h. The reaction was concentrated under vacuum and taken directly to the next step. $^1$H NMR (300 MHz, CDCl$_3$) δ 8.05 (d, J=6 Hz, 1H), 5.97 (d, J=6 Hz, 1H), 4.41 (s, 2H), 3.81 (t, J=5 Hz, 4H), 3.63 (s, 2H), 2.45 (t, J=5 Hz, 4H), 2.35 (s, 3H), 1.97-1.91 (m, 6H).

Example 21b

Preparation of [1-({[2-(4-methyl-1-piperazinyl)-4-pyrimidinyl]oxy}methyl)cyclobutyl]methyl (1S)-1-(1-hydroxy-2-oxo-2-{[(1R)-1-phenylethyl]amino}ethyl)pentylcarbamate

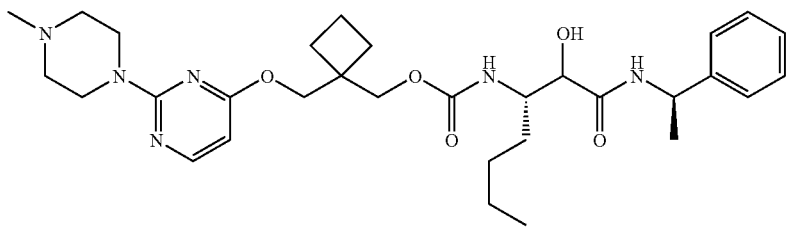

The title compound was prepared using the same experimental procedure as in example 20b starting with [1-({[2-(4-methyl-1-piperazinyl)-4-pyrimidinyl]oxy}methyl)cyclobutyl]methanol as the alcohol component and (3S)-3-amino-2-hydroxy-N-[(1R)-1-phenylethyl]heptanamide as the aminoalcohol component. $^1$H NMR (300 MHz, CDCl$_3$) δ 8.02 (d, J=6 Hz, 1H), 7.34-7.20 (m, 5H), 5.97 (d, J=6 Hz, 1H), 5.63 (d, J=8 Hz, 1H), 5.06 (m, 1H), 4.26 (s, 2H), 4.21-4.07 (m, 3H), 3.83 (m, 4H), 2.49 (m, 4H), 2.35 (s, 3H), 2.06-1.94 (m, 6H), 1.70-1.22 (m, 12 H), 0.89 (m, 3H). LC-MS m/z 583 (M+H).

Example 21c

Preparation of [1-({[2-(4-methyl-1-piperazinyl)-4-pyrimidinyl]oxy}methyl)cyclobutyl]methyl (1S)-1-(oxo{[(1R)-1-phenylethyl]amino}acetyl)pentylcarbamate

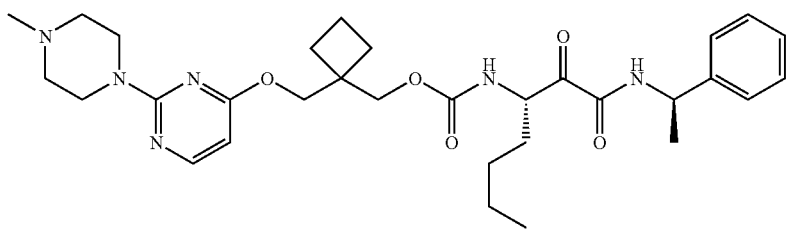

The title compound was prepared using the same experimental procedure as in example 20c using [1-({2-(4-methyl-1-piperazinyl)-4-pyrimidinyl]oxy}methyl)cyclobutyl]methyl(1S)-1-(1-hydroxy-2-oxo-2-{[(1R)-1-phenylethyl]amino}ethyl)pentylcarbamate as the starting material. $^1$H NMR (300 MHz, CDCl$_3$) δ 8.61 (m, 1H), 8.10 (m, 1H), 7.36-7.33 (m, 5H), 7.26 (d, J=7 Hz,1H), 6.07 (d, J=5 Hz, 1H), 5.01 (m, 1H), 4.20 (m, 1H), 4.07 (m, 1H), 3.76 (m, 4H), 2.43 (m, 4H), 2.28 (s, 3H), 2.15-1.90 (m, 6H), 1.49 (d, J=8 Hz, 3H), 1.38-1.11 (m, 9H), 0.84 (t, J=7 Hz, 3H). LC-MS m/z 581 (M+H).

Example 22

[1-({[2-(4-morpholinyl)-4-pyrimidinyl]oxy}methyl)cyclobutyl]methyl (1S)-1-(oxo{[(1R)-1-phenylethyl]amino}acetyl)pentylcarbamate

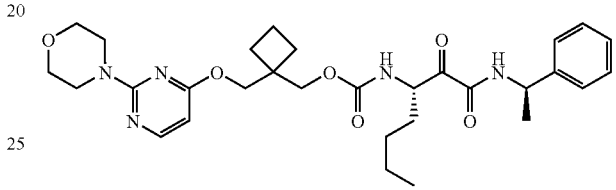

Example 22a

Preparation of [1-({[2-(4-morpholinyl)-4-pyrimidinyl]oxy}methyl)cyclobutyl]methanol

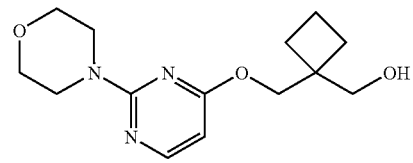

[1-({[2-(4-morpholinyl)-4-pyrimidinyl]oxy}methyl)cyclobutyl]methanol was prepared using the same experimental procedure as in example 21a using N-methylmorpholine instead of N-methylpiperidine. $^1$H NMR (300 MHz, CDCl$_3$) δ 8.04 (d, J=6 Hz, 1H), 5.99 (d, J=6 Hz, 1H), 4.38 (s, 2H), 3.75 (m, 4H), 3.62 (s, 2H), 2.15 (m, 4H), 1.95-1.89 (m, 6H).

Example 22b

Preparation of [1-({[2-(4-morpholinyl)-4-pyrimidinyl]oxy}methyl)cyclobutyl]methyl (1S)-1-(1-hydroxy-2-oxo-2-{[(1R)-1-phenylethyl]amino}ethyl)pentylcarbamate

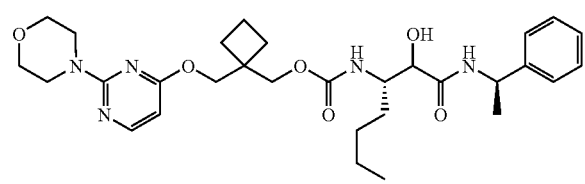

The title compound was prepared using the same experimental procedure as in example 20b using [1-({[2-(4-morpholinyl)-4-pyrimidinyl]oxy}methyl)cyclobutyl]methanol as the alcohol component and (3S)-3-amino-2-hydroxy-N-[(1R)-1-phenylethyl]heptanamide as the aminoalcohol component. $^1$H NMR (300 MHz, CDCl$_3$) δ 8.06 (d, J=6 Hz, 1H), 7.37-7.25 (m, 5H), 7.13 (d, J=8 Hz, 1H), 6.01 (d, J=6 Hz, 1H), 5.56 (d, J=9 Hz, 1H), 5.12-5.07 (m, 1H), 4.91 (d, J=4 Hz, 1H), 4.32-4.09 (m, 5H), 3.79 (m, 5H), 2.07-1.49 (m, 12H), 1.46 (d, J=7 Hz, 3H), 1.36-1.27 (m, 4H), 0.91 (m, 3H). LC-MS m/z 570 (M+H).

Example 22c

Preparation of [1-({[2-(4-morpholinyl)-4-pyrimidinyl]oxy}methyl)cyclobutyl]methyl (1S)-1-(oxo{[(1R)-1-phenylethyl]amino}acetyl)pentylcarbamate

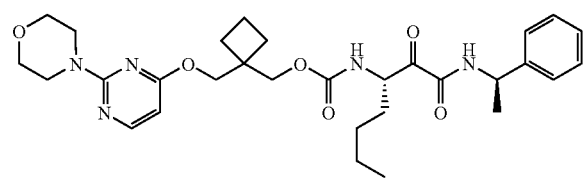

The title compound was prepared using the same experimental procedure as in example 20c using [1-({[2-(4-morpholinyl)-4-pyrimidinyl]oxy}methyl)cyclobutyl]methyl (1S)-1-(1-hydroxy-2-oxo-2-{[(1R)-1-phenylethyl]amino}ethyl)pentylcarbamate as the starting material. $^1$H NMR (300 MHz, CDCl$_3$) δ 8.07 (d, J=6 Hz, 1H), 7.38-7.29 (m, 5H), 7.12 (d, J=8 Hz, 1H), 6.03 (d, J=6 Hz, 1H), 5.08-5.33 (m, 3H), 4.29 (s, 2H), 4.20 (s, 2H), 3.81 (m, 8H), 2.11-1.96 (m, 8H), 1.56 (d, J=7 Hz, 3H), 1.31-1.26 (m, 4H), 0.88 (br s, 3H). LC-MS m/z 568 (M+H).

Example 23

{1-[(2-pyrimidinylsulfanyl)methyl]cyclobutyl}methyl (1S)-1-(oxo{[(1R)-1-phenylethyl]amino}acetyl)pentylcarbamate

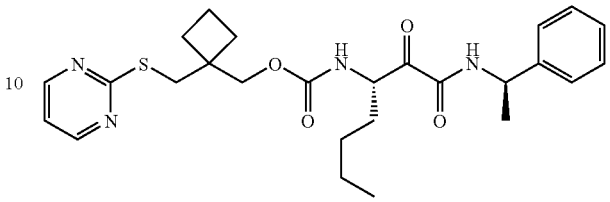

Example 23a

Preparation of {1-[(2-pyrimidinylsulfanyl)methyl]cyclobutyl}methanol

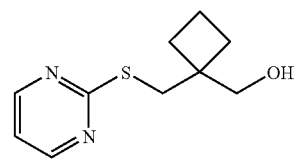

{1-[(2-Pyrimidinylsulfanyl)methyl]cyclobutyl}methanol was prepared using the same experimental procedure as in example 19a using 2-mercaptopyrimidine instead of 1-methyl-2-mercapto imidazole as the thiol component. $^1$H NMR (300 MHz, CDCl$_3$) δ 8.51 (d, J=5 Hz, 2H), 7.01 (t, J=5 Hz, 1H), 4.39 (t, J=7 Hz, 1H), 3.55 (d, J=7 Hz, 2H), 3.43 (s, 2H), 2.06-1.82 (m, 6H). GC-MS m/z 211 (M+H).

Example 23b

Preparation of {1-[(2-pyrimidinylsulfanyl)methyl]cyclobutyl}methyl (1S)-1-(1-hydroxy-2-oxo-2-{[(1R)-1-phenylethyl]amino}ethyl)pentylcarbamate

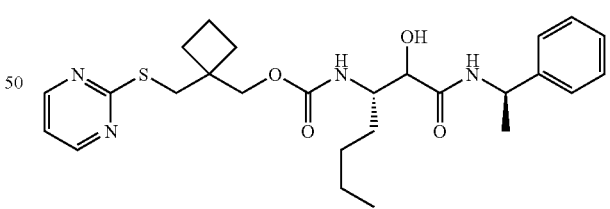

The title compound was prepared using the same experimental procedure as in example 20b with {1-[(2-pyrimidinylsulfanyl)methyl]cyclobutyl}methanol as the alcohol component and (3S)-3-amino-2-hydroxy-N-[(1R)-1-phenylethyl]heptanamide as the aminoalcohol component. $^1$H NMR (300 MHz, CDCl$_3$) δ 8.50 (d, J=5 Hz, 2H), 7.37-7.25 (m 5H), 7.15 (d, J=8 Hz, 1H), 6.95 (t, J=5 Hz, 1H), 5.56 (d, J=9 Hz, 1H), 5.09 (m, 1H), 4.96 (d, J=6 Hz, 1H), 4.20-4.06 (m, 3H), 3.86 (m, 1H), 3.49 (s, 2H), 2.07-1.73 (m, 6H), 1.83-1.61 (m, 2H), 1.48 (d, J=7 Hz, 3H), 1.37-1.26 (m, 4H), 0.92 (m, 3H). LC-MS m/z 501 (M+H).

Example 23c

Preparation of {1-[(2-pyrimidinylsulfanyl)methyl]cyclobutyl}methyl (1S)-1-(oxo{[(1R)-1-phenylethyl]amino}acetyl)pentylcarbamate

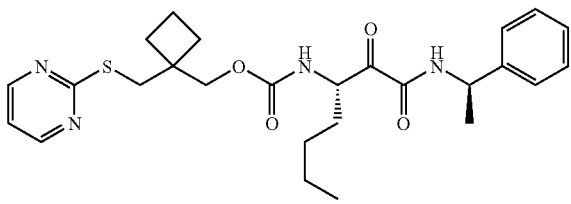

To a solution of 0.135 g (0.27 mmol) of {1-[(2-pyrimidinylsulfanyl)methyl]cyclobutyl}methyl (1S)-1-(1-hydroxy-2-oxo-2-{[(1R)-1-phenylethyl]amino}ethyl)pentylcarbamate in 2.0 mL of dichloromethane was added 0.031 g (0.375 mmol) of sodium bicarbonate followed by the addition of 0.137 g (0.32 mmol) of Dess-Martin periodinane. The reaction was stirred for 15 min and poured directly onto a silica gel column eluting with ethyl acetate:hexane (3:7) as the eluent to afford 0.094 g (70%) of {1-[(2-pyrimidinylsulfanyl)methyl]cyclobutyl}methyl (1S)-1-(oxo{[(1R)-1-phenylethyl]amino}acetyl)pentylcarbamate as a colorless oil. $^1$H NMR (300 MHz, CDCl$_3$) δ 8.43 (d, J=5 Hz, 2H), 7.31-7.08 (m, 6H), 6.88 (t, J=5 Hz, 1H), 5.25 (d, J=7 Hz, 1H), 4.89-5.20 (m, 2H), 4.08 (s, 2H), 3.43 (s, 2H), 2.03-1.80 (m, 6H), 1.79-1.42 (m, 5H), 1.41-1.25 (m, 4H), 0.81 (br s, 3H). LC-MS m/z 499 (M+H).

Example 24

{1-[(1,3-benzoxazol-2-ylsulfanyl)methyl]cyclobutyl}methyl (1S)-1-(oxo{[(1R)-1-phenylethyl]amino}acetyl)pentylcarbamate

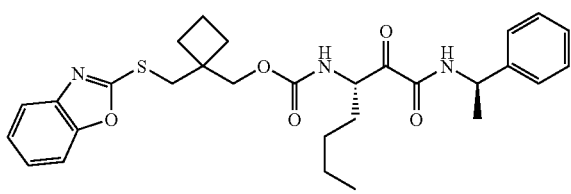

Example 24a

Preparation of {1-[(1,3-benzoxazol-2-ylsulfanyl)methyl]cyclobutyl}methanol

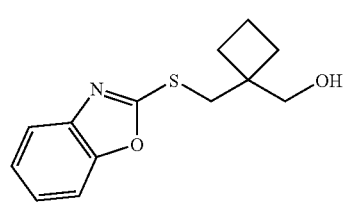

The title compound was prepared using the same experimental procedure as in example 19a using {1-[(1,3-benzoxazol-2-ylsulfanyl)methyl]cyclobutyl}methanol as the thiol component. $^1$H NMR (300 MHz, CDCl$_3$) δ 7.67-7.25 (m, 4H), 3.61 (s, 2H), 3.46 (br s, 1H), 3.35 (s, 2H), 1.54-1.31 (m, 6H). GC-MS m/z 250 (M+H).

Example 24b

Preparation of {1-[(1,3-benzoxazol-2-ylsulfanyl)methyl]cyclobutyl}methyl (1S)-1-(1-hydroxy-2-oxo-2-{[(1R)-1-phenylethyl]amino}ethyl)pentylcarbamate

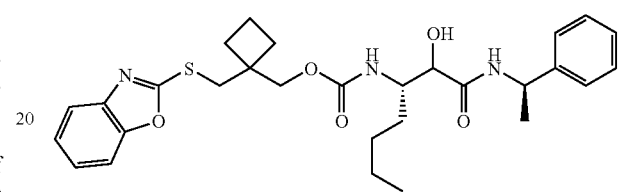

The title compound was prepared using the same experimental procedure as in example 20b with {1-[(1,3-benzoxazol-2-ylsulfanyl)methyl]cyclobutyl}methanol as the alcohol component and (3S)-3-amino-2-hydroxy-N-[(1R)-1-phenylethyl]heptanamide as the amino alcohol component. $^1$H NMR (300 MHz, CDCl$_3$) δ 7.60 (d, J=7 Hz, 1H), 7.45 (d, J=7 Hz, 1H), 7.44-7.24 (m, 7H), 7.16 (d, J=8 Hz, 1H), 5.62 (m, 1H), 5.14 (m, 1H), 4.80 (br s,1H), 4.36-4.09 (m, 3H), 3.87 (m, 1H), 3.63 (s, 2H), 2.02-1.68 (m, 8H), 1.63-1.26 (m, 7H), 0.92 (m, 3H). LC-MS m/z 540 (M+H).

Example 24c

Preparation of {1-[(1,3-benzoxazol-2-ylsulfanyl)methyl]cyclobutyl}methyl (1S)-1-(oxo{[(1R)-1-phenylethyl]amino}acetyl)pentylcarbamate

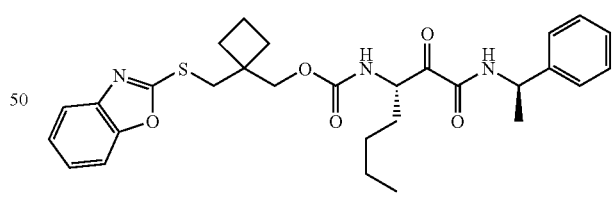

The title compound was prepared using the same experimental procedure as in example 20c with {1-[(1,3-benzoxazol-2-ylsulfanyl)methyl]cyclobutyl}methyl (1S)-1-(1-hydroxy-2-oxo-2-{[(1R)-1-phenylethyl]amino}ethyl)pentylcarbamate as the starting alcohol. $^1$H NMR (300 MHz, CDCl$_3$) δ 7.53 (d, J=7 Hz, 1H), 7.37 (d, J=8 Hz, 1H), 7.31-7.07 (m, 7H), 5.26 (d, J=7 Hz, 1H), 5.07-4.98 (m, 3H), 4.12 (s, 2H), 3.58 (s, 2H), 2.03-1.81 (m, 6H), 1.48 (d, J=6 Hz, 3H), 1.42-1.23 (m, 6H), 0.80 (t, J=6 Hz, 3H). LC-MS m/z 538 (M+H).

Example 25

{1-[(1,3-thiazol-2-yloxy)methyl]cyclobutyl}methyl (1S)-1-(oxo{[(1R)-1-phenylethyl]amino}acetyl)pentylcarbamate

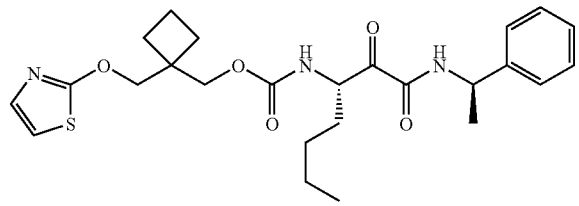

Example 25a

Preparation of {1-[(1,3-thiazol-2-yloxy)methyl]cyclobutyl}methanol

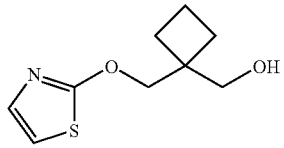

To a solution of 0.5 g (4.31 mmol) of [1-(hydroxymethyl)cyclobutyl]methanol in 15 mL of N,N-dimethylformamide:tetrahydrofuran (1:1), was added a 60% dispersion of 0.165 g (4.31 mmol) sodium hydride in oil. After stirring for 15 min, 0.71 g (4.31 mmol) of 2-bromothiazole was added and the contents refluxed for 3 h. A saturated solution of sodium bicarbonate was added followed by ethyl acetate. The organic phase was isolated, dried with magnesium sulfate and concentrated under vacuum. The crude product was purified by silica gel chromatography eluting with ethyl acetate:hexane (4:6) to afford 0.340 g (40%) of {1-[(1,3-thiazol-2-yloxy)methyl]cyclobutyl}methanol as a colorless oil. $^1$H NMR (300 MHz, CDCl$_3$) δ 7.05 (d, J=4 Hz, 1H), 6.64 (d, J=4 Hz, 1H), 4.51 (s, 2H), 3.59 (s, 2H), 2.03-1.72 (m, 6H). GC-MS m/z 200 (M+H).

Example 25b

Preparation of {1-[(1,3-thiazol-2-yloxy)methyl]cyclobutyl}methyl (1S)-1-(1-hydroxy-2-oxo-2-{[(1R)-1-phenylethyl]amino}ethyl)pentylcarbamate

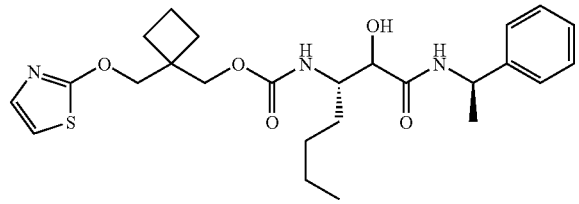

The title compound was prepared using the same experimenta; procedure as in example 20b using {1-[(1,3-thiazol-2-yloxy)methyl]cyclobutyl}methanol as the alcohol component and (3S)-3-amino-2-hydroxy-N-[(1R)-1-phenylethyl]heptanamide as the aminoalcohol component. $^1$H NMR (300 MHz, CDCl$_3$) δ 8.25 (d, J=6 Hz, 1H), 7.34-7.26 (m, 5H), 6.63 (d, J=6 Hz, 1H), 5.44 (m, 1H), 5.07 (m, 1H), 4.94 (d, J=8 Hz, 1H), 4.54 (d, J=5 Hz, 1H), 4.37-4.18 (m, 5H), 3.74 (m, 1H), 1.47 (d, J=7 Hz, 3H), 1.42-0.91 (m, 12 H), 0.81 (m, 3H). LC-MS m/z 490 (M+H).

Example 25c

Preparation of {1-[(1,3-thiazol-2-yloxy)methyl]cyclobutyl}methyl (1S)-1-(oxo{[(1R)-1-phenylethyl]amino}acetyl)pentylcarbamate

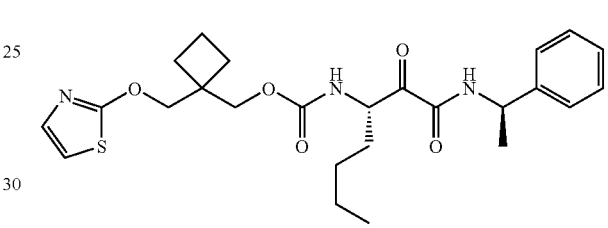

The title compound was prepared using the same experimental procedure as in example 23c using {1-[(1,3-thiazol-2-yloxy)methyl]cyclobutyl}methyl (1S)-1-(1-hydroxy-2-oxo-2-{[(1R)-1-phenylethyl]amino}ethyl)pentylcarbamate as the starting alcohol. $^1$H NMR (300 MHz, CDCl$_3$) δ 7.35-7.26 (m, 6H), 7.11 (s, 1H), 6.67 (s, 1H), 5.27-5.08 (m, 3H), 4.40 (s, 2H), 4.18 (s, 2H), 1.98-1.81 (m, 6H), 1.65 (m, 2H), 1.53 (d , J=6 Hz, 3H), 1.42-1.21 (m, 4H), 0.85 (br s, 3H). LC-MS m/z 488 (M+H).

Example 26

(1-{[(3-phenyl-1,2,4-thiadiazol-5-yl)oxy]methyl}cyclobutyl)methyl (1S)-1-(oxo{[(1R)-1-phenylethyl]amino}acetyl)pentylcarbamate

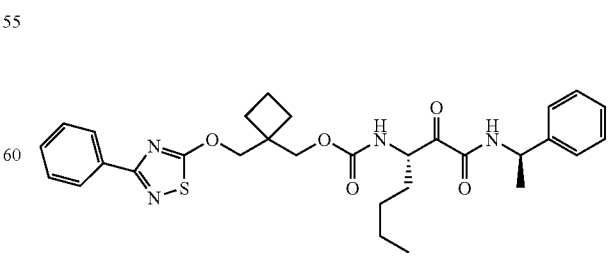

Example 26a

Preparation of (1-{[(3-phenyl-1,2,4-thiadiazol-5-yl)oxy]methyl}cyclobutyl)methanol

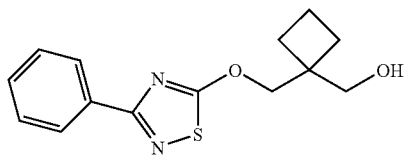

The title compound was prepared using the same experimental procedure as in example 25a from [1-(hydroxymethyl)cyclobutyl]methanol and 5-chloro-3-phenyl-1,2,4-thiadiazole. $^1$H NMR (300 MHz, CDCl$_3$) δ 8.10 (m, 2H), 7.39 (m, 3H), 4.63 (s, 2H), 3.62 (d, J=6 Hz, 2H), 2.71 (t, J=6 Hz, 1H), 1.88-1.97 (m, 6H). GC-MS m/z 277 (M+H).

Example 26b

Preparation of (1-{[(3-phenyl-1,2,4-thiadiazol-5-yl)oxy]methyl}cyclobutyl)methyl (1S)-1-(1-hydroxy-2-oxo-2-{[(1R)-1-phenylethyl]amino}ethyl)pentylcarbaate

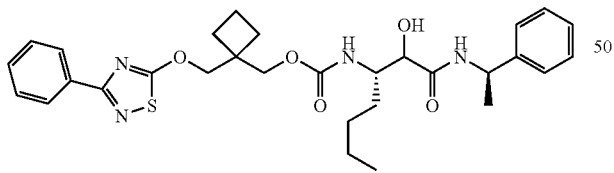

The title compound was prepared using the same experimental procedure as in example 20b using (1-{[(3-phenyl-1,2,4-thiadiazol-5-yl)oxy]methyl}cyclobutyl)methanol as the alcohol component and (3S)-3-amino-2-hydroxy-N-[(1R)-1-phenylethyl]heptanamide as the aminoalcohol component. $^1$H NMR (300 MHz, CDCl$_3$) δ 8.23 (m, 2H), 7.48-7.26 (m, 8H), 7.13 (d, J=8 Hz, 1H), 5.63 (m, 1H), 5.07 (m, 1H), 4.78 (d, J=6 Hz, 1H), 4.57 (s, 2H), 4.27-4.10 (m, 3H), 3.85 (m, 1H), 2.09-1.80 (m, 6H), 1.47 (d, J=7 Hz, 3H), 1.32-1.25 (m, 6H), 0.94 (m, 3H). LC-MS m/z 567 (M+H).

Example 26c

Preparation of (1-{[(3-phenyl-1,2,4-thiadiazol-5-yl)oxy]methyl}cyclobutyl)methyl (1S)-1-(oxo{[(1R)-1-phenylethyl]amino}acetyl)pentylcarbamate

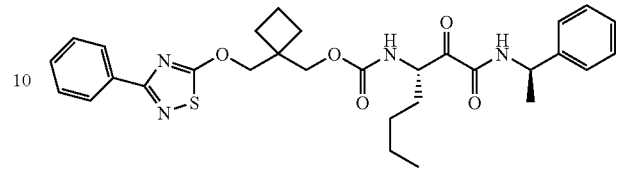

The title compound was prepared using the same experimental procedure as in example 23c using (1-{[(3-phenyl-1,2,4-thiadiazol-5-yl)oxy]methyl}cyclobutyl)methyl (1S)-1-(1-hydroxy-2-oxo-2-{[(1R)-1-phenylethyl]amino}ethyl)pentylcarbamate as the starting alcohol. $^1$H NMR (300 MHz, CDCl$_3$) δ 8.23 (m, 2H), 7.49-7.29 (m, 8H), 7.12 (d, J=8 Hz, 1H), 5.34-5.10 (m, 3H), 4.60 (s, 2H), 4.26 (s, 2H), 2.08-1.99 (m, 6H), 1.55 (d, J=7 Hz, 3H), 1.34-1.24 (m, 6H), 0.88 (br s, 3H). LC-MS m/z 565 (M+H).

Example 27

[1-({[2-(4-phenyl-1-piperazinyl)-4-pyrimidinyl]oxy}methyl)cyclobutyl]methyl (1S)-1-(oxo{[(1R)-1-phenylethyl]amino}acetyl)pentylcarbamate

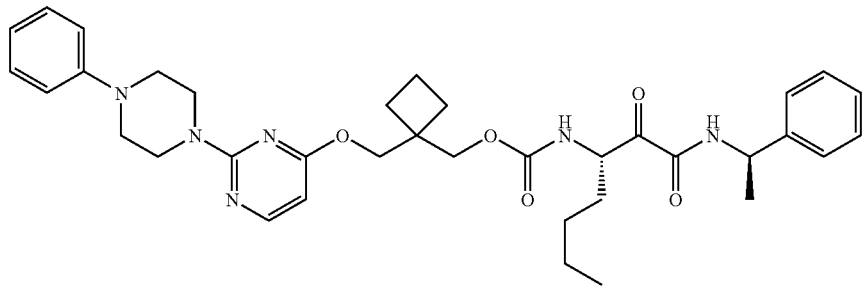

Example 27a

Preparation of [1-({[2-(4-phenyl-1-piperazinyl)-4-pyrimidinyl]oxy}methyl)cyclobutyl]methanol

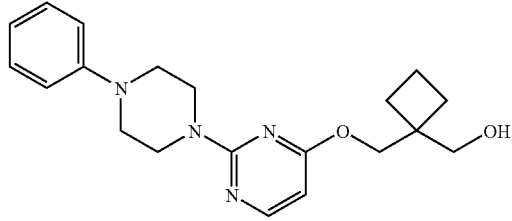

The title compound was prepared from (1-{[(2-chloro-4-pyrimidinyl)oxy]methyl}cyclobutyl)methanol using the same experimental procedure as in example 21a using 1-phenylpiperazine. $^1$H NMR (300 MHz, CDCl$_3$) δ 8.01 (d, J=6 Hz, 1H), 7.21 (m, 2H), 6.92-6.82 (m, 3H), 5.93 (d, J=6 Hz, 1H), 4.37 (s, 2H), 3.90 (m, 4H), 3.58 (s, 2H), 3.18 (m, 4H), 2.54 (br s, 1H).

Example 27b

Preparation of [1-({[2-(4-phenyl-1-piperazinyl)-4-pyrimidinyl]oxy}methyl)cyclobutyl]methyl (1S)-1-(1-hydroxy-2-oxo-2-{[(1R)-1-phenylethyl]amino}ethyl) pentylcarbamate

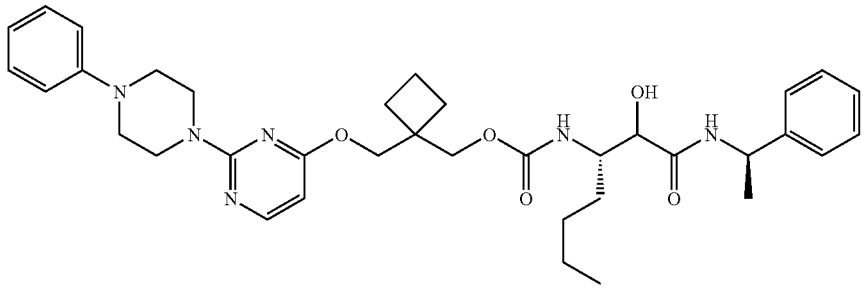

The title compound was prepared using the same experimental procedure as in example 20b using [1-({[2-(4-phenyl-1-piperazinyl)-4-pyrimidinyl]oxy}methyl)cyclobutyl]methanol as the alcohol component and (3S)-3-amino-2-hydroxy-N-[(1R)-1-phenylethyl]heptanamide as the aminoalcohol component. $^1$H NMR (300 MHz, CDCl$_3$) δ 8.09 (d, J=6 Hz, 1H), 7.35-6.90 (m, 11H), 6.03 (d, J=6 Hz, 1H), 5.15-5.06 (m, 2H), 4.98 (br s, 1H), 4.46-4.12 (m, 5H), 4.01 (m, 4H), 3.98 (m, 1H), 3.28 (m, 4H), 2.08-1.61 (m, 8H), 1.51 (d, J=7 Hz, 3H), 1.32-1.27 (m, 4H), 0.88 (m, 3H). LC-MS m/z 645 (M+H).

Example 27c

Preparation of [1-({[2-(4-phenyl-1-piperazinyl)-4-pyrimidinyl]oxy}methyl)cyclobutyl]methyl (1S)-1-(oxo{[(1R)-1-phenylethyl]amino}acetyl)pentylcarbamate The title compound was prepared using the same experimental procedure as in example 23c using [1-({[2-(4-phenyl-1-piperazinyl)-4-pyrimidinyl]oxy}methyl) cyclobutyl] methyl (1S)-1-(1-hydroxy-2-oxo-2-{[(1R)-1-phenylethyl]amino}ethyl) pentylcarbamate as the alcohol component. $^1$H NMR (300 MHz, CDCl$_3$) δ 8.10 (d, J=6 Hz, 1H), 7.41-7.30 (m, 8H), 7.14-6.90 (m, 3H), 6.04 (d, J=6 Hz, 1H), 5.32-5.08 (m, 3H), 4.33 (s, 2H), 4.22 (s, 2H), 4.0 (t, J=5 Hz, 4H), 3.28 (t, J=5 Hz, 4H), 2.12-1.98 (m, 7H), 1.96 (m, 4H), 1.33-1.27 (m, 4H), 0.89 (t, J=6 Hz, 3H). LC-MS m/z 643 (M+H).

Example 28

(1-{[(1-phenyl-1H-imidazol-2-yl)sulfanyl]methyl}cyclobutyl)methyl (1S)-1-(oxo{[(1R)-1-phenylethyl]amino}acetyl)pentylcarbamate

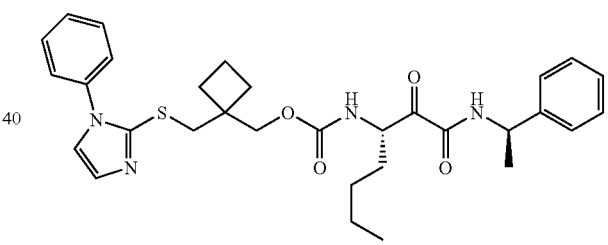

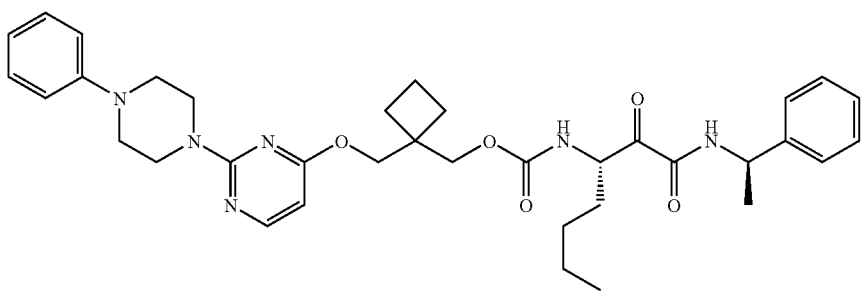

Example 28a

Preparation of (7-{[(1-phenyl-1H-imidazol-2-yl)sulfanyl]methyl}cyclobutyl)methanol

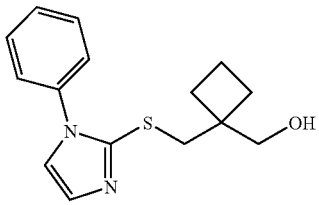

The title compound was prepared using the same experimental procedure as in example 19a using [1-(hydroxymethyl)cyclobutyl]methanol and 1-phenyl-1H-imidazole-2-thiol. $^1$H NMR (300 MHz, CDCl$_3$) δ 7.50-7.07 (m, 7H), 3.63 (s, 2H), 3.40 (s, 2H), 1.93-1.69 (m, 6H). GC-MS m/z 275 (M+H).

Example 28b

Preparation of (1-{[(1-phenyl-1H-imidazol-2-yl)sulfanyl]methyl}cyclobutyl)methyl (1S)-1-(1-hydroxy-2-oxo-2-{[(1R)-1-phenylethyl]amino}ethyl)pentylcarbamate

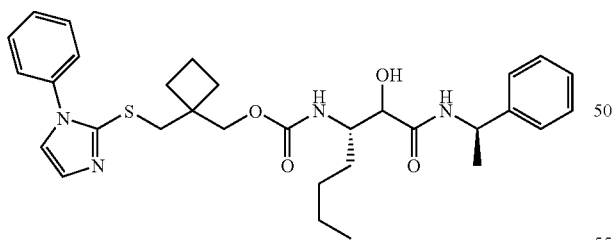

The title compound was prepared using the same experimental procedure as in example 20b using (1-{[(1-phenyl-1H-imidazol-2-yl)sulfanyl]methyl}cyclobutyl)methanol as the alcohol component and (3S)-3-amino-2-hydroxy-N-[(1R)-1-phenylethyl]heptanamide as the aminoalcohol component. $^1$H NMR (300 MHz, CDCl$_3$) δ 7.50-7.06 (m, 13 H), 5.55 (br s, 1H), 5.20-5.09 (m, 2H), 4.10 (br s, 1H), 4.02-3.87 (m, 3H), 3.30 (s, 2H), 2.04-1.79 (m, 6H), 1.50-1.25 (m, 9H), 0.79 (m, 3H). LC-MS m/z 565 (M+H).

Example 28c

Preparation of (1-{[(1-phenyl-1H-imidazol-2-yl)sulfanyl]methyl}cyclobutyl)methyl (1S)-1-(oxo{[(1R)-1-phenylethyl]amino}acetyl)pentylcarbamate

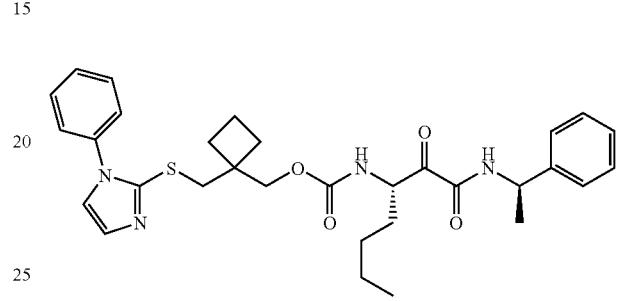

The title compound was prepared using the same experimental procedure as in example 23c using (1-{[(1-phenyl-1H-imidazol-2-yl)sulfanyl]methyl}cyclobutyl)methyl (1S)-1-(1-hydroxy-2-oxo-2-{[(1R)-1-phenylethyl]amino}ethyl)pentylcarbamate as the starting alcohol component. $^1$H NMR (300 MHz, CDCl$_3$) δ 7.50-7.06 (m, 13 H), 5.46 (m, 1H), 5.15-5.05 (m, 2H), 4.0 (s, 2H), 3.47 (s, 2H), 2.08-1.65 (m, 6H), 1.52 (d, J=7 Hz, 3H), 1.39-0.92 (m, 6H), 0.85 (t, J=7 Hz, 3H). LC-MS m/z 563 (M+H).

Example 29

{1-[(thieno[3,2-d]pyrimidin-4-yloxy)methyl]cyclobutyl}methyl (1S)-1-(oxo{[(1R)-1-phenylethyl]amino}acetyl)pentylcarbamate

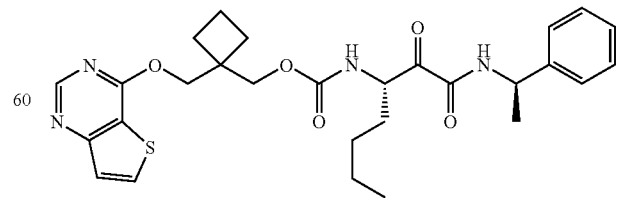

Example 29a

Preparation of {1-[(thieno[3,2-d]pyrimidin-4-yloxy)methyl]cyclobutyl}methanol

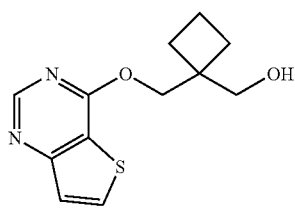

The title compound was prepared using the same experimental procedure as in example 25a using [1-(hydroxymethyl)cyclobutyl]methanol and 4-chlorothieno[3,2-d]pyrimidine. $^1$H NMR (300 MHz, CDCl$_3$) δ 8.70 (s, 1H), 7.87 (d, J=5 Hz, 1H), 7.49 (d, J=5 Hz, 1H), 4.69 (s, 2H), 3.61 (d, J=6 Hz, 2H), 3.36 (t, J=6 Hz, 1H), 2.01-1.82 (m, 6H). GC-MS m/z 251 (M+H).

Example 29b

Preparation of {1-[(thieno[3,2-d]pyrimidin-4-yloxy)methyl]cyclobutyl}methyl (1S)-1-(1-hydroxy-2-oxo-2-{[(1R)-1-phenylethyl]amino}ethyl)pentylcarbamate

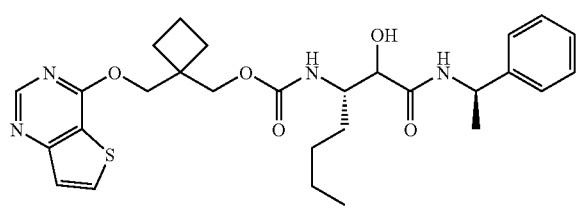

The title compound was prepared using the same experimental procedure as in example 20b using {1-[(thieno[3,2-d]pyrimidin-4-yloxy)methyl]cyclobutyl}methanol as the alcohol component and (3S)-3-amino-2-hydroxy-N-[(1R)-1-phenylethyl]heptanamide as the aminoalcohol component. $^1$H NMR (300 MHz, CDCl$_3$) δ 8.71 (s, 1H), 7.82 (m, 1H), 7.52-7.09 (m, 7H), 5.11-5.04 (m, 2H), 4.83 (m, 1H), 4.54 (s, 2H), 4.36-4.10 (m, 3H), 3.79 (m, 1H), 2.03-1.88 (m, 6H), 1.83-1.23 (m, 9H), 0.82 (m, 3H). LC-MS m/z 541 (M+H).

Example 29c

Preparation of {1-[(thieno[3,2-d]pyrimidin-4-yloxy)methyl]cyclobutyl}methyl (1S)-1-(oxo{[(1R)-1-phenylethyl]amino}acetyl)pentylcarbamate

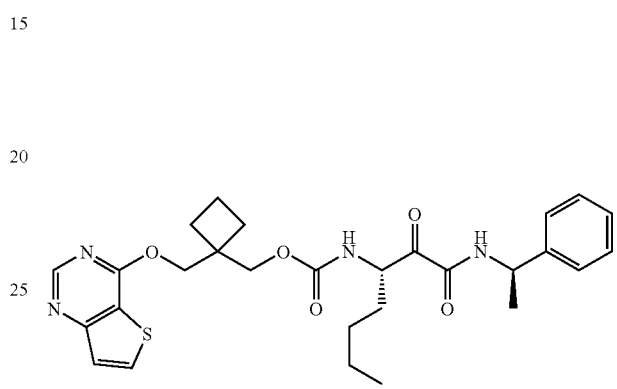

The title compound was prepared using the same experimental procedure as in example 23c using {1-[(thieno[3,2-d]pyrimidin-4-yloxy)methyl]cyclobutyl}methyl (1S)-1-(1-hydroxy-2-oxo-2-{[(1R)-1-phenylethyl]amino}ethyl)pentylcarbamate as the starting alcohol component. $^1$H NMR (300 MHz, CDCl$_3$) δ 8.75 (s, 1H), 7.83 (d, J=6 Hz, 1H), 7.51 (d, J=5 Hz, 1H), 7.41-7.12 (m, 6H), 5.29 (d, J=8 Hz, 1H), 5.14-5.03 (m, 2H), 4.59 (s, 2H), 4.23 (s, 2H), 2.08-1.68 (m, 6H), 1.65-1.51 (m, 5H), 1.39-1.27 (m, 4H), 0.83 (t, J=6 Hz, 3H). LC-MS m/z 539 (M+H).

Example 30

{1-[(2-pyrimidinyloxy)methyl]cyclobutyl}methyl (1S)-1-(oxo {[(1R)-1-phenylethyl]amino}acetyl)pentylcarbamate

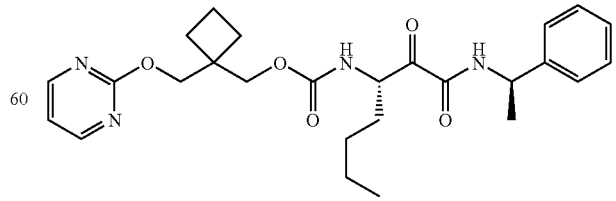

Example 30a

Preparation of {1-[(2-pyrimidinyloxy)methyl]cyclobutyl}methanol

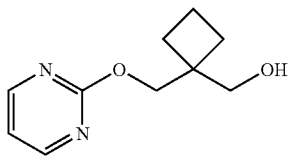

The title compound was prepared using the same experimental procedure as in example 25a from [1-(hydroxymethyl)cyclobutyl]methanol and 2-chloropyrimidine. $^1$H NMR (300 MHz, CDCl$_3$) δ 8.50-8.47 (m, 2H), 6.95-6.89 (m, 1H), 4.48 (s, 2H), 3.63 (d, J=6 Hz, 2H), 3.02 (t, J=6 Hz, 1H), 2.01-1.78 (m, 6H). GC-MS m/z 195 (M+H).

Example 30b

Preparation of {1-[(2-pyrimidinyloxy)methyl]cyclobutyl}methyl (1S)-1-(1-hydroxy-2-oxo-2-{[(1R)-1-phenylethyl]amino}ethyl)pentylcarbamate

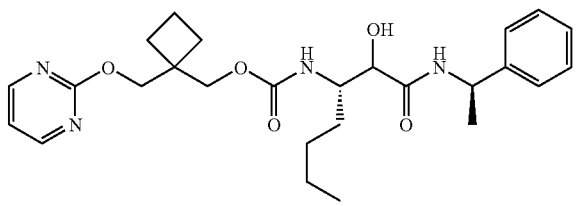

The title compound was prepared using the same experimental procedure as in example 20b from {1-[(2-pyrimidinyloxy)methyl]cyclobutyl}methanol as the alcohol component and (3S)-3-amino-2-hydroxy-N-[(1R)-1-phenylethyl]heptanamide as the aminoalcohol component. $^1$H NMR (300 MHz, CDCl$_3$) δ 8.46 (m, 2H), 7.26 (m, 6H), 6.92-6.72 (m, 1H), 5.29 (m, 1H), 5.05 (m, 2H), 4.51 (s, 2H), 4.46-3.94 (m, 3H), 3.83 (m, 1H), 2.03-1.80 (m, 8H), 1.48-1.23 (m, 7H), 0.82 (m, 3H). LC-MS m/z 485 (M+H).

Example 30c

Preparation of {1-[(2-pyrimidinyloxy)methyl]cyclobutyl}methyl (1S)-1-(oxo{[(1R)-1-phenylethyl]amino}acetyl)pentylcarbamate

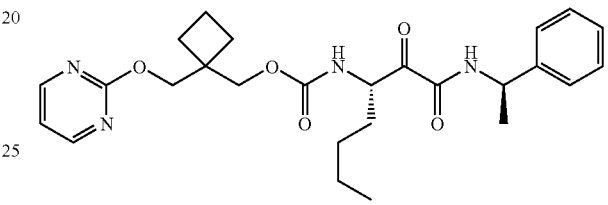

The title compound was prepared using the same experimental procedure as in example 23c from {1-[(2-pyrimidinyloxy)methyl]cyclobutyl}methyl (1S)-1-(1-hydroxy-2-oxo-2-{[(1R)-1-phenylethyl]amino}ethyl)pentylcarbamate as the alcohol component. $^1$H NMR (300 MHz, CDCl$_3$) δ 8.50 (d, J=5 Hz, 2H), 7.37-7.26 (m, 5H), 7.08 (d, J=7 Hz, 1H), 6.91 (t, J=5 Hz, 1H), 5.25 (d, J=8 Hz, 1H), 5.11-5.04 (m, 2H), 4.35 (s, 2H), 4.24 (s, 2H), 2.00-1.94 (m, 6H), 1.52 (d, J=7 Hz, 3H), 1.36-1.27 (m, 6H), 0.82 (t, J=7 Hz, 3H). LC-MS m/z 487 (M+H).

Example 31

[1-({[4-(4-methylphenyl)-1,3-thiazol-2-yl]oxy}methyl)cyclobutyl]methyl (1S)-1-(oxo{[(1R)-1-phenylethyl]amino}acetyl)pentylcarbamate

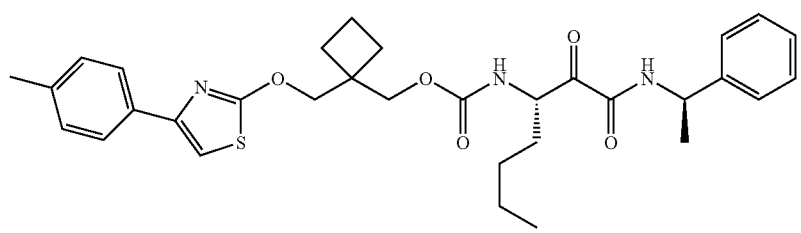

Example 31a

Preparation of [1-({[4-(4-methylphenyl)-1,3-thiazol-2-yl]oxy}methyl)cyclobutyl]methanol

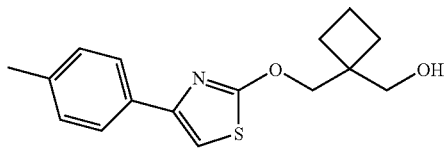

The title compound was prepared using the same experimental procedure as in example 25a from [1-(hydroxymethyl)cyclobutyl]methanol and 2-chloro-4-(4-methylphenyl)-1,3-thiazole. $^1$H NMR (300 MHz, CDCl$_3$) δ 7.61 (d, J=8 Hz, 2H), 7.16 (d, J=8 Hz, 2H), 6.78 (s, 1H), 4.62 (s, 2H), 3.77 (t, J=7 Hz, 1H), 3.60 (d, J=7 Hz, 2H), 2.35 (s, 3H), 2.04-1.90 (m, 6H). GC-MS m/z 290 (M+H).

Example 31b

Preparation of [1-({[4-(4-methylphenyl)-1,3-thiazol-2-yl]oxy}methyl)cyclobutyl]methyl (1S)-1-(1-hydroxy-2-oxo-2-{[(1R)-1-phenylethyl]amino}ethyl)pentylcarbamate

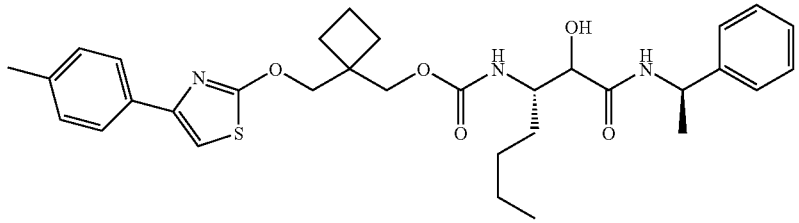

The title compound was prepared using the same experimental procedure as in example 20b from [1-({[4-(4-methylphenyl)-1,3-thiazol-2-yl]oxy}methyl)cyclobutyl]methanol as the alcohol component and (3S)-3-amino-2-hydroxy-N-[(1R)-1-phenylethyl]heptanamide as the amino alcohol component. $^1$H NMR (300 MHz, CDCl$_3$) δ 7.69 (m, 2H), 7.33-7.01 (m, 7H), 6.79 (m, 2H), 5.06-4.99 (m, 3H), 4.44 (m, 2H), 4.21-4.12 (m, 3H) 3.81 (m, 1H), 2.37 (s, 3H), 2.05-1.73 (m, 6H), 1.68-1.24 (m, 9H), 0.83 (m, 3H). LC-MS m/z 580 (M+H).

Example 31c

Preparation of [1-({[4-(4 methylphenyl)-1,3-thiazol-2-yl]oxy}methyl)cyclobutyl]methyl (1S)-1-(oxo{[(1R)-1-phenylethyl]amino}acetyl)pentylcarbamate

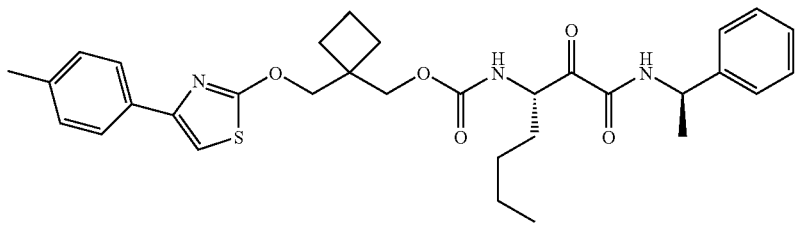

The title compound was prepared using the same experimental procedure as in example 23c from [1-({[4-(4-methylphenyl)-1,3-thiazol-2-yl]oxy}methyl)cyclobutyl]methyl (1S)-1-(1-hydroxy-2-oxo-2-{[(1R)-1-phenylethyl]amino}ethyl)pentylcarbamate as the alcohol component. $^1$H NMR (300 MHz, CDCl$_3$) δ 7.70 (d, J=8 Hz, 2H), 7.34-7.18 (m, 7H), 7.08 (d, J=7 Hz, 1H), 6.79(s, 1H), 5.26 (d, J=8 Hz, 1H), 5.16-5.40 (m, 2H), 4.49 (s, 2H), 4.21 (s, 2H), 2.36 (s, 3H), 2.03-1.93 (m, 6H), 1.37-1.29 (m, 4H), 1.52 (m, 5H), 0.84 (t, J=6 Hz, 3H). LC-MS 578 (M+H).

Example 32

(1-{[(6-methyl-4-phenylpyridazin-3-yl)oxy]methyl}cyclobutyl)methyl (1R)-1-(oxo{[(1R)-1-phenylethyl]amino}acetyl)pentylcarbamate

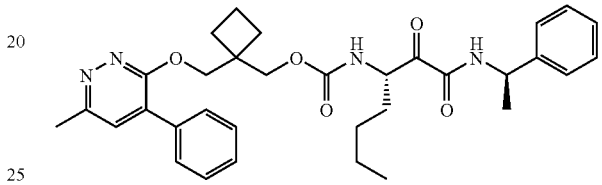

Example 32a

Preparation of (1-{[(6-methyl-4-phenyl-3-pyridazinyl)oxy]methyl}cyclobutyl)methanol

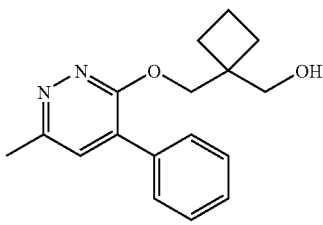

The title compound was prepared using the same experimental procedure as in example 25a from [1-(hydroxymethyl)cyclobutyl]methanol and 3-chloro-6-methyl-4-phenylpyridazine. ¹H NMR (300 MHz, CDCl₃) δ 7.58-7.25 (m, 6H), 4.64 (s, 2H), 3.59 (d, J=6 Hz, 2H), 3.05 (t, J=7 Hz, 1H), 2.63 (s, 3H), 2.00-1.73 (m, 6H). GC-MS m/z 285 (M+H).

Example 32b

Preparation of (1-{[(6-methyl-4-phenylpyridazin-3-yl)oxy]methyl}cyclobutyl)methyl (1R)-1-(1-hydroxy-2-oxo-2-{[(1R)-1-phenylethyl]amino}ethyl)pentylcarbamate

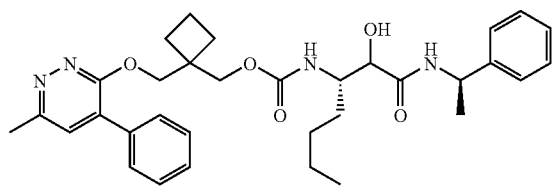

The title compound was prepared using the same experimental procedure as in example 20b from (1-{[(6-methyl-4-phenyl-3-pyridazinyl)oxy]methyl}cyclobutyl) methanol as the alcohol component and (3S)-3-amino-2-hydroxy-N-[(1R)-1-phenylethyl]heptanamide as the aminoalcohol component. ¹H NMR (300 MHz, CDCl₃) δ 7.54-7.22 (m, 12H), 6.12 (m, 1H), 5.22-4.99 (m, 2H), 4.54 (m, 1H), 4.23-3.89 (m, 4H), 2.84 (br s, 1H), 2.59 (m, 3H), 2.04-1.90 (m, 6H), 1.50-1.23 (m, 9H), 0.79 (m, 3H). LC-MS m/z 575 (M+H).

Example 32c

Preparation of (1-{[(6-methyl-4-phenylpyridazin-3-yl)oxy]methyl}cyclobutyl)methyl (1R)-1-(oxo{[(1R)-1-phenylethyl]amino}acetyl)pentylcarbaate

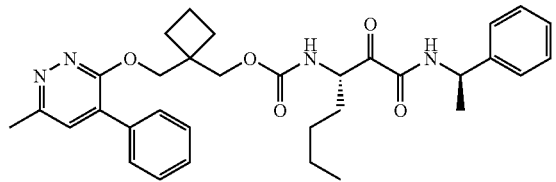

The title compound was prepared using the same experimental procedure as in example 23c from (1-{[(6-methyl-4-phenyl-3-pyridazinyl)oxy]methyl}cyclobutyl)methyl (1S)-1-(1-hydroxy-2-oxo-2-{[(1R)-1-phenylethyl]amino}ethyl)pentylcarbamate as the alcohol component. ¹H NMR (300 MHz, CDCl₃) δ 7.58-7.14 (m, 12H), 5.19-5.06 (m, 3H), 4.53 (s, 2H), 4.12 (s, 2H), 2.65 (s, 3H), 2.03-1.92 (m, 6H), 1.53 (m, 2H), 1.52 (d, J=7 Hz, 3H), 1.41-1.28 (m, 4H), 0.83 (br s, 3H). LC-MS m/z 573 (M+H).

Example 33

[1-({[4-(4-chloro phenyl)-2-pyrimidinyl]sulfanyl}methyl)cyclobutyl]methyl (1S)-1-(oxo{[(1R)-1-phenylethyl]amino}acetyl)pentylcarbamate

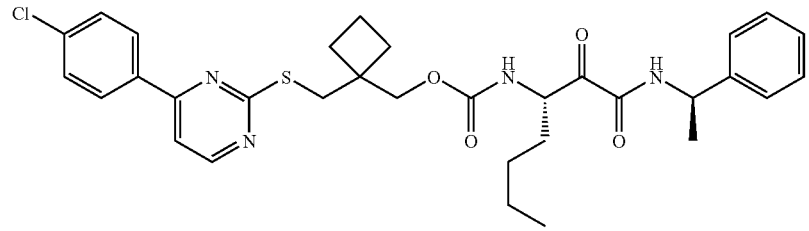

Example 33a

Preparation of [1-({[4-(4-chlorophenyl)-2-pyrimidinyl]sulfanyl}methyl) cyclobutyl]methanol

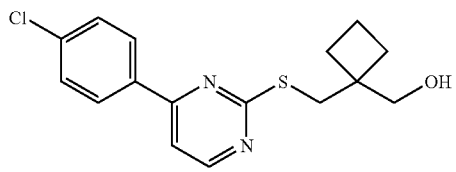

The title compound was prepared using the same experimental procedure as in example 19a from [1-(hydroxymethyl)cyclobutyl]methanol and 4-(4-chlorophenyl)-2-pyrimidinethiol. ¹H NMR (300 MHz, CDCl₃) δ 8.49 (d, J=5 Hz, 1H), 7.95 (d, J=9 Hz, 2H), 7.44 (d, J=9 Hz, 2H), 7.32 (d, J=6 Hz, 1H), 4.18 (t, J=7 Hz, 1H), 3.54(d, J=7 Hz, 2H), 3.47 (s, 2H), 2.03-1.69 (m, 6H). GC-MS m/z 320 (M+H).

Example 33b

Preparation of [1-({[4(4-chlorophenyl)-2-pyrimidinyl]sulfanyl}methyl)cyclobutyl]methyl (1S)-1-(1-hydroxy-2-oxo-2-{[(1R)-1-phenylethyl]amino}ethyl) pentylcarbamate

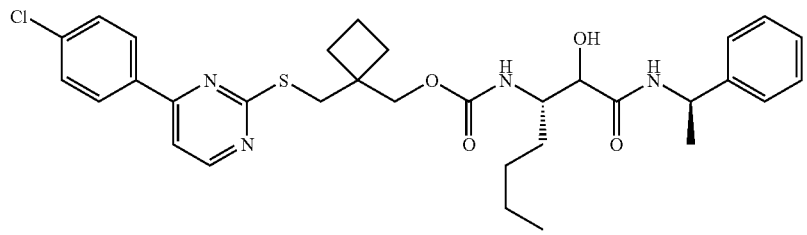

The title compound was prepared using the same experimental procedure as in example 20b from [1-({[4-(4-chlorophenyl)-2-pyrimidinyl]sulfanyl}methyl) cyclobutyl] methanol as the alcohol component and (3S)-3-amino-2-hydroxy-N-[(1R)-1-phenylethyl]heptanamide as the aminoalcohol component. $^1$H NMR (300 MHz, CDCl$_3$) δ 8.50 (d, J=5 Hz, 1H), 7.99 (d, J=8 Hz, 2H), 7.44 (d, J=8 Hz, 2H), 7.30-7.15 (m, 7H), 5.10-4.93 (m, 3H), 4.15 (m, 3H), 3.80 (m, 1H), 3.52 (s, 2H), 2.04-1.91 (m, 6H), 1.82-1.23 (m, 9H), 0.82 (m, 3H). LC-MS m/z 611 (M+H).

Example 33c

Preparation of [1-({[4-(4-chlorophenyl)-2-pyrimidinyl]sulfanyl}methyl)cyclobutyl]methyl (1S)-1-(oxo{[(1R)-1-phenylethyl]amino}acetyl)pentylcarbamate

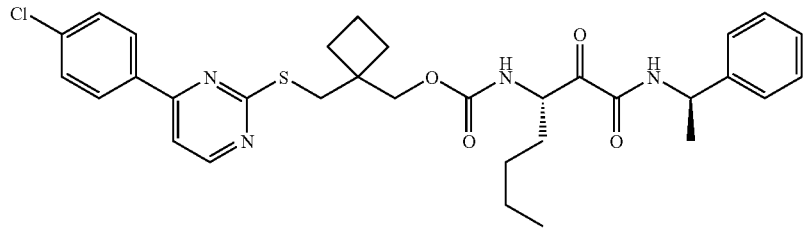

The title compound was prepared using the same experimental procedure as in example 23c from [1-({[4-(4-chlorophenyl)-2-pyrimidinyl]sulfanyl}methyl) cyclobutyl]methyl (1S)-1-(1-hydroxy-2-oxo-2-{[(1R)-1-phenylethyl]amino}ethyl) pentylcarbamate as the alcohol component. $^1$H NMR (300 MHz, CDCl$_3$) δ 8.52 (d, J=5 Hz, 1H), 8.02 (d, J=8 Hz, 2H), 7.45 (d, J=8 Hz, 2H), 7.34-7.25 (m, 6H), 7.09 (d, J=7 Hz, 1H), 5.24-5.04 (m, 3H), 4.17 (s, 2H), 3.55 (s, 2H), 2.03-1.95 (m, 6H), 1.56 (m, 2H), 1.52 (d, J=7 Hz, 3H), 1.38-1.28 (m, 4H), 0.84 (t, J=6 Hz, 3H). LC-MS m/z 609 (M+H).

Example 34

[1-({[5-(4-chlorophenyl)-1-methyl-1H-imidazol-2-yl]sulfanyl}methyl)cyclobutyl]methyl (1S)-1-(oxo{[(1R)-1-phenylethyl]amino}acetyl)pentylcarbamate

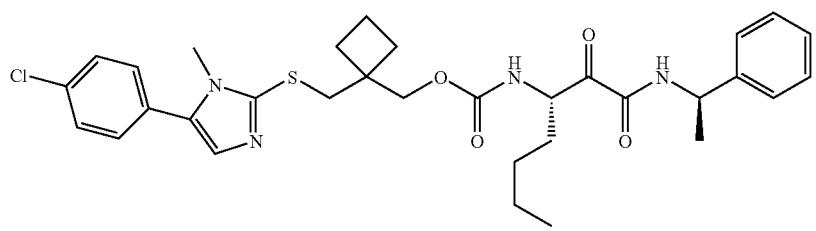

Example 34a

Preparation of [1-({[5-(4-chlorophenyl)-1-methyl-1H-imidazol-2-yl]sulfanyl}methyl)cyclobutyl]methanol

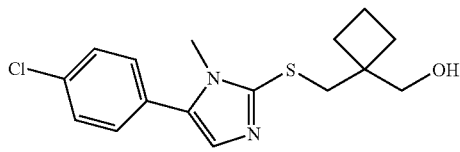

The title compound was prepared using the same experimental procedure as in example 19a from [1-(hydroxymethyl)cyclobutyl]methanol and 5-(4-chlorophenyl)-1-methyl-1H-imidazole-2-thiol. $^1$H NMR (300 MHz, CDCl$_3$) δ 7.41-7.25 (m, 5H), 3.62 (s, 2H), 3.49 (s, 3H), 3.46 (s, 2H), 2.04-1.63 (m, 6H).

Example 34b

Preparation of [1-({[5-(4-chlorophenyl)-1-methyl-1H-imidazol-2-yl]sulfanyl}methyl)cyclobutyl]methyl (1S)-1-(1-hydroxy-2-oxo-2-{[(1R)-1-phenylethyl]amino}ethyl)pentylcarbamate

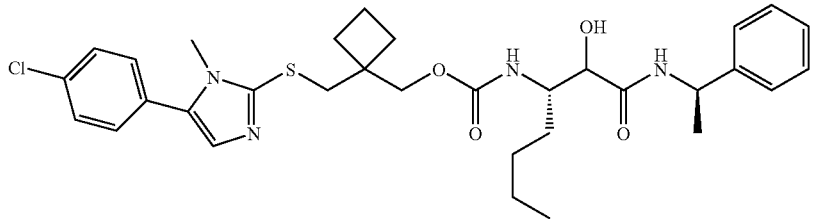

The title compound was prepared using the same experimental procedure as in example 20b from [1-({[5-(4-chlorophenyl)-1-methyl-1H-imidazol-2-yl]sulfanyl}methyl)cyclobutyl]methanol as the alcohol component and (3S)-3-amino-2-hydroxy-N-[(1R)-1-phenylethyl]heptanamide as the aminoalcohol component. $^1$H NMR (300 MHz, CDCl$_3$) δ 7.41-7.20 (m, 10 H), 7.02 (s, 1H), 5.33 (d, J=8 Hz, 1H), 5.12-5.05 (m, 2H), 4.30 (s, 1H), 4.17-4.04 (m, 3H), 3.89 (m, 2H), 3.55 (s, 2H), 3.32, 3.38 (2s, 2H), 2.03-1.88 (m, 6H), 1.55-1.22 (m, 9H), 0.82 (m, 3H). LC-MS m/z 613 (M+H).

Example 34c

Preparation of [1-({[5-(4-chlorophenyl)-1-methyl-1H-imidazol-2-yl]sulfanyl}methyl)cyclobutyl]methyl (1S)-1-(oxo{[(1R)-1-phenylethyl]amino}acetyl)pentylcarbamate

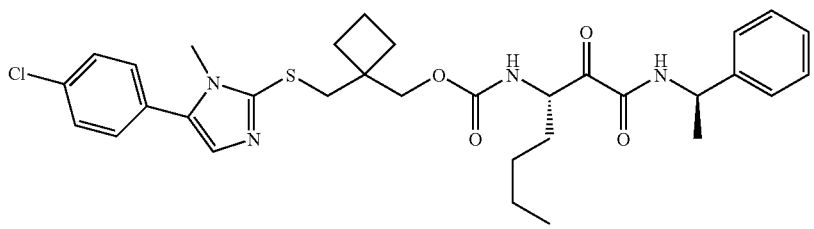

The title compound was prepared using the same experimental procedure as in example 23c from [1-({[5-(4-chlorophenyl)-1-methyl-1H-imidazol-2-yl]sulfanyl}methyl)cyclobutyl]methyl (1S)-1-(1-hydroxy-2-oxo-2-{[(1R)-1-phenylethyl]amino}ethyl)pentylcarbamate as the alcohol component. $^1$H NMR (300 MHz, CDCl$_3$) δ 7.41-7.11 (m, 11H), 7.08 (s, 1H), 5.40 (m, 1H), 5.09 (m, 2H), 4.12 (s, 2H), 3.54 (s, 3H), 3.45 (s, 2H), 2.08-1.90 (m, 6H), 1.55-1.29 (m, 9H), 0.87 (t, J=7 Hz, 3H). LC-MS m/z 611 (M+H).

Example 35

{1-[(4-methyl-1,3-thiazol-2-yl)methyl]cyclobutyl}methyl (1S)-1-(oxo{[(1R)-1-phenylethyl]amino}acetyl)pentylcarbamate

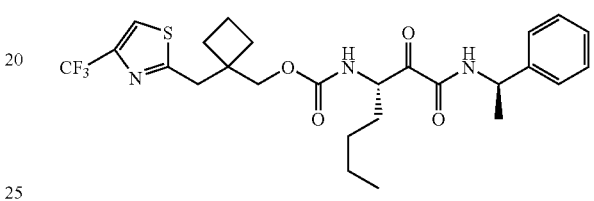

Example 35a

Preparation of {1-[(4-methyl-1,3-thiazol-2-yl)methyl]cyclobutyl}methanol

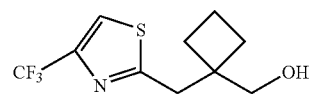

The title compound was prepared using the same experimental procedure as in examples 18f and 18g from 2-{1-[(benzyloxy)methyl]cyclobutyl}ethanethioamide and 1-bromo-4,4,4-trifluoro-2-butanone. $^1$H NMR (300 MHz, CDCl$_3$) δ 7.25 (s, 1H), 3.35 (s, 2H), 2.82 (br s, 2H), 2.02-1.91 (m, 6H).

Example 35b

Preparation of {1-[(4-methyl-1,3-thiazol-2-yl)methyl]cyclobutyl}methyl (1S)-1-(1-hydroxy-2-oxo-2-{[(1R)-1-phenylethyl]amino}ethyl)pentylcarbamate

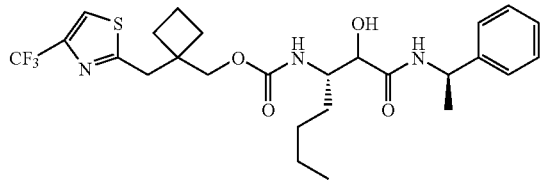

The title compound was prepared using the same experimental procedure as in example 18h from (1-{[4-(trifluoromethyl)-1,3-thiazol-2-yl]methyl}cyclobutyl)methanol. $^1$H NMR (300 MHz, CDCl$_3$) δ 7.34-7.13 (m, 6H), 5.16-5.09 (m, 1H), 4.84 (m, 1H), 4.24-4.12 (m, 2H), 3.82 (m, 1H), 3.60 (m, 1H), 3.34 (s, 2H), 2.82 (s, 2H), 2.02-1.92 (m, 6H), 1.65 (m, 2H), 1.49 (d, J=7 Hz, 3H), 1.47-1.27 (m, 4H), 0.85 (m, 3H). LC-MS m/z 542 (M+H).

Example 35c

Preparation of {1-[(4-methyl-1,3-thiazol-2-yl)methyl]cyclobutyl}methyl (1S)-1-(oxo{[(1R)-1-phenylethyl]amino}acetyl)pentylcarbamate

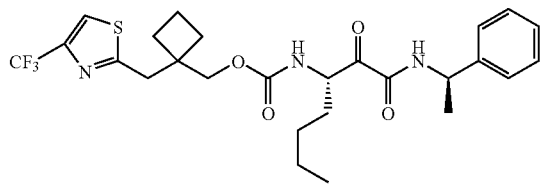

The title compound was prepared using the same experimental procedure as in example 23c from (1-{[4-(trifluoromethyl)-1,3-thiazol-2yl]methyl}cyclobutyl)methyl(1S)-1-(1-hydroxy-2-oxo-2-{[(1R)-1-phenylethyl]amino}ethyl)pentylcarbamate as the alcohol component. $^1$H NMR (300 MHz, CDCl$_3$) δ 7.35-7.11 (m, 7H), 5.33 (m, 1H), 5.12-5.05 (m, 2H), 4.15 (s, 2H), 2.82 (s, 2H), 2.04-1.92 (m, 6H), 1.61 (m, 2H), 1.53 (d, J=7 Hz, 3H), 1.42-1.31 (m, 4H), 0.86 (br s, 3H). LC-MS m/z 540 (M+H).

Example 36

(1-{2-[(1-methyl-1H-imidazol-2-yl)sulfanyl]ethyl}cyclobutyl)methyl (1S)-1-(oxo{[(1R)-1-phenylethyl]amino}acetyl)pentylcarbamate

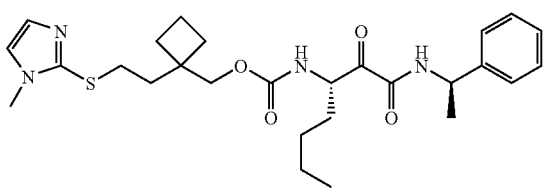

Example 36a

Preparation of Ethyl 1-[2-(benzyloxy)ethyl]cyclobutanecarboxylate

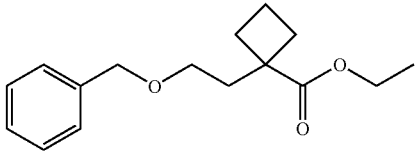

A solution of 3.0 g (23 mmol) of ethyl cyclobutanecarboxylate in 10 mL of tetrahydrofuran was added to a −78° C. solution of 25.74 mmol of lithium diisopropylamide in 45 ml tetrahydrofuran. The reaction was warmed to 0° C. over 15 min and then cooled to −78° C., followed by the addition of 3.64 mL (25.74 mmol) of benzyl 2-bromoethyl ether in 10 mL of tetrahydrofuran. The reaction was gradually warmed to room temperature over 16 h and then quenched with 20 mL of saturated ammonium chloride. The reaction was concentrated and ethyl acetate was added. The organic layer was isolated, dried with magnesium sulfate, and concentrated under vacuum to afford an oil, which was purified by silica gel chromatography eluting with ethyl acetate:hexane (2:8) to afford 4.3 g (70%) of ethyl 1-[2-(benzyloxy)ethyl]cyclobutanecarboxylate as a colorless oil. $^1$H NMR (300 MHz, CDCl$_3$) δ 7.31-7.22 (m, 5H), 4.01 (q, J=7 Hz, 2H), 4.40 (s, 2H), 2.40 (t, J=7 Hz, 2H), 1.92-1.84 (m, 6H), 1.14 (t, J=7 Hz, 3H). GC-MS m/z 263 (M+H).

Example 36b

Preparation of {1-[2-(benzyloxy)ethyl]cyclobutyl}methanol

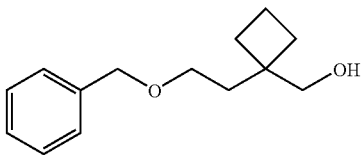

To a solution of 2.0 g (7.63 mmol) of ethyl 1-[2-(benzyloxy)ethyl]cyclobutanecarboxylate in 20 mL of diethyl ether at 0° C. was added a 1.0 M solution of 15.9 mL (15.9 mmol) of lithium aluminum hydride in tetrahydrofuran and the contents stirred for 2 h. The reaction was quenched with 20 ml of 20% sodium hydroxide solution. After filtration, the organic phase was isolated, dried with magnesium sulfate, and concentrated under vacuum to afford 1.6 g (95%) of {1-[2-(benzyloxy)ethyl]cyclobutyl}methanol as a colorless oil. $^1$H NMR (300 MHz, CDCl$_3$) δ 7.41-7.30 (m, 5H), 4.54 (s, 2H), 3.55 (t, J=6 Hz, 2H), 2.03-1.83 (m, 8H).

Example 36c

Preparation of 2-[1-({[tert-butyl(dimethyl)silyl]oxy}methyl)cyclobutyl]ethanol

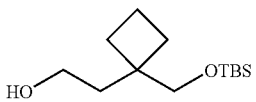

To a solution of 1.6 g (7.27 mmol) of {1-[2-(benzyloxy)ethyl]cyclobutyl}methanol in 16 mL of dichloromethane was added 1.20 g (7.99 mmol) of t-butyldimethylsilyl chloride and 0.98 g (14.54 mmol) of imidazole and the contents stirred for 16 h. Saturated ammonium chloride was added and the layers separated. The organic layer was dried with magnesium sulfate and concentrated under vacuum. To the crude silyl alcohol was added 20 mL of methanol and 0.24 g of 10 wt % palladium on carbon. The reaction was stirred under an atmosphere of hydrogen for 16 h. The contents were filtered and the filtrate was concentrated under vacuum to afford 1.71 g (97%) of 2-[1-({[tert-butyl(dimethyl)silyl]oxy}methyl)cyclobutyl]ethanol as a colorless oil. $^1$H NMR (300 MHz, CDCl$_3$) δ 3.57 (s, 2H), 3.55 (t, J=6 Hz, 2H), 1.87-1.59 (m, 8H), 0.87 (2, 9H), 0.05 (s, 6H).

Example 36d

Preparation of 2-({2-[1-({[tert-butyl(dimethyl)silyl]oxy}methyl)cyclobutyl]ethyl}sulfanyl)-1-methyl-1H-imidazole

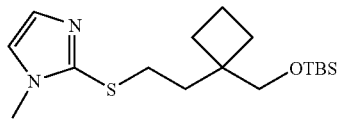

The title compound was prepared using the same experimental procedure as in example 19a using 2-[1-({[tert-butyl(dimethyl)silyl]oxy}methyl)cyclobutyl]ethanol and 1-methyl-1H-imidazole-2-thiol. $^1$H NMR (300 MHz, CDCl$_3$) δ 7.22 (s, 1H), 7.01 (s, 1H), 3.58 (s, 3H), 3.43 (s, 2H), 1.85-1.73 (m, 6H), 2.91 (t, J=6 Hz, 2H), 1.48 (s, 9H), 1.21 (t, J=4 Hz, 2H), 0.04 (s, 6H). GC-MS m/z 341 (M+H).

Example 36e

Preparation of (1-{2-[(1-methyl-1H-imidazol-2-yl)sulfanyl]ethyl}cyclobutyl)methanol

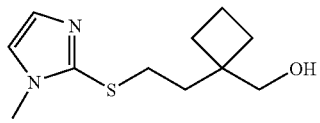

To 1.39 g (4.1 mmol) of 2-({2-[1-({[tert-butyl(dimethyl)silyl]oxy}methyl)cyclobutyl]ethyl}sulfanyl)-1-methyl-1H-imidazole in 10 mL of tetrahydrofuran was added a 1.0 M solution of 4.92 mL (5.33 mmol) of tetrabutylammonium fluoride in tetrahydrofuran and the contents stirred for 16 h. The reaction was concentrated and the residue was poured directly onto a column of silica gel eluting with ethyl acetate:hexane to afford 0.57 g (62%) of (1-{2-[(1-methyl-1H-imidazol-2-yl)sulfanyl]ethyl}cyclobutyl)methanol as a colorless oil. $^1$H NMR (300 MHz, CDCl$_3$) δ 6.94 (s, 1H), 6.82 (s, 1H), 5.30 (br s, 1H), 3.66 (s, 2H), 3.47 (s, 3H), 2.94 (m, 2H),1.99-1.64 (m, 8H).

Example 36f

Preparation of (1-{2-[(1-methyl-1H-imidazol-2-yl)sulfanyl]ethyl}cyclobutyl)methyl (1S)-1-(1-hydroxy-2-oxo-2-{[(1R)-1-phenylethyl]amino}ethyl)pentylcarbamate

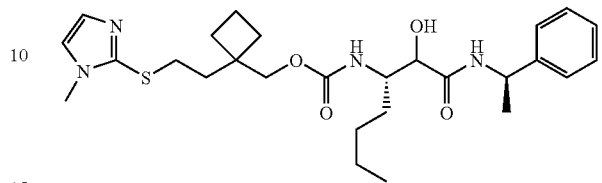

The title compound was prepared using the same experimental procedure as in example 20b from (1-{2-[(1-methyl-1H-imidazol-2-yl)sulfanyl]ethyl}cyclobutyl) methanol as the alcohol component and (3S)-3-amino-2-hydroxy-N-[(1R)-1-phenylethyl]heptanamide as the amino alcohol component. $^1$H NMR (300 MHz, CDCl$_3$) δ 8.24 (m, 1H), 7.35-7.23 (m, 5H), 7.02 (s, 1H), 6.93, 6.90 (2s, 1H), 5.67 (m, 1H), 5.16 (m, 2H), 4.22-3.74 (m, 4H), 3.65 (s, 3H), 2.95 (m, 2H), 2.03-1.79 (m, 8H), 1.49 (d, J=7 Hz, 3H), 1.36-1.27 (m, 6H), 0.91 (m, 3H). LC-MS m/z 517 (M+H).

Example 36 g

Preparation of (1-{2-[(1-methyl-1H-imidazol-2-yl)sulfanyl]ethyl}cyclobutyl)methyl (1S)-1-(oxo{[(1R)-1-phenylethyl]amino}acetyl)pentylcarbamate

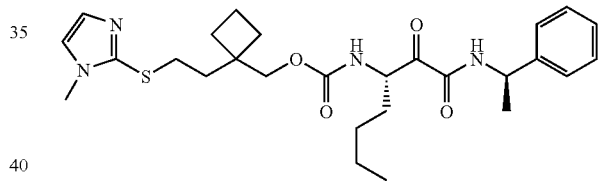

The title compound was prepared using the same experimental procedure as in example 23c from (1-{2-[(1-methyl-1H-imidazol-2-yl)sulfanyl]ethyl}cyclobutyl)methyl (1S)-1-(1-hydroxy-2-oxo-2-{[(1R)-1-phenylethyl]amino}ethyl)pentylcarbamate as the alcohol component. $^1$H NMR (300 MHz, CDCl$_3$) δ 7.44-7.33 (m, 6H), 7.30 (s, 1H), 7.14 (s 1H), 5.11 (d, J=7 Hz, 1H), 5.09 (m, 2H), 4.07 (s, 2H), 3.76 (s, 3H), 3.02 (s, 2H), 2.03-1.85 (m, 10H), 1.56 (d, J=7 Hz, 3H), 1.52-1.27 (m, 4H), 0.87 (t, J=7 Hz, 3H). LC-MS m/z 515 (M+H).

Example 37

(1-{3-[(1-methyl-1H-imidazol-2-yl)sulfanyl]propyl}cyclobutyl)methyl (1S)-1-(oxo{[(1R)-1-phenylethyl]amino}acetyl)pentylcarbamate

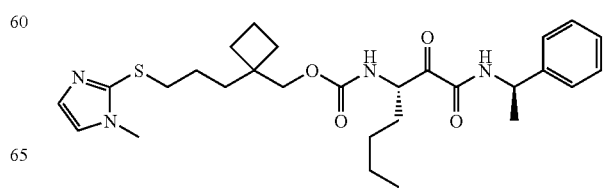

Example 37a

Preparation of Ethyl 1-[3-(benzyloxy)propyl]cyclobutanecarboxylate

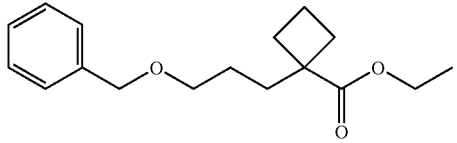

The title compound was prepared using the same experimental procedure as in example 36a using benzyl 3-bromopropyl ether as the electrophile. ¹H NMR (300 MHz, CDCl₃) δ 7.38-7.30 (m, 5H), 4.53 (s, 2H), 4.14 (t, J=7 Hz, 2H), 3.48 (t, J=6 Hz, 2H), 2.49-2.43 (m, 2H), 2.08-1.72 (m, 6H), 1.53 (m, 2H), 1.27 (t, J=7 Hz, 3H).

Example 37b

Preparation of 3-[1-({[tert-butyl(dimethyl)silyl]oxy}methyl)cyclobutyl]-1-propanol

The title compound was prepared from ethyl 1-[3-(benzyloxy)propyl]cyclobutanecarboxylate using the same experimental procedure as in examples 36b and 36c. ¹H NMR (300 MHz, CDCl₃) δ 3.62 (s, 2H), 3.46 (s, 2H), 1.84-1.41 (m, 11H), 0.88 (s, 9H), 0.03 (s, 6H).

Example 37c

Preparation of (1-{3-[(1-methyl-1H-imidazol-2-yl)sulfanyl]propyl}cyclobutyl)methanol

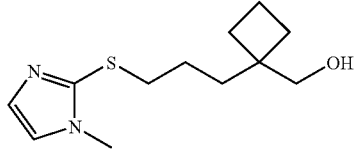

The title compound was prepared from 3-[1-({[tert-butyl(dimethyl)silyl]oxy}methyl)cyclobutyl]-1-propanol using the same experimental procedure as in examples 36d and 36e. ¹H NMR (300 MHz, CDCl₃) δ 7.30 (s, 1H), 7.07 (s, 1H), 3.91 (br ss, 1H), 3.69 (s, 3H), 3.55 (s, 2H), 2.91 (t, J=7 Hz, 2H), 1.91-1.70 (m, 8H), 1.58-1.46 (m, 2H).

Example 37d

Preparation of (1-{3-[(1-methyl-1H-imidazol-2-yl)sulfanyl]propyl}cyclobutyl)methyl (1S)-1-(1-hydroxy-2-oxo-2-{[(1R)-1-phenylethyl]amino}ethyl)pentylcarbamate

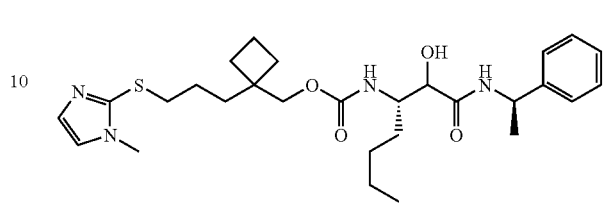

The title compound was prepared using the same experimental procedure as in example 20b from (1-{3-[(1-methyl-1H-imidazol-2-yl)sulfanyl]propyl}cyclobutyl) methanol as the alcohol component and (3S)-3-amino-2-hydroxy-N-[(1R)-1-phenylethyl]heptanamide as the amino alcohol component. ¹H NMR (300 MHz, CDCl₃) δ 7.49-7.05 (m, 6H), 6.99 (s, 1H), 6.91 (s, 1H), 5.64 (m, 1H), 5.12 (m, 1H), 4.14, (m, 4H), 3.95 (m, 1H), 3.62, 3.64 (2s, 3H), 3.25 (m, 2H), 2.08-1.71 (m, 12H), 1.49 (d, J=7 Hz, 3H), 1.41-1.32 (m, 4H), 1.29 (m, 3H). LC-MS m/z 531 (M+H).

Example 37e

Preparation of (1-{3-[(1-methyl-1H-imidazol-2-yl)sulfanyl]propyl}cyclobutyl)methyl (1S)-1-(oxo{[(1R)-1-phenylethyl]amino}acetyl)pentylcarbamate

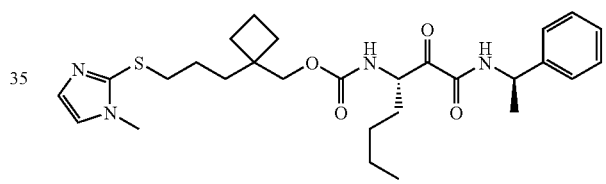

The title compound was prepared using the same experimental procedure as in example 23c using (1-{3-[(1-methyl-1H-imidazol-2-yl)sulfanyl]propyl}cyclobutyl) methyl (1S)-1-(1-hydroxy-2-oxo-2-{[(1R)-1-phenylethyl]amino}ethyl)pentylcarbamate as the alcohol component. ¹H NMR (300 MHz, CDCl₃) δ 7.12-7.45 (m, 7H), 6.99 (s, 1H), 5.56-5.33 (m, 2H), 5.16 (m, 1H), 4.01 (s, 2H), 3.67 (s, 3H), 3.01 (s, 2H), 2.08-1.89 (m, 7H), 1.85-1.61 (m, 12H), 0.87 (m, 3H). LC-MS m/z 529 (M+H).

Example 38

(1-{3-[(2-chloro-4-pyrimidinyl)oxy]propyl}cyclobutyl)methyl (1S)-1-(oxo{[(1R)-1-phenylethyl]amino}acetyl)pentylcarbamate

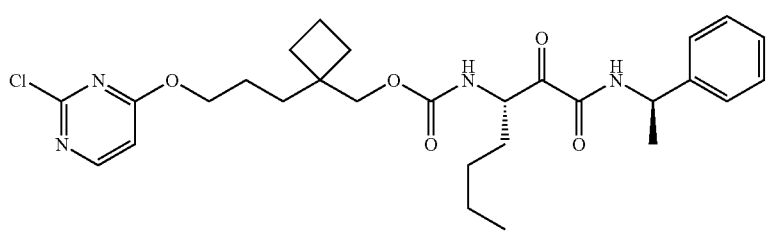

Example 38a

Preparation of 4-{3-[1-({[tert-butyl(dimethyl)silyl]oxy}methyl)cyclobutyl]propoxy}-2-chloropyrimidine

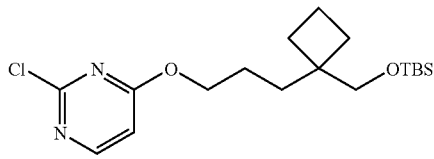

The title compound was prepared from 3-[1-({[tert-butyl(dimethyl)silyl]oxy}methyl)cyclobutyl]-1-propanol and 2,4-dichloropyrimidine using the same experimental procedure as in example 25a. $^1$H NMR (300 MHz, CDCl$_3$) δ 8.23 (d, J=6 Hz, 1H), 6.59 (d, J=6 Hz, 1H), 4.33 (t, J=6 Hz, 2H), 3.44 (s, 2H), 1.81-1.51 (m, 8H), 1.21 (m, 2H), 0.84 (s, 9H), −0.002 (s, 6H). GC-MS m/z 371 (M+H).

Example 38b

Preparation of (1-{3-[(2-chloro-4-pyrimidinyl)oxy]propyl}cyclobutyl)methanol

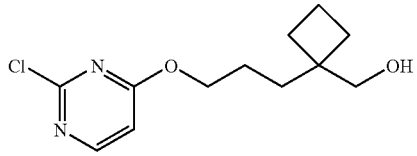

The title compound was prepared from 4-{3-[1-({[tert-butyl(dimethyl)silyl]oxy}methyl)cyclobutyl]propoxy}-2-chloropyrimidine using the same experimental procedure as in example 36e to afford (1-{3-[(2-chloro-4-pyrimidinyl)oxy]propyl}cyclobutyl)methanol. $^1$H NMR (300 MHz, CDCl$_3$) δ 8.31 (d, J=6 Hz, 1H), 6.69 (d, J=6 Hz, 1H), 4.43 (t, J=6 Hz, 2H), 3.61 (s, 2H), 1.98-1.46 (m, 10H).

Example 38c (1-{3-[(2-chloro-4-pyrimidinyl)oxy]propyl}cyclobutyl)methyl (1S)-1-(1-hydroxy-2-oxo-2-{[(1R)-1-phenylethyl]amino}ethyl)pentylcarbamate

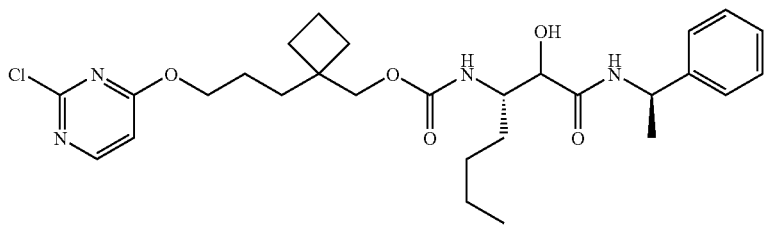

The title compound was prepared using the same experimental procedure as in example 20b from (1-{3-[(2-chloro-4-pyrimidinyl)oxy]propyl}cyclobutyl)methanol as the alcohol component and (3S)-3-amino-2-hydroxy-N-[(1R)-1-phenylethyl]heptanamide as the amino alcohol component. $^1$H NMR (300 MHz, CDCl$_3$) δ 8.30 (d, J=6 Hz, 1H), 7.38-7.17 (m, 6H), 6.69 (d, J=6 Hz, 1H), 5.62 (d, J=9 Hz, 1H), 5.33 (m, 1H), 4.98 (d, J=6 Hz, 1H), 4.40 (m, 2H), 4.15-3.86 (m, 3H), 1.89-1.58 (m, 8H), 1.52 (d, J=7 Hz, 3H), 1.39 (m, 2H), 0.92 (m, 3H). LC-MS m/z 547 (M+H).

Example 38d

Preparation of (1-{3-[(2-chloro-4-pyrimidinyl)oxy]propyl}cyclobutyl)methyl (1S)-1-(oxo{[(1R)-1-phenylethyl]amino}acetyl)pentylcarbamate

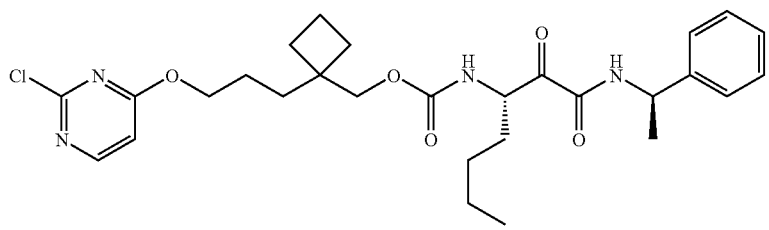

The title compound was prepared using the same experimental procedure as in example 23c using (1-{3-[(2-chloro-4-pyrimidinyl)oxy]propyl}cyclobutyl)methyl (1S)-1-(1-hydroxy-2-oxo-2-{[(1R)-1-phenylethyl]amino}ethyl)pentylcarbamate as the alcohol component. $^1$H NMR (300 MHz, CDCl$_3$) δ 8.32 (d, J=6 Hz, 1H), 7.41-7.29 (m, 5H), 7.17 (d, J=8 Hz, 1H), 6.70 (d, J=6 Hz, 1H), 5.32 (d, J=8 Hz, 1H), 5.19 (m, 2H), 4.42 (t, J=6 Hz, 1H), 4.08 (s, 2H), 1.94-1.61 (m, 8H), 1.59 (d, J=7 Hz, 3H), 1.37 (m, 2H), 0.92 (t, J=7 Hz, 3H). LC-MS m/z 545 (M+H).

Biological Data

The compounds of the present invention elicit important and measurable pharmacological responses. Each of the compounds exemplified in the Examples section bind with high affinity (IC$_{50}$<10 μM) to the cathepsin K enzyme, as described by the cathepsin K assay recited below.

All assays for cathepsin K were carried out with human and rat recombinant enzyme. Assays for cathepsins S & V were also carried out with human recombinant enzyme. Assays for human cathepsins B, H, and L were carried out with enzyme, purchased from Athens Research and Technology, Inc., prepared from human liver tissue. Standard assay conditions for the determination of kinetic constants used a fluorogenic peptide substrate, typically (5S,8S)-13-amino-5-benzyl-13-imino-3-methylene-N-(4-methyl-2-oxo-2H-chromen-7-yl)-6-oxo-1-phenyl-2-oxa-4,7,12-triaza-tridecane-8-carboxamide (Cbz-Phe-Arg-AMC), and were determined in 100 mM sodium acetate at pH 5.5 containing 10 mM dithiothreitol and 120 mM sodium chloride. A stock substrate solution of Cbz-Phe-Arg-AMC was prepared at a concentration of 50 mM in dimethyl sulfoxide. This substrate was diluted into the assay for a final substrate concentration of 10 µM in the rat cathepsin K, human cathepsin K, and human cathepsin B assays; a final substrate concentration of 5 µM in the human cathepsin L assay; and a final substrate concentration of 2 µM in the human cathepsin V assay.

A stock substrate solution of benzyl (1S)-1-{[((1S)-1-{[((1S)-4-{[amino(imino)methyl]amino}-1-{[(4-methyl-2-oxo-2H-chromen-7-yl)amino]carbonyl}butyl)amino]carbonyl}-2-methylpropyl)amino]carbonyl}-2-methylpropylcarbamate (Cbz-Val-Val-Arg-AMC) was prepared at a concentration of 10 mM in dimethyl sulfoxide. This substrate was diluted into the assay for a final substrate concentration of 10 µM in the human cathepsin S assay.

A stock substrate solution of (2S)-2-amino-5-{[amino(imino)methyl]amino}-N-(2-naphthyl)pentanamide hydrochloride (L-Arg-β-naphthalamide.HCl) was prepared at a concentration of 10 mM in dimethyl sulfoxide. This substrate was diluted into the assay for a final substrate concentration of 50 µM in the cathepsin H assay.

All assays contained 10% dimethyl sulfoxide. Independent experiments found that this level of dimethyl sulfoxide had no effect on kinetic enzymatic constants. All assays were conducted at 30° C. Product fluorescence (excitation at 360 nm; emission at 440 nm, (except cathepsin H which used excitation at 340 nm; emission at 420 nm)) was monitored with a PerSeptive Biosystems Cytofluor II fluorescence plate reader. Product progress curves were generated over 2.3 h monitoring the formation of 7-amino-4-methylcoumarin product (or β-naphthalamide for cathepsin H).

Human and Rat Cathepsin K:

Scale-Up and Fermentation: The method of O'Reilly et al. (1994) was used for baculovirus expression with the following details. Two liters of *Spodoptera frugiperda* (Sf-9) cells (ATCC) were grown in Grace's Supplemented medium (Life Technologies) supplemented with 2 g/L glucose, 10% fetal bovine serum (HyClone) and 0.1% pluronic F-68 (Life Technologies). Cells were grown in a 6 L shake flask at 150 RPM at 28° C. for 24 h to a density of 106 cells/mL, and then infected at a multiplicity of infection (MOI) of 0.1. The cells continued to grow for 72 h post-infection, before the virus was harvested by centrifugation at 1400×g for 30 min. Virus was titered as described (Summers and Smith, 1987).

One and one-half liters of *Trichoplusia ni* (*T. ni*) High Five (™) cells [JRH Biosciences, Woodland, Calif. (adapted to suspension and serum-free medium)] grown in Excell 405 (™) medium (JRH Biosciences) with 50 ug/mL gentamicin (Life Technologies) were added to a 15 L stirred tank reactor (Quark Enterprises, Inc) at a density of ~0.5×106 cells/mL The cells were grown for 24 h at 28° C., 50 RPM, and 50% dissolved oxygen. Cells were then infected at a density of ~106 cells/mL with an MOI of 1 and grown for 48 h post-infection. Media were separated from cells at a rate of 1 L/min using the Centritech 100 (™) continuous-flow centrifuge (DuPont) operating at 200×g.

Protein Purification: Media (human and rat) were filtered through a Whatman 3 filter, and then loaded onto a 25 mL Poros HS II (26 mm×47 mm) cation exchange column equilibrated in 25 mM sodium acetate at pH 5.5 (equilibration buffer). The column was washed until the absorbance reached the baseline value, and then the protein was eluted with a linear gradient from 0-2 M sodium chloride in the equilibration buffer. Column fractions were analyzed by SDS-PAGE, N-terminal sequencing, and mass spectrometry. Fractions containing the proform of cathepsin K were pooled and frozen at −80° C. The proform was concentrated in an Amicon Centriprep 10 and fractionated with a Superdex 75 column (26 mm×600 mm, Pharmacia) equilibrated in 400 mM sodium chloride, 25 mM sodium acetate at pH 5.5.

Cathepsin K Activation: The proform of cathepsin K was converted to mature cathepsin K by brief exposure to pH 4 in the presence of 5 mM L-cysteine. Typically, 5 mM L-cysteine was added to 10 mL of approximately 1 mg/mL procathepsin K. One mL of this solution was diluted ten-fold into 450 mM sodium acetate at pH 4.0 containing 5 mM L-cysteine. This solution was reacted at 23° C. for 2 min before neutralization with 2 mL 1.8 M sodium acetate at pH 6.0. The neutralized sample was added to the remaining 9 mL of procathepsin K. The mixture was incubated at 4° C. for 2-3 days. The activated cathepsin K was chromatographed on a Poros HS II column as described above.

Inhibition Studies

Potential inhibitors were evaluated using the progress curve method. Assays were carried out in the presence of variable concentrations of test compound. Reactions were initiated by addition of buffered solutions of inhibitor and substrate to enzyme. Data analysis was conducted according to one of two procedures depending on the appearance of the progress curves in the presence of inhibitors. For those compounds whose progress curves were linear, the enzymatic activity (RATE) was plotted against the concentration of test compound, including inhibitor concentration of zero ([I]=0), and the $IC_{50}$ determined from a fit of equation 1 to the data, $$RATE = V_{max}/(1+([I]/IC50)) \qquad (1)$$

where $V_{max}$ is the best fit estimate of the maximal enzymatic activity. $K_i$ values were calculated from $IC_{50}$ values using equation 2 assuming a competitive model.

$$K_i = IC_{50} * \left[1 - \frac{S}{(S+K_m)}\right] \qquad (2)$$

For those compounds whose progress curves showed downward curvature characteristic of time-dependent inhibition, the data from individual sets was analyzed using the computer program DynaFit (Kuzmic, P. *Anal. Biochem.* 1996, 237, 260-273) to give Ki values according to the following kinetic mechanism:

E+S⇔ES

ES→E+P

E→EX

E+I⇔EI

TABLE 1

Inhibition of Cathepsin K ($K_i$ in nM)
Cathepsin Inhibitory Activity

| Example | hcatK $K_i$ |
|---|---|
| 1 | ++ |
| 2 | +++ |
| 3 | +++ |
| 4 | ++ |
| 5 | ++++ |
| 6 | +++ |
| 7 | +++ |
| 8 | +++ |
| 9 | +++ |
| 10 | +++ |
| 11 | ++++ |
| 12 | ++ |
| 13 | +++ |
| 14 | +++++ |
| 15 | +++++ |
| 16 | +++ |
| 17 | ++++ |
| 18 | ++++ |
| 19 | +++ |
| 20 | ++ |
| 21 | +++ |
| 22 | +++ |
| 23 | +++ |
| 24 | +++ |
| 25 | +++ |
| 26 | +++ |
| 27 | +++ |
| 28 | +++ |
| 29 | +++ |
| 30 | ++ |
| 31 | ++ |
| 32 | +++ |
| 33 | ++++ |
| 34 | ++ |
| 35 | ++++ |
| 36 | + |
| 37 | + |
| 38 | + |

\+ Inhibitors (>1000 nM)
++ Potent inhibitors (1000-100 nM)
+++ More potent inhibitors (100-10 nM)
++++ Even more potent inhibitors (10-1 nM)
+++++ Most potent inhibitors (<1 nM)

TABLE 2

Inhibition of Cathepsins (Ki in nM)

| Example | hCat B $K_i$ | hCat H $K_i$ | hCat K $K_i$ | rCat K $K_i$ | hCat L $K_i$ | hCat S $K_i$ | hCat V $K_i$ |
|---|---|---|---|---|---|---|---|
| 3 | + | + | +++ | + | + | ++ | + |
| 15 | ++ | ++ | +++++ | +++ | +++ | ++++ | ++++ |
| 17 | + | + | ++++ | +++ | +++ | +++ | +++ |

\+ Inhibitors (>1000 nM)
++ Potent inhibitors (1000-100 nM)
+++ More potent inhibitors (100-10 nM)
++++ Even more potent inhibitors (10-1 nM)
+++++ Most potent inhibitors (<1 nM)

What is claimed is:

1. A compound of Formula (I):

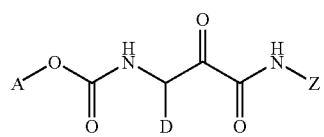

or a salt or solvate thereof:
wherein
A is the group defined by $(Q^3)-(Q^2)_n-(Q^1)-(Q)_m-$, wherein
Q is $CH_2$ and m is 0, 1, or 2
$Q^1$ is $C_3-C_7$ cycloalkylene;
$Q^2$ is $C_1-C_3$ alkylene and n is 0 or 1, or
$Q^2$ is OR, where R is $C_1-C_3$ alkylene and n is 1,
$Q^2$ is SR, where R is $C_1-C_3$ alkylene and n is 1; or
$Q^2$ is N(R')R, where R' is hydrogen or $C_1-C_6$ alkyl, R is $C_1-C_3$ alkylene and n is 1; and
$Q^3$ is aryl, heteroaryl, or aryl or heteroaryl substituted with at least one independently selected $R^1$ group, wherein said heteroaryl is selected from the group consisting of

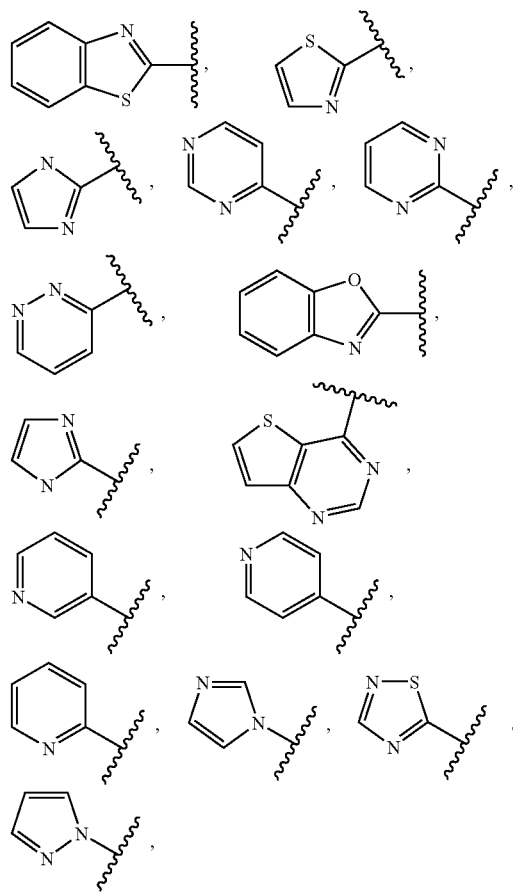

D is $C_1-C_6$ alkyl or $C_1-C_6$ alkyl substituted with $-NR^2R^3$;
Z is the group defined by $-(X)_p-(X^1)_q-(X^2)$, wherein
X is C(R')(R"), wherein R' is hydrogen or $C_1-C_6$ alkyl, R" is hydrogen and $C_1-C_6$ alkyl, and p is 0, 1, or 2, X¹ is C(O)OCH₂, wherein q is 0 or 1, and
X² is aryl, heteroaryl, or heterocyclyl wherein said heteroaryl or heterocyclyl is selected from:

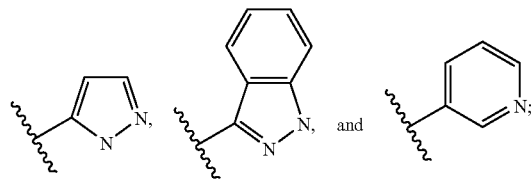

R¹ is halo, $C_1$-$C_6$ alkyl, aryl, or $C_1$-$C_6$ haloalkyl;
R² is hydrogen or $C_1$-$C_6$ alkyl;
R³ is hydrogen, $C_1$-$C_6$ alkyl, —C(O)R⁴, or —S(O)₂NR⁵R⁶;
R⁴ is —NR⁵R⁶, and
R⁵ and R⁶ are independently selected from hydrogen or $C_1$-$C_6$ alkyl.

2. A compound as claimed in claim 1, wherein Q is CH₂ and m is 0, 1, or 2.
3. A compound as claimed in claim 1, wherein Q is CH₂ and m is 0 or 1.
4. A compound as claimed in claim 1, wherein Q is CH₂ and m is 1.
5. A compound as claimed in claim 1, wherein Q¹ is $C_3$-$C_7$ cycloalkylene.
6. A compound as claimed in claim 1, wherein Q¹ is selected from the group cyclobutylene, cyclopentylene or cyclohexylene.
7. A compound as claimed in claim 1, wherein Q¹ is cyclobutylene.
8. A compound as claimed in claim 1, wherein Q² is $C_1$-$C_3$ alkylene and n is 0 or 1.
9. A compound as claimed in claim 1, wherein Q² is $C_1$-$C_3$ alkylene and n is 1.
10. A compound as claimed in claim 1, wherein Q² is OR, wherein R is $C_1$-$C_3$ alkylene and n is 1.
11. A compound as claimed in claim 1, wherein Q² is SR, wherein R is $C_1$-$C_3$ alkylene and n is 1.
12. A compound as claimed in claim 1, wherein Q³ is aryl or aryl substituted with at least one independently selected R¹ group.
13. A compound as claimed in claim 1, wherein Q³ is phenyl or phenyl substituted with at least one independently selected R¹ group wherein R¹ is halo or $C_1$-$C_6$ alkyl.
14. A compound as claimed in claim 13, wherein R¹ is halo.
15. A compound as claimed in claim 13, wherein R¹ is $C_1$-$C_6$ alkyl.
16. A compound as claimed in claim 1, wherein Q³ is heteroaryl or heteroaryl substituted with at least one independently selected R¹, wherein said heteroaryl is selected from the group consisting of

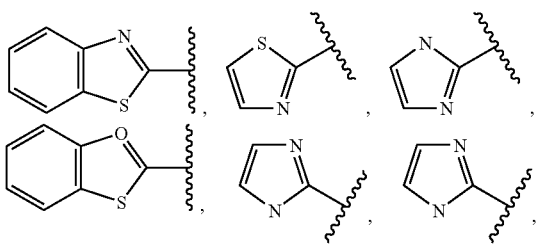

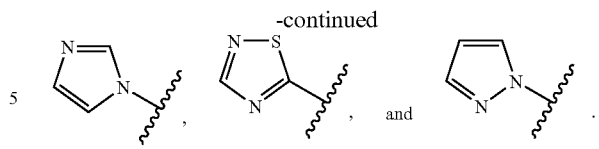

17. A compound as claimed in claim 1, wherein D is $C_1$-$C_6$ alkyl.
18. A compound as claimed in claim 1, wherein D is n-butyl.
19. A compound as claimed in claim 1, wherein X is C(H)(R") wherein R" is hydrogen and p is 0, 1, or 2.
20. A compound as claimed in claim 1, wherein X is C(R')(R") where R" is hydrogen and p is 0, 1, or 2.
21. A compound as claimed in claim 1, wherein X is C(H)(R") where R" is hydrogen and p is 0 or 1.
22. A compound as claimed in claim 1, wherein X is C(H)(R") where R" is hydrogen and p is 0.
23. A compound as claimed in claim 1, wherein X is C(H)(R") where R" is —CH₃ and p is 1.
24. A compound as claimed in claim 1, wherein X¹ is C(O)OCH₂, wherein q is 1.
25. A compound as claimed in claim 1, wherein X¹ is C(O)OCH₂, wherein q is 0.
26. A compound as claimed in claim 1, wherein X² is aryl.
27. A compound as claimed in claim 1, wherein X² is

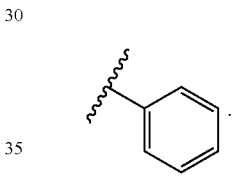

28. A compound as claimed in claim 1, wherein X² is selected from the group

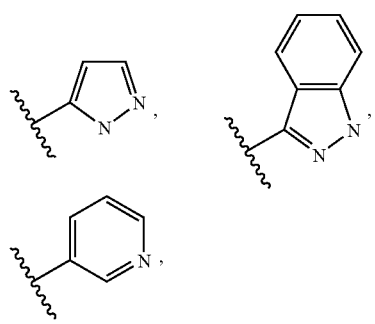

or substituted derivatives thereof.
29. A compound selected from the group consisting of:
1-benzylcyclobutyl (1S)-1-(oxo{[(1R)-1-phenylethyl]amino}acetyl)pentylcarbamate;
1-benzylcyclopentyl (1S)-1-(oxo{[(1R)-1-phenylethyl]amino}acetyl)pentylcarbamate;
benzyl(2S)-2-{[(3S)-3-({[(1-benzylcyclopentyl)oxy]carbonyl}amino)-2-oxoheptanoyl]amino}propanoate;
1-benzylcyclohexyl (1S)-1-(oxo{[(1R)-1-phenylethyl]amino}acetyl)pentylcarbamate;
(1-Benzylcyclobutyl)methyl(1S)-1-(oxo{[(1R)-1-phenylethyl]amino}acetyl) pentyl carbamate;

[1-(2-Phenylethyl)cyclobutyl]methyl (1S)-1-(oxo{[(1R)-1-phenylethyl]amino}acetyl) pentylcarbamate;
[1-(3-Phenylpropyl)cyclobutyl]methyl (1S)-1-(oxo{[(1R)-1-phenylethyl]amino}acetyl) pentylcarbamate;
(1-Benzylcyclopentyl)methyl (1S)-1-(oxo{[(1R)-1-phenylethyl]amino}acetyl) pentyl carbamate;
[1-(2,6-difluorobenzyl)cyclobutyl]methyl (1S)-5-{[(methylamino)carbonyl]amino}-1-(oxo{[(1R)-1-phenylethyl]amino}acetyl)pentylcarbamate;
[1-(4-Fluorobenzyl)cyclobutyl]methyl (1S)-1-[oxo(1H-pyrazol-5-ylamino)acetyl]pentylcarbamate;
[1-(4-fluorobenzyl)cyclobutyl]methyl (1S)-1-[[(6-chloro-1H-indazol-3-yl)amino](oxo) acetyl]pentylcarbamate;
[1-(4-fluorobenzyl)cyclobutyl]methyl (1S)-5-{[(dimethylamino)sulfonyl]amino}-1-{oxo[(3-pyridinylmethyl)amino]acetyl}pentylcarbamate;
1-(1,3-Benzothiazol-2-yl)cyclopentyl (1S)-1-[oxo(1H-pyrazol-3-ylamino)acetyl]pentylcarbamate;
{1-[(4-phenyl-1,3-thiazol-2-yl)methyl]cyclobutyl}methyl (1S)-1-(oxo{[(1R)-1-phenylethyl]amino}acetyl)pentylcarbamate;
(1-{[(1-methyl-1H-imidazol-2-yl)sulfanyl]methyl}cyclobutyl)methyl (1S)-1-(oxo{[(1R)-1-phenylethyl]amino}acetyl)pentylcarbamate;
{1-[(1,3-benzoxazol-2-ylsulfanyl)methyl] cyclobutyl}methyl (1S)-1-(oxo{[(1R)-1-phenylethyl]amino}acetyl)pentylcarbamate;
{1-[(1,3-thiazol-2-yloxy)methyl]cyclobutyl}methyl (1S)-1-(oxo{[(1R)-1-phenylethyl]amino}acetyl)pentylcarbamate;
(1-{[(3-phenyl-1,2,4-thiadiazol-5-yl)oxy]methyl}cyclobutyl)methyl (1S)-1-(oxo{[(1R)-1-phenylethyl]amino}acetyl)pentylcarbamate;
(1-{[(1-phenyl-1H-imidazol-2-yl)sulfanyl]methyl}cyclobutyl)methyl (1S)-1-(oxo{[(1R)-1-phenylethyl]amino}acetyl)pentylcarbamate;
[1-({[4-(4-methylphenyl)-1,3-thiazol-2-yl]oxy}methyl)cyclobutyl]methyl (1S)-1-(oxo{[(1R)-1-phenylethyl]amino}acetyl)pentylcarbamate;
[1-({[5-(4-chlorophenyl)-1-methyl-1H-imidazol-2-yl]sulfanyl}methyl) cyclobutyl]methyl (1S)-1-(oxo{[(1R)-1-phenylethyl]amino}acetyl)pentylcarbamate;
{1-[(4-methyl-1,3-thiazol-2-yl)methyl]cyclobutyl}methyl (1S)-1-(oxo{[(1R)-1-phenylethyl]amino}acetyl)pentylcarbamate;
(1-{2-[(1-methyl-1H-imidazol-2-yl)sulfanyl]ethyl}cyclobutyl)methyl (1S)-1-(oxo{[(1R)-1-phenylethyl]amino}acetyl)pentylcarbamate; and
(1-{3-[(1-methyl-1H-imidazol-2-yl)sulfanyl]propyl}cyclobutyl)methyl (1S)-1-(oxo{[(1R)-1-phenylethyl]amino}acetyl)pentylcarbamate;
or a salt, or solvate thereof.

30. A pharmaceutical composition comprising a therapeutically effective amount of a compound as claimed in claim 1, or a salt or solvate thereof and one or more of pharmaceutically acceptable carriers, diluents and excipients.

31. A method of treating a disorder selected from osteoporosis, Paget's disease, hypercalcemia of malignancy, metabolic bone disease, osteoarthritis, rheumatoid arthritis, periodontitis, gingivitis, and atherosclerosis in a mammal, comprising: administering to said mammal a therapeutically effective amount of a compound as claimed in claim 1 or a salt or solvate thereof.

32. A method of treating osteoporosis, comprising: administering to said mammal a therapeutically effective amount of a compound as claimed in claim 1 or a salt or solvate thereof.

33. A method of treating osteoporosis, comprising: administering to said mammal therapeutically effective amounts of (i) a compound as claimed in claim 1, or a salt or solvate thereof and (ii) at least one bone building agent.

* * * * *